US008822409B2

(12) United States Patent
Milech et al.

(10) Patent No.: US 8,822,409 B2
(45) Date of Patent: Sep. 2, 2014

(54) COMPOSITIONS AND USES THEREOF FOR THE TREATMENT OF ACUTE RESPIRATORY DISTRESS SYNDROME (ARDS) AND CLINICAL DISORDERS ASSOCIATED WITH THEREWITH

(75) Inventors: Nadia Marian Dorothy Milech, Daglish (AU); Paul Michael Watt, Mount Claremont (AU); Patrick G. Holt, Nedlands (AU); Deborah Strickland, Subiaco (AU)

(73) Assignee: Phylogica Limited, Subiaco (AU)

( * ) Notice: Subject to any disclaimer, the term of this patent is extended or adjusted under 35 U.S.C. 154(b) by 1022 days.

(21) Appl. No.: 12/665,263

(22) PCT Filed: Jun. 20, 2008

(86) PCT No.: PCT/AU2008/000903
§ 371 (c)(1),
(2), (4) Date: Sep. 7, 2010

(87) PCT Pub. No.: WO2008/154700
PCT Pub. Date: Dec. 24, 2008

(65) Prior Publication Data
US 2011/0053831 A1   Mar. 3, 2011

Related U.S. Application Data

(60) Provisional application No. 60/945,215, filed on Jun. 20, 2007.

(51) Int. Cl.
| | |
|---|---|
| *A61K 38/16* | (2006.01) |
| *C07K 14/00* | (2006.01) |
| *C07K 14/475* | (2006.01) |
| *A61K 38/10* | (2006.01) |
| *A61K 38/08* | (2006.01) |
| *G01N 33/50* | (2006.01) |

(52) U.S. Cl.
CPC .............. *A61K 38/08* (2013.01); *A61K 38/16* (2013.01); *G01N 2800/125* (2013.01); *A61K 38/10* (2013.01); *G01N 33/5088* (2013.01)
USPC ............ 514/1.5; 514/21.3; 514/7.6; 530/324

(58) Field of Classification Search
None
See application file for complete search history.

(56) References Cited

U.S. PATENT DOCUMENTS

| | | | |
|---|---|---|---|
| 5,516,637 A | 5/1996 | Huang et al. |
| 5,763,239 A | 6/1998 | Short et al. |
| 5,783,431 A | 7/1998 | Peterson et al. |
| 5,821,047 A | 10/1998 | Garrard et al. |
| 5,834,247 A | 11/1998 | Comb et al. |
| 5,843,698 A | 12/1998 | Sorensen |
| 6,074,815 A | 6/2000 | Sorensen |
| 6,083,715 A | 7/2000 | Georgiou et al. |
| 6,150,127 A | 11/2000 | Sorensen |
| 6,174,673 B1 | 1/2001 | Short et al. |
| 6,190,908 B1 | 2/2001 | Kang |
| 6,221,355 B1 | 4/2001 | Dowdy |
| 6,225,530 B1 | 5/2001 | Weigel et al. |
| 6,238,884 B1 | 5/2001 | Short et al. |
| 6,297,004 B1 | 10/2001 | Russell et al. |
| 6,316,223 B1 | 11/2001 | Payan et al. |
| 6,319,690 B1 | 11/2001 | Little et al. |
| 6,361,969 B1 | 3/2002 | Galeotti |
| 6,436,694 B1 | 8/2002 | Tally et al. |
| 6,475,726 B1 | 11/2002 | Tally et al. |
| 6,521,425 B2 | 2/2003 | Perler et al. |
| 6,560,542 B1 | 5/2003 | Mandell et al. |
| 6,579,675 B2 | 6/2003 | Kamb |
| 6,583,108 B1 * | 6/2003 | Tamburini et al. ........... 514/13.7 |
| 6,583,275 B1 | 6/2003 | Doucette-Stamm et al. |
| 6,610,820 B1 | 8/2003 | Bonny |
| 6,720,139 B1 | 4/2004 | Zyskind et al. |
| 6,720,413 B1 | 4/2004 | Schweinfest et al. |
| 6,846,625 B1 | 1/2005 | Tally et al. |
| 6,962,904 B1 | 11/2005 | Sandberg et al. |
| 7,041,868 B2 | 5/2006 | Greene et al. |
| 7,053,046 B2 | 5/2006 | McGrath |
| 7,117,096 B2 | 10/2006 | Luo et al. |
| 7,303,885 B1 | 12/2007 | Brunner et al. |
| 2002/0150906 A1 | 10/2002 | Debe |
| 2002/0155564 A1 | 10/2002 | Medrano et al. |
| 2002/0164735 A1 | 11/2002 | Olson et al. |
| 2005/0287580 A1 | 12/2005 | Watt et al. |
| 2007/0031832 A1 | 2/2007 | Watt |
| 2007/0060514 A1 | 3/2007 | Bonny |
| 2009/0170722 A1 | 7/2009 | Watt et al. |
| 2010/0029552 A1 | 2/2010 | Watt et al. |

FOREIGN PATENT DOCUMENTS

| | | |
|---|---|---|
| AU | 1860395 | 7/1995 |
| AU | 4808597 | 5/1998 |
| AU | 2258799 | 7/1999 |
| AU | 756617 B2 | 1/2003 |

(Continued)

OTHER PUBLICATIONS

Website: http://emedicine.medscape.com/article/165139-treatment, retrieved on Feb. 21, 2013, 3 pages.*
Website: http://www.ihacares.com/index.cfm/HealthAdvisors/AdultHealthAdvisor/crs-aha-aha_acute.respiratory.distress.syndrome/, 2 pages, retreived on Feb. 21, 2013.*
Cooper, 1990, Chest, 97, 138-143.*
Bennett, B.L., "c-Jun N-Terminal Kinase-Dependent Mechanisms in Respiratory Disease," Eur. Respir. Journal, 2006, pp. 651-661, vol. 28.
Florin, I. et al., "Identification of Novel AP-1 Target Genes in Fibroblasts Regulated During Cutaneous Wound Healing," Oncogene, 2004, pp. 7005-7017, vol. 23, No. 42.
Nguyen, C. et al., "Chemogenomic Identification of Ref-1/AP-1 as a Therapeutic Target for Asthma," Proc. Nat. Acad. Sci., Feb. 4, 2003, pp. 1169-1173, vol. 100, No. 3.

(Continued)

*Primary Examiner* — Satyanarayana R Gudibande
(74) *Attorney, Agent, or Firm* — Fenwick & West LLP

(57) ABSTRACT

Polypeptides are identified through an assay based on inhibiting AP-I signalling activity and others to treat acute respiratory distress syndrome (ARDS) and clinical disorders associated with the development of ARDS.

13 Claims, 2 Drawing Sheets

(56) References Cited

FOREIGN PATENT DOCUMENTS

| | | |
|---|---|---|
| AU | 771534 B2 | 3/2004 |
| CN | 1629637 | 6/2005 |
| EP | 1277835 A1 | 1/2003 |
| EP | 1776958 A2 | 4/2007 |
| EP | 1811033 A1 | 7/2007 |
| WO | WO 95/17412 | 6/1995 |
| WO | WO 98/15172 | 4/1998 |
| WO | WO 98/16835 | 4/1998 |
| WO | WO 99/35282 | 7/1999 |
| WO | WO 00/68373 | 11/2000 |
| WO | WO 00/76308 | 12/2000 |
| WO | WO 01/11086 | 2/2001 |
| WO | WO 01/32156 A2 | 5/2001 |
| WO | WO 03/012055 | 2/2003 |
| WO | WO 03/040168 | 5/2003 |
| WO | WO 03/046147 | 6/2003 |
| WO | WO 03/076621 | 9/2003 |
| WO | WO-2004/074479 * | 9/2004 |
| WO | WO 2004/074479 | 9/2004 |
| WO | WO 2004/074479 A1 | 9/2004 |
| WO | WO 2006/017913 | 2/2006 |
| WO | WO 2006/017913 A1 | 2/2006 |
| WO | WO 2007/031098 A1 | 3/2007 |
| WO | WO 2008/034161 A1 | 3/2008 |
| WO | WO 2008/034162 A1 | 3/2008 |
| WO | WO 2008/154700 A1 | 12/2008 |

OTHER PUBLICATIONS

PCT International Search Report, PCT Application No. PCT/AU2007/000092, Apr. 2, 2007, 3 pages.
PCT International Preliminary Examination Report, PCT Application No. PCT/AU2007/000092, Mar. 24, 2009, 7 pages.
PCT International Search Report and Written Opinion, PCT Application No. PCT/AU2007/000121, Apr. 5, 2007, 8 pages.
PCT International Preliminary Examination Report, PCT Application No. PCT/AU2007/000121, Mar. 24, 2009, 4 pages.
PCT International Search Report and Written Opinion, PCT Application No. PCT/AU2008/000903, Oct. 15, 2008, 13 pages.
PCT International Preliminary Report on Patentability, PCT Application No. PCT/AU2008/000903, Dec. 22, 2009, 7 pages.
RefSeq Accession No. XP_975325.1, NCBI Sequence Viewer v2.0, 1 page, [Online] [Retrieved on May 3, 2007].
RefSeq Accession No. ZP_01044355.1, NCBI Sequence Viewer v2.0, 2 pages, [Online] [Retrieved on May 3, 2007].
RefSeq Accession No. YP_284595.1, NCBI Sequence Viewer v2.0, 2 pages, [Online] [Retrieved on May 3, 2007].
Yates, S. et al."Transcription Factor Activation in Response to Cutaneous Injury: Role of AP-1 in Reepithelialization," Wound Repair Regeneration, 2002, pp. 5-15, vol. 10, No. 1.
Schuetz, Y. et al., "Emerging Strategies for the Transdermal Delivery of Peptide and Protein Drugs," Expert Opinion Drug Delivery, 2005, pp. 533-548, vol. 2, No. 3.
Alekshun, M.N., "Beyond Comparison—Antibodies From Genome Data?" Nature Biotechnology, Dec. 2001, pp. 1124-1125, vol. 19.
Amann, E. et al., "ATG Vectors for Regulated High-Level Expression of Cloned Genes in *Escherichia coli*," Gene, 1985, pp. 183-190, vol. 40.
Amstutz, P. et al., "In vitro Display Technologies: Novel Developments and Applications," Current Opinion in Biotechnology, 2001, pp. 400-405, vol. 12.
Andre, S. et al. (Jan. 17, 2005). "Identification of Peptide Ligands for Malignancy- and Growth-Related Galectins Using Random Phage-Display and Designed Combinatorial Peptide Libraries," Bioorganic & Medicinal Chemistry 13(2):563-573.
Angrist, M. (1998) "Less is More: Compact Genomes Pay Dividends," Genome Research 8:683-685.
Arenkov, P. et al (2000). "Protein Microchips: Use for Immunoassay and Enzymatic Reactions," Analytical Biochemistry 278:123-131.

Balaban, N. et al. (Apr. 17, 1998). "Autoinducer of Virulence as a Target for Vaccine and Therapy Against *Staphylococcus aureus*," Science 280:438-440.
Basbous, J. et al. (Oct. 31, 2003). "The HBZ Factor of Human T-cell Leukemia Virus Type 1 Dimerizes with Transcription Factors JunB and c-Jun Modulates Their Transcriptional Activity," The Journal of Biological Chemistry 278 (44): 43620-43627.
Baud, F. et al. (Oct. 26, 1999). "Measures of Residue Density in Protein Structures," Proc. Natl. Acad. Sci. USA 96:12494-12499.
Behrens, A. et al. (Mar. 1999) "Amino-Terminal Phosphorylation of c-Jun Regulates Stress-Induced Apoptosis and Cellular Proliferation," Nature Genetics 21:326-329.
Berzofsky, J.A. (Sep. 6, 1985). "Intrinsic and Extrinsic Factors in Protein Antigenic Structure," Science 229(4717):932-940.
Blum, J.H. et al. (Feb. 29, 2000), "Isolation of Peptide Aptamers That Inhibit Intracellular Processes," Proc. Natl. Acad. Sci. USA 97(5):2241-2246.
Bonaldo, M. et al. (1997). "Normalisation and Subtraction: Two Approaches to Facilitate Gene Discovery," Genome Res. 6:791-806.
Bremnes, T. et al. (1998). "Selection of Phage Displayed Peptides From a Random 10-mer Library Recognising a Peptide Target," Immunotechnology 4:21-28.
Britten, R.J. et al. (Aug. 9, 1968). "Repeated Sequences in DNA," Science 161(3841):529-540.
Brodin, N.T. et al (May 15, 1990). "Rat Monoclonal Antibodies Produced Against Rat Colorectal Adenocarcinomas Define Tumor- and Colon-Associated, Auto-Immunogenic Antigens," Int. J. Cancer 45(5):902-910.
Burioni, R. et al. (1998). "A New Subtraction Technique for Molecular Cloning of Rare Antiviral Antibody Specificities From Phage Display Libraries," Res. Virol. 149:327-330.
Campbell, A.P. et al. (1997). "Solution Secondary Structure of a Bacterially Expressed Peptide from the Receptor Binding Domain of *Pseudomonas aeruginosa* Pili Strain PAK: A Heteronuclear Multidimensional NMR Study," Biochem. 36(42):12791-12801.
Caponigro, G. et al. (Jun. 1998). "Transdominant Genetic Analysis of a Growth Control Pathway," Proc. Natl. Acad. Sci USA 95:7508-7513.
Chapman, M.D, et al. (Nov. 1984). "Recognition of two *Dermatophagoides pteronyssinus*-specific Epitopes on Antigen P1 by using Monoclonal Antibodies: Binding to Each Epitope can be Inhibited by Serum from Dust Mite-Allergic Patients," J Immunol 133(5):2488-2495.
Chevray, P.M. et al. (Jul. 1992). "Protein Interaction Cloning in Yeast: Identification of Mammalian Proteins that React with the Leucine Zipper of Jun," Proc. Natl. Acad. Sci. USA 89: 5789-5793.
Choi, Y. et al. (Mar. 2003). "Identification of Bioactive Moleculesby Adipogenesis Profiling of Organic Compounds," FASEB Meeting on Experimental Biology: Translating the Genome, San Diego, CA, Apr. 11-15, 2003, 17(4-5):A605, Abstract No. 377.23, one page.
Colas et al. (Apr. 11, 1996). "Genetic Selection of Peptide Aptamers That Recognize and Inhibit Cyclin-Dependent Kinase 2," Nature 380:548-550.
Colbére-Garapin et al. (1981). "A New Dominant Hybrid Selective Marker for Higher Eukaryotic Cells," J. Mol. Biol. 150:1-14.
Cordwell, S.J. (1999). "Microbial Genomes and 'Missing' Enzymes: Redefining Biochemical Pathways," Arch. Microbiol. 172:269-279.
Davies, J.M. et al. (Jun. 2000). "Use of Phage Display Technology to Investigate Allergen-Antibody Interactions," J. Allergy Clin. Immunol 105(6):1085-1092 2000.
De Soultrait et al. (2002). "A Novel Short Peptide is a Specific Inhibitor of the Human Immunodeficiency Virus Type 1 Integrase," J. Mol. Biol. 318:45-58.
Dent et al. (1999). "The Genetics of Ivermectin Resistance in *Caenorhabditis elegans*," Proc. Natl. Acad. Sci. USA 97:2674-2679.
DeRossi et al. (1994). "The Third Helix of the Antennapedia Homeodomain Translocates Through Biological Membranes," J. Biol. Chem. 269:10444-10450.
Deveraeux et al. (1984). "A Comprehensive Set of Sequence Analysis Programs for the VAX," Nucl. Acids Res. 12:387-395.
DeVito et al. (2002). "An Array of Target-Specific Screening Strains for Antibacterial Discovert," Nature Biotechnology 20:478-483.

(56) References Cited

OTHER PUBLICATIONS

Erdos, G. et al. (2006). "Construction and Characterization of a Highly Redundant *Pseudonomas aeruginosa* Genomic Library Prepared From 12 Clinical Isolates: Application to Studies of Gene Distribution Among Populations," Intl. Journal of Pediatric Otorhinolaryngology 70:1891-1900.

Estus, S. et al. (Dec. 1994). "Altered Gene Expression in Neurons During Programmed Cell Death: Identification of c-Jun as Necessary for Neuronal Apoptosis," The Journal of Cell Biology 127(6):1717-1727.

Faber et al. (1999). "Polyglutamine-Mediated Dysfunction and Apoptotic Death of a *Caenorhabditis elegans* Sensory Neuron," Proc. Natl. Acad. Sci. 96:179-184.

Fabret et al. (2000). "Efficient Gene Targeted Random Mutagenesis in Genetically Stable *Escherichia coli* strains," Nucl. Acids Res. 28:e95.

Fahraeus et al. (1996) "Inhibition of prb Phosphorylation and Cell-Cycle Progression by a 20-Residue Peptide Derived From p16 CDKN2/INK4An," Curr. Biol. 6(1):84-91.

Fang, Y. et al. (2002). "G-Protein-Coupled Receptor Microarrays," ChemBioChem., 3: 987-991.

Fehrsen et al. (1999). "Cross-Reactive Epitope Mimics in a Fragmented-Genome Phage Display Library Derived from the Rickettsia, *Cowdria ruminantium*," Immunotechnology 4:175-184.

Filipe, S.R. (2001). "The Role of murMN Operon in Penicillin Resistance and Antibiotic Tolerance of *Streptococcus pneumoniae*," Microbial Drug Resistance 7(4):303-316.

Fitzgerald (2000). "In vitro Display Technologies—New Tools for Drug Discovery," Drug Discovery Today 5:253-258.

Franzoni et al. (1997). "Structure of the C-Terminal Fragment 300-320 of the Rat Angiotensin II AT 1a Receptor and Its Relevance with Respect to G-Protein-Coupling," J. Biol. Chem. 272:9734-9741.

Furmonaviciene, R. et al. (1999). "The Use of Phage-Peptide Libraries to Define the Epitope Specificity of a Mouse Monoclonal Anti-Der p 1 Response," Clin. Exp. Allergy 29:1563-1571.

Futch, W.S. Jr. et al. (Mar. 15, 2003). "Dissection of Macrophage Tumoricidal and Protozoacidal Activities Using T-Cell Hybridomas and Recombinant Lymphokines," Infection and Immunity 50(3): 709-715.

Garcia, M. et al. (Mar. 15, 2002). "The Mitochondrial Toxin 3-Nitropropionic Acid Induces Striatal Neurodegeneration via a c-Jun N-Terminal Kinase/c-Jun Module," The Journal of Neuroscience 22(6):2174-2184, J. Neuroscience, 22: 2174-2184.

Gargala, G. et al. (1999). "Enzyme Immunoassay Detection of *Cryptosporidium parvum* Inhibition by Sinefungin in Sporozoite Infected HCT-8 Enterocytic Cells," International Journal of Parasitology 29: 703-709.

Gegg et al. (1997). "Probing Minimal Independent Folding Units in Dihydrofolate Reductase by Molecular Dissection," Protein Sci. 6:1885-1892.

GenBank Accession No. AAH36335 (last updated May 20, 2005), located at <http://www.ncbi.nlm.nih.gov/entrez/viewer.fcgi?db=protein&id=23273658>, last visited Apr. 1, 2008, three pages.

GenBank Accession No. AAN49594 (last updated Feb. 1, 2006), <http://www.ncbi.nlm.nih.gov/entrez/viewer.fcgi?db=protein&id=24196153>, last visited Apr. 1, 2008, two pages.

GenBank Accession No. AAS70149 (last updated Jan. 4, 2006), <http://www.ncbi.nlm.nih.gov/entrez/viewer.fcgi?db=protein&id=45600665>, last visited Apr. 1, 2008, two pages.

GenBank Accession No. AAV59791 (last updated Jan. 21, 2005), <http://www.ncbi.nlm.nih.gov/entrez/viewer.fcgi?db=protein&id=55736149>, last visited Apr. 1, 2008, three pages.

GenBank Accession No. CAD25932 (last updated Apr. 16, 2005), <http://www.ncbi.nlm.nih.gov/entrez/viewer.fcgi?db=protein&id=19069547>, last visited Apr. 1, 2008, two pages.

GenBank Accession No. CAH10659 (last updated Sep. 22, 2004), <http://www.ncbi.nlm.nih.gov/entrez/viewer.fcgi?db=protein&id=50949409>, last visited Apr. 1, 2008, two pages.

Getzoff et al. (1987). "Mechanisms of Antibody Binding to a Protein," Science 235:1191-1196.

Granger-Schnarr, M. et al. (May 1992). "Transformation and Transactivation Suppressor Activity of the c-Jun Leucine Zipper Fused to a Bacterial Repressor," Proc. Natl. Acad. Sci. USA 89:4236-4239.

Greene et al. (1992). "IgE Binding Structures of the Major House Dust Mite Allergen DER P 1," Mol. Immunology 29:257-262.

Haley, K.J. et al. (Aug. 1998). "Tumor Necrosis Factor Induces Neuroendocrine Differentiation in Small Cell Lung Cancer Cell Lines," American Journal of Physiology 275(2 pt 1):L311-L321.

Halstead, J.R. et al. (1999). "A Family 26 Mannanase Produced by *Clostridium thermocellum* as a Component of the Cellulosome Contains a Domain Which is Conserved in Mannanases from Anaerobic Fungi," Microbiology 145:3101-3108.

Hegde S. S. et al. (Mar. 9, 2001). "FemABX Family Members Are Novel Nonribosomal Peptidyltransferases and Important Pathogen-SpecificDrug Targets," The Journal of Biological Chemistry 276(10):6998-7003.

Hengeveld et al.(2002). "Functional and Structural Characterization of a Synthetic Peptide Representing the N-Terminal Domain of Prokaryotic Pyruvate Dehydrogenase," Biochem. 41:7490-7500.

Heymann et al. (1989). "Antigenic and Structural Analysis of Group II Allergens (Der f II and Der p II) From House Dust Mites (*Dermatophagoides* spp.)" J. Allergy Clin. Immunol. 83:1055-1067.

Hofmann et al. (1996). "Rapid Retroviral Delivery of Tetracycline-Inducible Genes in a Single Autoregulatory Cassette," Proc. Natl. Acad. Sci. 93:5185-5190.

Hoogenboom et al. (1991). "Multi-Subunit Proteins on the Surface of Filamentous Phage: Methodologies for Displaying Antibody (Fab) Heavy and Light Chaims," Nucleic acids Res. 19:4133-4137.

Horng et al. (2002). "Characterization of Large Peptide Fragments Derived from the N-Terminal Domain of the Ribosomal Protein L9: Definition of the Minimum Folding Motif and Characterization of Local Electrostatic Interactions," Biochem. 41:13360-13369.

Hosen, N. et al. (2004). "Identification of a Gene Element Essential for Leukemia-Specific Expression of Transgenes," Leukemia 18:415-419.

Houshmand et al. (1999). "Use of Bacteriophage T7 Displayed Peptides for Determination of Monoclonal Antibody Specificity and Biosensor Analysis of the Binding Reaction," Anal. Biochem. 268:363-370.

Humphrey et al. (1997). "Chemical Synthesis of Natural Product Peptides; Coupling Methods for the Incorporation of Noncoded Amino Acids into Peptides," Chem. Rev. 97:2243-2266.

International Preliminary Report on Patentability mailed on Feb. 20, 2007, for PCT Application No. PCT/AU2005/001255, filed Aug. 22, 2005, ten pages.

International Search Report mailed on Aug. 16, 2005, for PCT Application No. PCT/AU2005/000801, filed Jun. 3, 2005, eight pages.

International Search Report mailed on Nov. 17, 2005, for PCT Application No. PCT/AU2005/001255, filed Aug. 22, 2005, six pages.

Irbäck, et al. (1996). "Evidence for Nonrandom Hydrophobicity Structures in Protein Chains," Proc. Natl. Acad. Sci. 93:9533-9538.

Kabouridis, P. S. (Nov. 2003). "Biological Applications of Protein Transduction Technology," Trends in Biotechnology 21(11): 498-503.

Kinzler et al. (1989). "Whole Genome PCR: Application to the Identification of Sequences Bound by Gene Regulatory Proteins," Nucleic Acids Res. 17:3645-3653.

Kolonin et al. (Nov. 1998). "Targeting Cyclin-Dependent Kinases in Drosophilia with Peptide Aptamers," Proc. Natl, Acad. Sci. 95:14266-14271.

Koncz et al. (1987). "Expression and Assmebly of Functional Bacterial Luciferase in Plants," Proc. Natl. Acad. Sci. 84:131-135.

Koo, J.H. et al. (Mar. 8, 2001). "Purification and Characterization of Bex, an OMP Parter," Annual Meeting of the Federation of American Societies for Experimental Biology on Experimental Biology Orlando, FL, Mar. 31-Apr. 4, 2001, 15(5):A894,Abstract No. 695.14, one page.

Kopczynski et al. (1998). "A High Throughput Screen to Identify Secreted and Transmembrane Proteins Involved in Drosophilia embryogenesis," Proc. Natl. Acad. Sci. 95:9973-9978.

(56) References Cited

OTHER PUBLICATIONS

Lambros, C. et al. (Jun. 1979). "Synchronization of Plasmodium Falciparum Erythrocytic Stages in Culture," J. Parasitology 65(3):418-420.

Layne, M.D. et al. (Jun. 18, 1998). "Aortic Carboxypeptidase-Like Protein, Novel Protein with Discoidin and Carboxypeptidase-Like Domains, Is Up-Regulated During Vascular Smooth Muscle Cell Differentiation ," The Journal of Biological Chemistry 273(25):15654-15660.

Lee, et al (1994). "Structure-Antigenicity Relationship of Peptides from the Pre-s2 Region of the Hepatitus B Virus Surface Antigen," Biochem Mol Biol Int. 34(1):159-168.

Lee, Y. et al. (2003). "ProteoChip: A Highly Sensitive Protein Microarray Prepared by a Novel Method of Protein Immobilization for Application of Protein-Protein Interaction Studies," Proteomics, 3:2289-2304.

Leitner, A. et al. (1998) "A Mimotope Defined by Phage Display Inhibits IgE Binding to the Plant Panallergen Profiling," Eur. J. Immunol 28:2921-2927.

Lesley et al. (1991). "Use of in vitro Protein Syntheses from Polymerase Chain Reaction-Generated Templates to Study Interaction of *Escherichia coli* Transcription Factors with Core RNA Polymerase and for Epitope Mapping of Monoclonal Antibodies," J. Biol. Chem. 266:2632-2638.

Lessel, et al. (1997). "Creation and characterization of a new, non-redundant fragment data bank," Protein Engineering 10(6):659-664.

Lind, et al. (1988). "The Binding of Mouse Hybridoma and Human IgE Antibodies to the Major Fecal Allergen, Der p 1, of *Dermatophagoides pteronyssinus*," J. Immunol 40:4256-4262.

Maidhof, H. et al. (Jun. 1991). "femA, Which Encodes a Factor Essential for Expression of Methicillin Resistance, Affects Glycine Content of Peptidoglycan in Methicillin-Resistant and Methicillin-Susceptible *Staphylococcus aureus* Strains," Journal of Bacteriology 173(11):3507-3513.

Marcello et al. (Sep. 1994). "Specific Inhibition of Herpes Virus Replication by Receptor-Mediated Entry of an Antiviral Peptide Linked to *Escherichia coli* Enterotoxin B Subunit," Proc. Natl. Acad. Sci. 91:8994-8998.

Marsh et al. (2000). "Expanded Polyglutamine Peptides Alone are Intrinsically Cytotoxic and Cause Neurodegeneration in Drosophilia," Hum. Mol. Genet. 9:13-25.

Mazmanian, S. K. et al. (Jul. 30, 1999). "*Staphylococcus aureus* Sortase, an Enzyme that Anchors Surface Proteins to the Cell Wall," Science, 285:760-763.

Mazmanian, S. K. et al. (May 9, 2000) "*Staphylococcus aureus* Sortase Mutants Defective in the Display of Surface Proteins and in the Pathogenesis of Animal Infections,"Proc. Natl. Acad. Sci. 97(10):5510-5515.

McCafferty et al. (1990). "Phage Antibodies: Filamentous Phage Displaying Antibody Variable Domains," Nature 348:552-554.

McConnell et al. (1994). "Constrained Peptide Libraries as a Tool for Finding Mimotopes," Gene 151:115-118.

McElveen, J.E. (1998). "Primary Sequence and Molecular Model of the Variable Region of a Mouse Monoclonal Anti-Der p 1 Antibody Showing a Similar Epitope Specificity as Human IgE," Clinical and Experimental Allergy 28:1427-1434.

Mennuni et al. (1997). "Identification of a Novel Type 1 Diabetes-Specific Epitope by Screening Phage Libraries with Sera from Pre-Diabetic Patients," J. Mol. Biol. 268:599-606.

Michiels, F. et al. (Nov. 2002). "Arrayed Adenoviral Expression Libraries for Functional Screening," Nature Biotechnology 20:1154-1157.

Miller, V.L. et al. (Sep. 2001). "Identification of Regions of All Required for the Invasion and Serum Resistance Phenotypes," Molecular Microbiology 41(5): 1053-1062.

Morris et al. (2000). "Translocating Peptides and Proteins and Their Use for Genen Delivery," Curr. Opinion Biotech. 11:461-466.

Morris et al. (2001). "A Peptide Carrier for the Delivery of Biologically Active Proteins into Mammalian Cells," Nature Biotech. 19:1173-1176.

Mulligan et al. (1981). "Selection for Animal Cells that Express the *Escherichia coli* Gene Coding for Xanthine-Guanine Phosphoribosyltransferase," Proc. Natl. Acad. Sci. USA 78:2072-2076.

Nedelkov, D. et al. (2001). "Analysis of Native Proteins from Biological Fluids by Biomolecular Interaction Analysis Mass Spectrometry (BIA/MS): Exploring the Limit of Detection, Identification of Non-Specific Binding and Detection of Multi-Protein Complexes," Biosensors & Bioelectronics 16:1071-1078.

Needleman et al. (1970). "A General Method Applicable to the Search for Similaritiesin the Amino Acid Sequence of Two Proteins," J. Mol. Biol. 48:443-453.

Neidigh et al. (2002). "Designing a 20-Residue Protein," Nature Structural Biology 9:425-430.

Nelson, K.E. et al. (Oct. 2000). "Status of Genome Projects for Nonpathogenic Bacteria and Archaea," Nature Biotechnology 18:1049-1054.

Nelson R.W. et al. (2000). "Biosensor Chip Mass Spectrometry: A Chip-Based Proteomics Approach," Electrophoresis 21: 1155-1163.

Nelson, R.W. et al. (1999). "BIA/MS of Epitope-Tagged Peptides Directly from *E.Coli* Lysate: Multiplex Detection and Protein Identification at Low-Fermtomole to Subfemtomole Levels," Anal. Chem. 71:2858-2865.

Nemoto N. et al. (1999). "Fluorescence Labeling of the C-Terminus of Proteins with a Puromycin Analogue in Cell-Free Translation Systems," FEBS Letters 462:43-46.

Ness et al. (2002). "Synthetic Shuffling Expands Functional Protein Diversity by Allowing Amino Acids to Recombine Independently," Nature Biotechnology 20:1251-1255.

Norman et al. (1999). "Genetic Selection of Peptide Inhibitors of Biological Pathways," Science 285:591-595.

Oefner, P.J. et al. (1996). "Efficient Random Subcloning of DNA Sheared in a Recirculating Point-Sink Flow System," Nucleic Acids Research 24(20):3879-3886.

O'Hare et al. (1981). "Transformation of Mouse Fibroblasts to Methotrexate Resistance by a Recombinant Plasmid Expressing a Prokaryotic Dihydrofolate Reductase," Proc. Natl. Acad. Sci. USA 78:1527-1531.

Palzkill et al. (1998). "Mapping Protein-Ligand Interactions Using Whole Genome Phage Display Libraries," Gene 221:79-83.

Pande et al. (1994). "Nonrandomness in Protein Sequences: Evidence for a Physically Driven Stage of Evolution?" Proc. Natl. Acad. Sci. USA 91:12972-12975.

Pavlickova, P. et al. (2003). "Microarray of Recombinant Antibodies Using a Streptavidin Sensor Surface Self-Assembled onto a Gold Layer," BioTechniques 34(1):124-130.

Phelan et al. (May 1998). "Intercellular Delivery of Functional p53 by the Herpes Virus Protein VP22," Nature Biotechnol. 16:440-443.

Pincus et al. (1998). "Peptides that Mimic the Group B Streptococcal Type III Capsular Polysaccharide Antigen," J. Immunol 160:293-298.

Pini et al. (Aug. 21, 1998). "Design and Use of a Phage Display Library," J. Biol. Chem. 21769-21776.

Postier, B.L. et al. (2003). "The Construction and Use of Bacterial DNA Microarrays Based on an Optimized Two-Stage PCR Strategy," BMC Genomics, vol. 4, 11 pages.

Raivich, G. et al., (2006). "Role of the AP-1 Transcription Factor c-Jun in Developing, Adult and Injured Brain," Progress in Neurobiology. 78:347-363.

Read et al. (2001). "Finding Drug Targbets in Microbial Genomes," Drug Disc. Today 6:887-892.

Richter et al. (2000). "Refolding, Purification, and Characterization of Human Recombinant pde4a Constructs Expressed in *Escherichia coli*," Protein Expression and Purification 19:375-383.

Robben et al. (2002). "Selection and Identification of Dense Granule Antigen GRA3 by Toxoplasma gindii Whole Genome Phage Display," J. Biol. Chem. 277:17544-17547.

Roberts et al. (1997). "RNA-Peptide Fusions for the in vitro Selection of Peptides and Proteins," Proc. Natl. Acad. Sci. USA 94:12297-12302.

Rogers et al. (1997). "Behavioral and Functional Analysis of Mouse Phenotype: SHIRPA, a Proposed Protocol for Comprehensive Phenotype Assessment," Mamm. Genome 8:711-713.

(56) References Cited

OTHER PUBLICATIONS

Rohrer, S. et al. (Aug. 1999). ":The Essential *Staphylococcus aureus* Gene fmhB is Involved in the First Step of Peptidoglycan Pentaglycine Interpeptide Formation," Proc. Natl. Acad. Sci. USA, 96: 9351-9356.
Rosenthal, P. J. et al. (Jul. 1996). "Antimalarial Effects of Vinyl Sulfone Cysteine Proteinase Inhibitors," Antimicrobial Agents and Chemotherapy 40(7): 1600-1603.
Sali, A., et al. (1993). "Comparative Protein Modelling by Satisfaction of Spatial Restraints," J. Mol. Biol. 234, 779-815.
Sambook et al. (1989). Chapters 12.2 in Molecular Cloning: A Laboratory Manual Second Edition. Cold Spring Harbor Laboratory Press, USA.
Santerre et al. (1984). "Expression of Prokaryotic Geneees for Hygromycin B and G418 Resistance as Dominant-Selection Markers in Mouse L Cells," Gene 30:147-156.
Satyal et al. (2000). "Polyglutamine Aggregates Alter Protein Folding Homeostatis in *Caenorhabditis elegans*," Proc. Natl. Acad. Sci. USA 97:5750-5755.
Shafikhani et al. (1997). "Generation of Large Libraries of Random Mutants in *Bacillus subtilis* by PCR-based Plasmid Multimerization," BioTechniques 23:304-310.
Shimatake et al. (1981). "Purified λ Regulatory Protein cII Positively Activates Promoters for Lysogenic Development," Nature 292:128-132.
Sieber et al. (2001). "Libraries of Hybrid Proteins from Distantly Related Sequences," Nature Biotechnology 19:456-460.
Soares, M.B. (1997). "Identification and Cloning of Differentially Expressed Genes," Curr. Opinion Biotechnol. 8:542-546.
Stengelin et al. (1988). "Isolation of cDNAs for Two Distinct Human Fc Receptors by Ligand Affinity Cloning," EMBO Journal 7:1053-1059.
Stranden, A.M. et al. (Jan. 1997). "Cell Wall Monoglycine Cross-Bridges and Mathicillin Hypersusceptibility in a femAB Null Mutant of Methicillin-Resistant *Staphylococcus aureus*," Journal of Bacteriology 179(1): 9-16.
Studier et al. (1986). "Use of Bacteriophage T7 RNA Polymerase to Direct Selective High-Level Expression of Cloned Genes," J. Mol. Biol. 189:113-130.
Sugita et al. "Combined Use of Oligonucleotide and Tissue Microarrays Identifies Cancer/Testis Antigens as Biomarkers in Lung Carcinoma," Cancer Res 62:3971-3979.
Supplementary Partial European Search Report for EP Application No. 04712970.5 mailed Apr. 26, 2006, five pages.
Supplementary Partial European Search Report for EP Application No. 04712970.5 mailed Aug. 3, 2006, seven pages.
Theiss, H.D. et al. (2003). "Enhancement of Gene Transfer With Recombinant Adeno-Associated Virus (rAAV) Vectors into Primary B-Cell Chronic Lymphocytic Leukemia Cells by CpG-oligodeoxynucleotides," Experimental Hematology 31:1223-1229.
Thomas et al. (1990). "Expression in *Escherichia coli* of a High-Molecular-Weight Protective Surface Antigen Found in Nontypeable and Type B *Haemophilus influenzae*," Infect. & Immun. 58:1909-1913.
Thumm, G. et al. (1997). "Studies on Prolysostaphin Processing and Characterization of the Lysostaphin Immunity Factor (Lif) of *Staphylococcus simulans* Biovar Staphylolyticus," Molecular Microbiology 23(6):1251-1265.
Tiozzo, E. et al. (1998). "Wide-Spectrum Antibiotic Activity of Synthetic, Amphipathic Peptides," Biochem. & Biophys. Res. Comm. 249(1):202-206.
Tokmakov et al. (1997) "Inhibition of MAPK Pathway by a Synthetic Peptide Corresponding to the Activation Segment of MAPK," Biochem. Biophys. Res. Comm. 252:214-219.
Tokmakov et al. (1997)."Phosphorylation-Sensitive Secondary Structure in a Synthetic Peptide Corresponding to the Activation Loop of MAP Kinase," Biochem. Biophys. Res. Commun. 236:243-247.
Tortosa, P. et al (Mar. 2000). "Characterisation of ylbF, a New Gene Involved in Competence Development and Sporulation in *Bacillus subtilis*," Molecular Microbiology 35(5) :1110-1119.
Tripet et al. (1997). "Demonstration of Coiled-Coli Interactions Within the Kinesin Neck Region Using Synthetic Peptides," J. Biol. Chem. 272:8946-8956.
Urbanek, M. et al. (Jan. 2003). "Variation in Resistin Gene Promoter Not Associated With Polycystic Ovary Syndrome," Diabetes 52: 214-217.
Valentini, S.R. et al (Feb. 1994). "Glucocorticoid-Regulated Gene in Transformed to Normal Phenotypic Reversion," Brazilian J Med Biol Res 27(2): 541-546.
Van Regenmortel M.H.V. (1989). "Structural and Functional Approaches to the Study of Protein Antigenicity," Immunology Today 10:266-272.
Vidal et al. (1999). "Yeast Forward and Reverse 'n'-hybrid Systems," Nucl. Acids Res. 27:919-929.
Vranken et al. (2002). "Solution Structures of a 30-Residue Amino-Terminal Domain of the Carp Granulin-1 Protein and its Amino-Terminally Truncated 3-30 Subfragment: Implications for the Conformational Stability of the Stack of Two β-Hairpins," Proteins 47:14-24.
Wang et al. (2004). "Predicting protein secondary structure by a support vector machine based on a new coding scheme," Genome Informatics 15(2)181-190.
Wang et al (2005). "PISCES: recent improvements to a PDP sequence culling server," Nucleic Acids Research 33:W94-W98.
Wigler et al. (1980). "Transformation of Mammalian Cells with an Amplifiable Dominant-Acting Gene," Proc. Natl. Acad. Sci. USA 77:3567-3570.
Wittrup, K.D. (2001). "Protein Engineering by Cell-Surface Display," Current Opinion in Biotechnology 12:395-399.
Wong, et al. (1996). "Use of Tagged Random Hexamer Amplification (TRHA) to Clone and Sequence Minute Quantities of DNA-Application to a 180 kb Plasmid Isolated From Sphingomonas F199," Nucleic Acids. Res. 24:3778-3783.
Xu et al. (2001). "Dominant Effector Genetics in Mammalian Cells," Nature Genetics 27:23-29.
Xu et al. (Nov. 1997). "Cells That Register Logical Relationships Among Proteins," Proc. Natl. Acad. Sci. USA 94:12473-12478.
Yang (1999). "Cloning, Expression, and Characterization of a DNA Binding Domain of gpNul, a Phage λ DNA Packaging Protein," Biochem. 38:465-477.
Yang et al. (1998). "A 20-Kilodalton N-Terminal Fragment of the D15 Protein Contains a Protective Epitope(s) Against *Haemophilus influenzae* Type A and Type B," Infect. and Immun. 66:3349-3354.
Yang et al. (2000). "An Integrated Approach to the Analysis and Modeling of Protein Sequences and Structures. III. A Comparative Study of Sequence Conservation in Protein Structural Families using Multiple Structural Alignments," J. Mol. Biol. 301:691-711.
Yang, P. et al (Dec. 17, 1999). "Direct Activation of the Fission Yeast PAK Shk1 by the Novel SH3 Domain Protein, Skb5," The Journal of Biological Chemistry 274(51): 36052-36057.
Yao, S. et al. (1998). "Uncoiling c-Jun Coiled Coils: Inhibitory Effects of Truncated Fos Peptides on Jun Dimerization and DNA binding In Vitro," Biopolymers 47(4):277-283.
Yao, S.Q. et al. (1997). "Inhibiting Dimerization and DNA Binding of c-Jun," In Peptides: Frontiers of Peptide Science, Proceedings of the 15th Amernican Peptide Symposium, Nashville, TN, Jun. 14-19, 1997, TAM, J.P. et al. eds. Kluwer Academic Publishers, Dordrecht, Netherlands, pp. 751-752.
Yasueda et al. (1996). "Species-Specific Measurement of the Second Group of Dermatophagoides Mite Allergens, Der p 2 and Der f 2, Using a Monoclonal Antibody-based ELISA," Clin. Exp. Allergy. 26:171-177.
Young, K.H. (1998). "Yeast Two-Hybrid: So Many Interactions, (in) so Little Time," Biology of Reproduction 58:302-311.
Zhang et al. (1992). "Whole Genome Amplification From a Single Cell: Implications for Genetic Analysis," Proc. Natl. Acad. Sci. USA 89:5847-5851.

(56) References Cited

OTHER PUBLICATIONS

Zhou, J.M. et al. (2002). "A Novel Strategy by the Action of Ricin that Connects Phenotype and Genotype Without Loss of the Diversity of Libraries," J. Am. Chem. Soc. 124(4):538-543.

Zhou, X-F. et al. (Feb. 1999). "Ligand-Activated Retinoic Acid Receptor Inhibits AP-1 Transactivation by Disrupting c-Jun/c-Fos Dimerization," Mol. Endocrin. 13(2):276-285.

Hess, J. et al., "AP-1 Subunits: Quarrel and Harmony Among Siblings," Journal of Cell Science, 2004, pp. 5965-5973, vol. 117, No. 25.

Vives, E. et al., "A Truncated HIV-1 Tat Protein Basic Domain Rapidly Translocates Through the Plasma Membrane and Accumulates in the Cell Nucleus," The Journal of Biological Chemistry, Jun. 20, 1997, pp. 16010-16017, vol. 272, No. 25.

* cited by examiner

SEQUENCE LISTING

<160> NUMBER OF SEQ ID NOS: 168

<210> SEQ ID NO 1
<211> LENGTH: 419
<212> TYPE: DNA
<213> ORGANISM: artificial
<220> FEATURE:
<223> OTHER INFORMATION: DNA encoding FLAG-PYC4 peptide
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (392)..(392)
<223> OTHER INFORMATION: n is a, c, g, or t
<220> FEATURE:
<221> NAME/KEY: misc_feature

```
<222> LOCATION: (394)..(394)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (403)..(404)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t

<400> SEQUENCE: 1 gggagaccen ngcttggtac cnngctcgga tccngtatgg gtaagcctat ccctaaccct      60
ctcctcggtc tcgattctac acaagctatg ggtgctcctc caaaaaagaa gagaaaggta     120
gctgaattca ggtcagacta caaggacgac gacgacaagg cttatcaatc catgtgatgt     180
gaaagccgct tcctggacaa tgcatctgcc cctgccatga ggaatgcaaa gaggcgttcc     240
naagagcggg tcctgtgtaa cctgacagtt catagaaaac acattttgca caagatcacn     300
agtgatgacc tcttccggac ngcnttctgc atnaatccnt ttatcttta tggncncaag      360 atgangcgca tgattgantt ganaangntt gncntcntcn tcnntgnagt ctganctgg      419

<210> SEQ ID NO 2
<211> LENGTH: 243
<212> TYPE: DNA
<213> ORGANISM: artificial
<220> FEATURE:
<223> OTHER INFORMATION: DNA encoding FLAG-PYC6 peptide
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 2 gggagaccen ngcttggtac cnngctcgga tccagtatgg gtaagcctat ccctaaccct      60
ctcctcggtc tcgattctac acaagctatg ggtgctcctc caaaaaagaa gagaaaggta     120
gctgaattca ggtcagacta caaggacgac gacgacaagg cttatcaatc taagagactt     180
tgaagatagt gtccaattgg catgtgccac agttaaccaa cttactgcaa tcattacccg     240
tga                                                                   243

<210> SEQ ID NO 3
<211> LENGTH: 387
<212> TYPE: DNA
<213> ORGANISM: artificial
<220> FEATURE:
<223> OTHER INFORMATION: DNA encoding FLAG-PYC8 peptide

<400> SEQUENCE: 3
aggtcagact acaaggacga cgacgacaag gcttatcaat caatcatagc taatgaagag      60
```

| gagagggaga aaaattttgc atccagcaaa aaggacggat cctataccga tctcttgtga | 120 |
| aacgaatgaa aaatagctct taaatccaga tatgtgtaag aatgcctcca tgattcgtgg | 180 |
| atcagaggat tgatagacca gagcttgtcg tcgtcgtcct tgtagtctga cctggtacca | 240 |
| attgatgcat cgataccggt actagtcgga ccgcatatgc ccgggcgtac cgcggccgct | 300 |
| cgaggcatgc atctagaggg ccgcatcatg taattagtta tgtcacgctt acattcacgc | 360 |
| cctcccccca catccgctct aaccgaa | 387 |

<210> SEQ ID NO 4
<211> LENGTH: 193
<212> TYPE: DNA
<213> ORGANISM: artificial
<220> FEATURE:
<223> OTHER INFORMATION: DNA encoding FLAG-PYC12 peptide

<400> SEQUENCE: 4

| aggtcagact acaaggacga cgacgacaag gcttatcaag agtccaccaa agcgctggtg | 60 |
| gaaggtggcg cggatctgat cctgattgaa accgttcttg tcgtcgtcgt ccttgtagtc | 120 |
| tgacctggta ccaattgatg catcgatacc ggtactagtc ggaccgcata tgcccgggcg | 180 |
| taccgcggcc gct | 193 |

<210> SEQ ID NO 5
<211> LENGTH: 709
<212> TYPE: DNA
<213> ORGANISM: artificial
<220> FEATURE:
<223> OTHER INFORMATION: DNA encoding FLAG-PYC15 peptide
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 5

| gggagacccn ngcttggtac cnngctcgga tccagtatgg gtaagcctat ccctaaccct | 60 |
| ctcctcggtc tcgattctac acaagctatg ggtgctcctc aaaaaagaa gagaaaggta | 120 |
| gctgaattca ggtcagacta caaggacgac gacgacaaga cttatcaatc aatcaaaggc | 180 |
| ccagaaaata aagtgaaaat gtattttttg aatgatttaa atttctctag acgcgatgct | 240 |
| ggatttaaag caagaaaaga tgcactggac attgcttcag attatgaaaa catttctgtt | 300 |
| gttaacattc ctctatgggg tggagtagtc cagagaatta ttagttctgt taagcttagt | 360 |
| acatttctct gcggtcttga aaataaagat gttttaattt tcaatttccc gatggccaaa | 420 |
| ccattttggc atatattgtc attctttcac cgccttctaa aatttagaat agtacttctg | 480 |
| attgatgata agccttgtcg tcgtcgtcct tgcagtctga cctggtacca attgatgcat | 540 |
| cgataccggt actagtcgga ccgcatatgc ggccgctcga gcatgcatct agagggccct | 600 |
| attctatagt gtcacctaaa tgctagagct cgctgatcag cctcgactgt gccttctagt | 660 |
| tgccagccat ctgttgtttg cccctccccc gtgccttcct gaccctgg | 709 |

<210> SEQ ID NO 6
<211> LENGTH: 255
<212> TYPE: DNA
<213> ORGANISM: artificial
<220> FEATURE:
<223> OTHER INFORMATION: DNA encoding FLAG-PYC18 peptide -continued

<400> SEQUENCE: 6
agagctcgga tcagtatggg tagctatccc taaccctctc ctcggtctcg attctacaca    60
agctatgggt gctcctccaa aaaagaagag aaaggtagct gaattcaggt cagactacaa   120
ggacgacgac gacaaggctt atcaatcaat catacattga ctacaaggac gacgacgaca   180
aggcttatca atcaatcaat ggggccctgc tgaagattca acgttcttcg cctctccttg   240
cttttgaata tcttc                                                    255

<210> SEQ ID NO 7
<211> LENGTH: 244
<212> TYPE: DNA
<213> ORGANISM: artificial
<220> FEATURE:
<223> OTHER INFORMATION: DNA encoding FLAG-PYC19 peptide
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t

<400> SEQUENCE: 7
tngggagacc caagcttggt acnnngctcg gatccagtat gggtaagcct atncctaacc    60
ctctcctcgg tctcgattct acacaagcta tgggtgctcc tccaaaaaag aagagaaagg   120
tagctgaatt caggtcagac tacaaggacg acgacgacaa gcttatcaat caatcatacg   180 catacccttaa catttactaa tattggactt attttagatg tacgtttgtt attacgttgt   240
ctct                                                                244

<210> SEQ ID NO 8
<211> LENGTH: 211
<212> TYPE: DNA
<213> ORGANISM: artificial
<220> FEATURE:
<223> OTHER INFORMATION: DNA encoding FLAG-PYC20 peptide

<400> SEQUENCE: 8
aggtcagact acaaggacga cgacgacaag atttattcat caattctatg ggggacaaaa    60
tggtgcgttt tattggtaat aacaccctaa tctatagaga tggtgattga ttgataagcc   120
ttctcgtcgt cgtccttgta gtctgacctg gtaccaattg atgcatcgat accggtacta   180
gtcggaccgc atatgcccgg gcgtaccgcg g                                  211

<210> SEQ ID NO 9
<211> LENGTH: 120
<212> TYPE: DNA
<213> ORGANISM: artificial
<220> FEATURE:
<223> OTHER INFORMATION: DNA encoding FLAG-PYC21 peptide
<220> FEATURE:
<221> NAME/KEY: misc_feature
<222> LOCATION: (53)..(53)
<223> OTHER INFORMATION: n is a, c, g, or t

<400> SEQUENCE: 9
aggtcagact acaaggacga cgacgacaag atcattattt atattttcct tancatctct    60
aatagcatca aaaacatctt cgacaatatg ggtaaaatca gataactcca tcatatcaag    120

<210> SEQ ID NO 10
<211> LENGTH: 253
<212> TYPE: DNA
<213> ORGANISM: artificial
<220> FEATURE:
<223> OTHER INFORMATION: DNA encoding FLAG-PYC22 peptide
<220> FEATURE:
<221> NAME/KEY: misc_feature
<222> LOCATION: (64)..(65)
<223> OTHER INFORMATION: n is a, c, g, or t

<400> SEQUENCE: 10
ggtcgagctg atcagtatg ggtaagccta tccctaaccc tctcctcggt ctcgattcta    60
cacnnttcta tgggtgctcc tccaaaaaag aagagaaagg tagctgaatt caggtcagac   120
tacaaggacg acgacgacaa gaaggactcc atacggcggc gcggcgagaa tatttcctcg   180
caggaagtcg aggccgtcct catgtcgcat cccgaagtcg tcaatgccgc ggtctacccc   240
gtacgcggcg atc                                                      253

<210> SEQ ID NO 11
<211> LENGTH: 255
<212> TYPE: DNA
<213> ORGANISM: artificial
<220> FEATURE:
<223> OTHER INFORMATION: DNA encoding FLAG-PYC24 peptide

<400> SEQUENCE: 11
tcgagctcgg atcagtatgg gtagcctatc cctaaccctc tcctcggtct cgattctaca    60
caagctatgg gtgctcctcc aaaaagaag agaaaggtag ctgaattcag gtcagactac   120
aaggacgacg acgacaagct atatcaatca ctactcactg ctaccaaaga attgcttttt   180
gtcgcgcctg tagcaaaagc attcacatcg tgtgattgat tgataagcct tctcgtcgtc   240
gtccttgtag tctga                                                    255

<210> SEQ ID NO 12
<211> LENGTH: 247
<212> TYPE: DNA
<213> ORGANISM: artificial
<220> FEATURE:
<223> OTHER INFORMATION: DNA encoding FLAG-PYC29 peptide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (20)..(23)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 12
ggnagaccnn ncttggtacn nnnctcggat cnngtatggg taagcctatc cctaaccctc    60
tcctcggtct cgattctaca caagctatgg gtgctcctcc aaaaagaag agaaaggtag   120 ctgaattcag gtcagactac aaggacgacg acgacaagct tatcaatca atcagtgtcg   180 tcgtcgtcct tgtagtctga cctggtacca attgatgcat cgataccggt actagtcgga   240
ccgcata                                                                          247

<210> SEQ ID NO 13
<211> LENGTH: 247
<212> TYPE: DNA
<213> ORGANISM: artificial
<220> FEATURE:
<223> OTHER INFORMATION: DNA encoding FLAG-PYC30 peptide
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 13 gggagaccen ngcttggtac nnngctcgga tccngtatgg gtaagcctat ccctaaccct    60
ctcctcggtc tcgattctac acaagctatg ggtgctcctc caaaaaagaa gagaaaggta   120
gctgaattca ggtcagacta caaggacgac gacgacaaga aggactccat acggcggcgc   180
ggcgagaata tttcctcgca ggaagtcgag gccgtcctca tgtcgcatcc cgaagtcgtc   240
aatgccg                                                             247

<210> SEQ ID NO 14
<211> LENGTH: 544
<212> TYPE: DNA
<213> ORGANISM: artificial
<220> FEATURE:
<223> OTHER INFORMATION: DNA encoding FLAG-PYC32 peptide
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (379)..(379)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t
<220> FEATURE:
<221> NAME/KEY: misc_feature
<222> LOCATION: (480)..(481)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:

<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (512)..(512)
<223> OTHER INFORMATION: n is a, c, g, or t
<220> FEATURE:
<221> NAME/KEY: misc_feature
<222> LOCATION: (515)..(517)
<223> OTHER INFORMATION: n is a, c, g, or t
<220> FEATURE:
<221> NAME/KEY: misc_feature
<222> LOCATION: (520)..(520)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (539)..(539)
<223> OTHER INFORMATION: n is a, c, g, or t

<400> SEQUENCE: 14

```
gggagaccca ngcttggtac cnngctcgga tccagtatgg gtaagcctat ccctaaccct      60
ctcctcggtc tcgattctac acaagctatg ggtgctcctc caaaaaagaa gagaaaggta     120
gctgaattca ggtcagacta caaggacgac gacgacaata ccccccactc ctccgatggc     180
cacaataatc cctaaaatct cagtgttttc cccagttttt gctagaatca taggctggta     240
aattacttca gtgattcctt ctacaaagct aaacaatgat aactgattga ttgataagcc     300
ttgtcgtcgt cgtccttgta gtctgacctg gtaccaattg gtgcatcgat accggtacta     360
gtcggaccgc atatgcggnc gctcgagcat gcatctagag ggccctattc tatagtgtca     420
cctaaatgct agagctcgct gatcngcctc nactgtgcct tctanttgcc agncatctgn     480
ngtttgccct ccccgtgnct tncttgancc tngannngcn ctccnctgnc ntttnctana     540
aatg                                                                 544
```

<210> SEQ ID NO 15
<211> LENGTH: 205
<212> TYPE: DNA
<213> ORGANISM: artificial
<220> FEATURE:
<223> OTHER INFORMATION: DNA encoding FLAG-PYC33 peptide
<220> FEATURE:
<221> NAME/KEY: misc_feature
<222> LOCATION: (192)..(192)
<223> OTHER INFORMATION: n is a, c, g, or t

<400> SEQUENCE: 15

```
aggtcagact acaaggacga cgacgacaag gcttatcaat caatcaaatg gccaatgtaa      60
attgtcggtg cgccaggaaa gagcgtcggt ttgtgtttgt cgatgatttt aagtgtttcg     120
```

```
agcggatcaa acttaggaag aagaatcatt taacacctgt tacagaaggg cttgtcgtcg      180
tcgtccttgt antctgacct gaatt                                            205
```

<210> SEQ ID NO 16
<211> LENGTH: 243
<212> TYPE: DNA
<213> ORGANISM: artificial
<220> FEATURE:
<223> OTHER INFORMATION: DNA encoding FLAG-PYC34 peptide
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 16

```
gggagaccon ngcttggtac cnagctcgat ccctaaccct ctcctcggtc tcgattctac      60
acaagctatg ggtgctcctc aaaaaagaa gagaaaggta gctgaattca ggtcagacta      120
caaggacgac gacgacaagg cttatcaatc aataaaattcg tcaccagtat tgccagaaaa   180
tagtcaagaa ttatcacttc acttaaagca acacgtaaca aaatcatgaa agaatatatc    240
aaa                                                                    243
```

<210> SEQ ID NO 17
<211> LENGTH: 243
<212> TYPE: DNA
<213> ORGANISM: artificial
<220> FEATURE:
<223> OTHER INFORMATION: DNA encoding FLAG-PYC35 peptide
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (21)..(23)
<223> OTHER INFORMATION: n is a, c, g, or t

<400> SEQUENCE: 17

```
gggagaccon agcttggtac nnngctcgga tccagtatgg gtaagcctat ccctaaccct     60
ctcctcggtc tcgattctac acaagctatg ggtgctcctc aaaaaagaa gagaaaggta    120 gctgaattca ggtcagacta caaggacgac gacgacaagg cttatcaatc aatcaggtct    180
ggagggatag agtcgagttc gaaaagggaa aggtaggggt gggaatgacc ctaaggactt   240
aca                                                                    243
```

<210> SEQ ID NO 18
<211> LENGTH: 255
<212> TYPE: DNA
<213> ORGANISM: artificial
<220> FEATURE:
<223> OTHER INFORMATION: DNA encoding FLAG-PYC36 peptide

<400> SEQUENCE: 18

```
tgtcgagctc ggaccagtat gggtaagcct atccctaacc ctctcctcgg tctcgattct    60
acacaagcta tgaggtgctc ttccaaaaaa gaagagaaag gtagctgaat tcaggtcaga   120
ctacaaggac gacgacgaca aggactacaa ggacgacga cgacaaggtt atcaatcaat    180
caagccatga ttgatctccg atatatgaat tcaggtcaga ctacaaggac gactttccct   240
```

```
tggaatagac tatag                                                    255
```

```
<210> SEQ ID NO 19
<211> LENGTH: 192
<212> TYPE: DNA
<213> ORGANISM: artificial
<220> FEATURE:
<223> OTHER INFORMATION: DNA encoding FLAG-PYC38 peptide

<400> SEQUENCE: 19
ctaaccctct cctcggtctc gattctacac aagctatggg tgctcctcca aaaagaaga    60 gaaaggtagc tgaattcagg tcagactaca aggacgacga cgacaaggga ctacaaggcc   120
gccgacagcc tggccaacag cctcaaggcc gctggagtgg acgcgcgctt ccagcgcatc   180
gatagccagc cg                                                       192

<210> SEQ ID NO 20
<211> LENGTH: 243
<212> TYPE: DNA
<213> ORGANISM: artificial
<220> FEATURE:
<223> OTHER INFORMATION: DNA encoding FLAG-PYC39 peptide
<220> FEATURE:
<221> NAME/KEY: misc_feature
<222> LOCATION: (22)..(24)
<223> OTHER INFORMATION: n is a, c, g, or t

<400> SEQUENCE: 20
gggagaccca agcttggtac cnnnctcgga tccagtatgg gtaagcctat ccctaaccct    60
ctcctcggtc tcgattctac acaagctatg ggtgctcctc caaaaaagaa gagaaaggta   120
gctgaattca ggtcagacta caaggacgac gacgacaagg gactacaagg ccgccgacag   180
cctggccaac agcctcaagg ccgctggagt ggacgcgcgc ttccagcgca tcgatagcca   240
gcc                                                                 243

<210> SEQ ID NO 21
<211> LENGTH: 614
<212> TYPE: DNA
<213> ORGANISM: artificial
<220> FEATURE:
<223> OTHER INFORMATION: DNA encoding FLAG-PYC54 peptide
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (30)..(36)
<223> OTHER INFORMATION: n is a, c, g, or t
<220> FEATURE:
<221> NAME/KEY: misc_feature
<222> LOCATION: (50)..(53)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
```

<220> FEATURE:
<221> NAME/KEY: misc_feature
<222> LOCATION: (604)..(604)
<223> OTHER INFORMATION: n is a, c, g, or t

<400> SEQUENCE: 21

```
gggagaccca agcttggtac cnnnctcggn nnnnnnatgg gtaagcctan nnntaaccct    60
ctcctcggtc tcgattctac acaagctatg ggtgctcctc caaaaaagaa gagaaaggta   120
gctgaattca ggtcagacta caaggacgac gacgacaagg cttatcaatc aatcagcttg   180
gcaggctacc acggcgacac ttcgagaaca tttctagtgg gttcggtatc cgcaactgcc   240
cgaaaattag ttgaagcgac tcaagaaacg atgattgatt atacttgtcg tcgtcgtcct   300
tgtagtctga cctggtacca attgatgcat cgataccggt actagncgga ccgcatatgc   360
ggncgctcga gcatgcntct agagggcccc attctatagt gtcacctaan tgctagagct   420
cgctgatcag cctcgactgt gccttctagt tgccagccat ctgttgtttg ccctccccc    480
gtgccttcct tgaccctgga aggtgccact cccactgtcc tttcctaata aaatgaggaa   540
attgcatcgc attgtctgag taggtgtcat tctattctgg ggggtggggt ggggcaggac   600
agcnaggggg agga                                                     614
```

<210> SEQ ID NO 22
<211> LENGTH: 323
<212> TYPE: DNA
<213> ORGANISM: artificial
<220> FEATURE:
<223> OTHER INFORMATION: DNA encoding FLAG-PYC58 peptide

<400> SEQUENCE: 22

```
aggtcagact acaaggacga cgacgacaag gcttatcaat caatcatggc agtggctgcc    60
cagcagccgg tcgcgttcct ggtaggccgc cagcgtcgcc gcggtcaggt aggaatcgac   120
tccggcgatc agcaccttcg aacacccctg ttccatgagc tttgtcgtcg tcgtccttgt   180
agtctggcct ggtaccaatt gatgcatcga taccggtact agtcggaccg catatgcccg   240
ggcgtaccgc ggccgctcga ggcatgcatc tagagggccg catcatgtaa ttagttatgt   300
cacgcttaca ttcacgccct ccc                                           323
```

<210> SEQ ID NO 23
<211> LENGTH: 220
<212> TYPE: DNA
<213> ORGANISM: artificial
<220> FEATURE:
<223> OTHER INFORMATION: DNA encoding FLAG-PYC59 peptide
<220> FEATURE:
<221> NAME/KEY: misc_feature
<222> LOCATION: (189)..(189)
<223> OTHER INFORMATION: n is a, c, g, or t

<400> SEQUENCE: 23

```
gctcggatcc agtatgggta agcctatccc taaccctctc ctcggtctcg attctacaca    60
agctatgggt gctcctccaa aaagaagag aaaggtagct gaattcaggt cagactacaa    120
ggacgacgac gacaaggctt atcaatcaat cagtgtcgtc gtcgtccttg tagtctgacc   180
tggtaccant tgatgcatcg ataccggtac tagtcggacc                         220
```

<210> SEQ ID NO 24
<211> LENGTH: 253
<212> TYPE: DNA
<213> ORGANISM: artificial
<220> FEATURE:

<223> OTHER INFORMATION: DNA encoding FLAG-PYC60 peptide

<400> SEQUENCE: 24

| | | | | |
|---|---|---|---|---|
| aggtcagact | acaaggacga | cgacgacaag | gctaatcaat | tgcccaaaat acttgctgga | 60 |
| cggcttatat | ttataaagtg | ctaactgcgc | ttgattgatt | gataagcttc tcgtcgtcgt | 120 |
| ccttgtagtc | tgacctggta | ccaattgatg | catcgatacc | ggtactagtc ggaccgcata | 180 |
| tgcccgggcg | taccgcggcc | gctcgaggca | tgcatctaga | gggccgcatc atgtaattag | 240 |
| ttatgtcacg | ctt | | | | 253 |

<210> SEQ ID NO 25
<211> LENGTH: 255
<212> TYPE: DNA
<213> ORGANISM: artificial
<220> FEATURE:
<223> OTHER INFORMATION: DNA encoding FLAG-PYC66 peptide

<400> SEQUENCE: 25

| | | | | |
|---|---|---|---|---|
| gtcgagctcg | gatcagtatg | ggtagcctat | ccctaaccct | ctcctcggtc tcgattctac | 60 |
| acaagctatg | ggtgctcctc | caaaaaagaa | gagaaaggta | gctgaattca ggtcagacta | 120 |
| caaggacgac | gacgacaagg | cttatcaatc | aatcataggg | gcgggaaaat caacgctaat | 180 |
| caaagcatta | actggcgtat | accacgccga | tcgcggcacc | atctggctgg aaggccaggc | 240 |
| tatctcaccg | aaaaa | | | | 255 |

<210> SEQ ID NO 26
<211> LENGTH: 15
<212> TYPE: PRT
<213> ORGANISM: artificial
<220> FEATURE:
<223> OTHER INFORMATION: FLAG-PYC4 peptide

<400> SEQUENCE: 26

Arg Ser Asp Tyr Lys Asp Asp Asp Asp Lys Ala Tyr Gln Ser Met
1               5                   10                  15

<210> SEQ ID NO 27
<211> LENGTH: 5
<212> TYPE: PRT
<213> ORGANISM: artificial
<220> FEATURE:
<223> OTHER INFORMATION: PYC4 peptide

<400> SEQUENCE: 27

Ala Tyr Gln Ser Met
1               5

<210> SEQ ID NO 28
<211> LENGTH: 17
<212> TYPE: PRT
<213> ORGANISM: artificial
<220> FEATURE:
<223> OTHER INFORMATION: FLAG-PYC6 peptide

<400> SEQUENCE: 28

Arg Ser Asp Tyr Lys Asp Asp Asp Asp Lys Ala Tyr Gln Ser Lys Arg
1               5                   10                  15

Leu

<210> SEQ ID NO 29
<211> LENGTH: 7
<212> TYPE: PRT

```
<213> ORGANISM: artificial
<220> FEATURE:
<223> OTHER INFORMATION: PYC6 peptide

<400> SEQUENCE: 29

Ala Tyr Gln Ser Lys Arg Leu
1               5

<210> SEQ ID NO 30
<211> LENGTH: 39
<212> TYPE: PRT
<213> ORGANISM: artificial
<220> FEATURE:
<223> OTHER INFORMATION: FLAG-PYC8 peptide

<400> SEQUENCE: 30

Arg Ser Asp Tyr Lys Asp Asp Asp Lys Ala Tyr Gln Ser Ile Ile
1               5                   10                  15

Ala Asn Glu Glu Glu Arg Glu Lys Asn Phe Ala Ser Ser Lys Lys Asp
            20                  25                  30

Gly Ser Tyr Thr Asp Leu Leu
        35

<210> SEQ ID NO 31
<211> LENGTH: 29
<212> TYPE: PRT
<213> ORGANISM: artificial
<220> FEATURE:
<223> OTHER INFORMATION: PYC8 peptide

<400> SEQUENCE: 31

Ala Tyr Gln Ser Ile Ile Ala Asn Glu Glu Glu Arg Glu Lys Asn Phe
1               5                   10                  15

Ala Ser Ser Lys Lys Asp Gly Ser Tyr Thr Asp Leu Leu
            20                  25

<210> SEQ ID NO 32
<211> LENGTH: 40
<212> TYPE: PRT
<213> ORGANISM: artificial
<220> FEATURE:
<223> OTHER INFORMATION: FLAG-PYC12 peptide

<400> SEQUENCE: 32

Arg Ser Asp Tyr Lys Asp Asp Asp Lys Ala Tyr Gln Glu Ser Thr
1               5                   10                  15

Lys Ala Leu Val Glu Gly Gly Ala Asp Leu Ile Leu Ile Glu Thr Val
            20                  25                  30

Leu Val Val Val Leu Val Val
        35              40

<210> SEQ ID NO 33
<211> LENGTH: 30
<212> TYPE: PRT
<213> ORGANISM: artificial
<220> FEATURE:
<223> OTHER INFORMATION: PYC12 peptide

<400> SEQUENCE: 33

Ala Tyr Gln Glu Ser Thr Lys Ala Leu Val Glu Gly Gly Ala Asp Leu
1               5                   10                  15

Ile Leu Ile Glu Thr Val Leu Val Val Val Leu Val Val
            20                  25                  30
```

-continued

```
<210> SEQ ID NO 34
<211> LENGTH: 141
<212> TYPE: PRT
<213> ORGANISM: artificial
<220> FEATURE:
<223> OTHER INFORMATION: FLAG-PYC15 peptide

<400> SEQUENCE: 34

Arg Ser Asp Tyr Lys Asp Asp Asp Lys Thr Tyr Gln Ser Ile Lys
1               5                   10                  15

Gly Pro Glu Asn Lys Val Lys Met Tyr Phe Leu Asn Asp Leu Asn Phe
            20                  25                  30

Ser Arg Arg Asp Ala Gly Phe Lys Ala Arg Lys Asp Ala Leu Asp Ile
        35                  40                  45

Ala Ser Asp Tyr Glu Asn Ile Ser Val Val Asn Ile Pro Leu Trp Gly
    50                  55                  60

Gly Val Val Gln Arg Ile Ile Ser Ser Val Lys Leu Ser Thr Phe Leu
65                  70                  75                  80

Cys Gly Leu Glu Asn Lys Asp Val Leu Ile Phe Asn Phe Pro Met Ala
                85                  90                  95

Lys Pro Phe Trp His Ile Leu Ser Phe Phe His Arg Leu Leu Lys Phe
            100                 105                 110

Arg Ile Val Leu Leu Ile Asp Asp Lys Pro Cys Arg Arg Pro Cys
        115                 120                 125

Ser Leu Thr Trp Tyr Gln Leu Met His Arg Tyr Arg Tyr
    130                 135                 140

<210> SEQ ID NO 35
<211> LENGTH: 131
<212> TYPE: PRT
<213> ORGANISM: artificial
<220> FEATURE:
<223> OTHER INFORMATION: PYC15 peptide

<400> SEQUENCE: 35

Thr Tyr Gln Ser Ile Lys Gly Pro Glu Asn Lys Val Lys Met Tyr Phe
1               5                   10                  15

Leu Asn Asp Leu Asn Phe Ser Arg Arg Asp Ala Gly Phe Lys Ala Arg
            20                  25                  30

Lys Asp Ala Leu Asp Ile Ala Ser Asp Tyr Glu Asn Ile Ser Val Val
        35                  40                  45

Asn Ile Pro Leu Trp Gly Gly Val Val Gln Arg Ile Ile Ser Ser Val
    50                  55                  60

Lys Leu Ser Thr Phe Leu Cys Gly Leu Glu Asn Lys Asp Val Leu Ile
65                  70                  75                  80

Phe Asn Phe Pro Met Ala Lys Pro Phe Trp His Ile Leu Ser Phe Phe
                85                  90                  95

His Arg Leu Leu Lys Phe Arg Ile Val Leu Leu Ile Asp Asp Lys Pro
            100                 105                 110

Cys Arg Arg Pro Cys Ser Leu Thr Trp Tyr Gln Leu Met His Arg
        115                 120                 125

Tyr Arg Tyr
    130

<210> SEQ ID NO 36
<211> LENGTH: 17
<212> TYPE: PRT
<213> ORGANISM: artificial
```

```
<220> FEATURE:
<223> OTHER INFORMATION: FLAG-PYC18 peptide

<400> SEQUENCE: 36

Arg Ser Asp Tyr Lys Asp Asp Asp Lys Ala Tyr Gln Ser Ile Ile
1               5                   10                  15
His

<210> SEQ ID NO 37
<211> LENGTH: 7
<212> TYPE: PRT
<213> ORGANISM: artificial
<220> FEATURE:
<223> OTHER INFORMATION: PYC18 peptide

<400> SEQUENCE: 37

Ala Tyr Gln Ser Ile Ile His
1               5

<210> SEQ ID NO 38
<211> LENGTH: 22
<212> TYPE: PRT
<213> ORGANISM: artificial
<220> FEATURE:
<223> OTHER INFORMATION: FLAG-PYC19 peptide

<400> SEQUENCE: 38

Arg Ser Asp Tyr Lys Asp Asp Asp Lys Leu Ile Asn Gln Ser Tyr
1               5                   10                  15
Ala Tyr Pro Tyr Ile Tyr
            20

<210> SEQ ID NO 39
<211> LENGTH: 12
<212> TYPE: PRT
<213> ORGANISM: artificial
<220> FEATURE:
<223> OTHER INFORMATION: PYC19 peptide

<400> SEQUENCE: 39

Leu Ile Asn Gln Ser Tyr Ala Tyr Pro Tyr Ile Tyr
1               5                   10

<210> SEQ ID NO 40
<211> LENGTH: 29
<212> TYPE: PRT
<213> ORGANISM: artificial
<220> FEATURE:
<223> OTHER INFORMATION: FLAG-PYC20 peptide

<400> SEQUENCE: 40

Arg Ser Asp Tyr Lys Asp Asp Asp Lys Ile Tyr Ser Ser Ile Leu
1               5                   10                  15
Trp Gly Thr Lys Trp Cys Val Leu Leu Val Ile Thr Pro
            20                  25

<210> SEQ ID NO 41
<211> LENGTH: 19
<212> TYPE: PRT
<213> ORGANISM: artificial
<220> FEATURE:
<223> OTHER INFORMATION: PYC20 peptide

<400> SEQUENCE: 41

Ile Tyr Ser Ser Ile Leu Trp Gly Thr Lys Trp Cys Val Leu Leu Val
```

-continued

```
1               5                   10                  15

Ile Thr Pro

<210> SEQ ID NO 42
<211> LENGTH: 34
<212> TYPE: PRT
<213> ORGANISM: artificial
<220> FEATURE:
<223> OTHER INFORMATION: FLAG-PYC21 peptide

<400> SEQUENCE: 42

Arg Ser Asp Tyr Lys Asp Asp Asp Lys Ile Ile Ile Tyr Ile Phe
1               5                   10                  15

Leu Asn Ile Ser Asn Ser Ile Lys Asn Ile Phe Asp Asn Met Gly Lys
            20                  25                  30

Ile Arg

<210> SEQ ID NO 43
<211> LENGTH: 24
<212> TYPE: PRT
<213> ORGANISM: artificial
<220> FEATURE:
<223> OTHER INFORMATION: PYC21 peptide

<400> SEQUENCE: 43

Ile Ile Ile Tyr Ile Phe Leu Asn Ile Ser Asn Ser Lys Asn Ile
1               5                   10                  15

Phe Asp Asn Met Gly Lys Ile Arg
            20

<210> SEQ ID NO 44
<211> LENGTH: 51
<212> TYPE: PRT
<213> ORGANISM: artificial
<220> FEATURE:
<223> OTHER INFORMATION: FLAG-PYC22 peptide

<400> SEQUENCE: 44

Arg Ser Asp Tyr Lys Asp Asp Asp Lys Lys Asp Ser Ile Arg Arg
1               5                   10                  15

Arg Gly Glu Asn Ile Ser Ser Gln Glu Val Glu Ala Val Leu Met Ser
            20                  25                  30

His Pro Glu Val Val Asn Ala Ala Val Tyr Pro Val Arg Gly Asp Leu
            35                  40                  45

Pro Gly Asp
    50

<210> SEQ ID NO 45
<211> LENGTH: 41
<212> TYPE: PRT
<213> ORGANISM: artificial
<220> FEATURE:
<223> OTHER INFORMATION: PYC22 peptide

<400> SEQUENCE: 45

Lys Asp Ser Ile Arg Arg Arg Gly Glu Asn Ile Ser Ser Gln Glu Val
1               5                   10                  15

Glu Ala Val Leu Met Ser His Pro Glu Val Val Asn Ala Ala Val Tyr
            20                  25                  30

Pro Val Arg Gly Asp Leu Pro Gly Asp
            35                  40
```

-continued

```
<210> SEQ ID NO 46
<211> LENGTH: 36
<212> TYPE: PRT
<213> ORGANISM: artificial
<220> FEATURE:
<223> OTHER INFORMATION: FLAG-PYC24 peptide

<400> SEQUENCE: 46

Arg Ser Asp Tyr Lys Asp Asp Asp Lys Leu Tyr Gln Ser Leu Leu
1               5                   10                  15

Thr Ala Thr Lys Glu Leu Leu Phe Val Ala Pro Val Ala Lys Ala Phe
            20                  25                  30

Thr Ser Cys Asp
        35

<210> SEQ ID NO 47
<211> LENGTH: 26
<212> TYPE: PRT
<213> ORGANISM: artificial
<220> FEATURE:
<223> OTHER INFORMATION: PYC24 peptide

<400> SEQUENCE: 47

Leu Tyr Gln Ser Leu Leu Thr Ala Thr Lys Glu Leu Leu Phe Val Ala
1               5                   10                  15

Pro Val Ala Lys Ala Phe Thr Ser Cys Asp
            20                  25

<210> SEQ ID NO 48
<211> LENGTH: 20
<212> TYPE: PRT
<213> ORGANISM: artificial
<220> FEATURE:
<223> OTHER INFORMATION: FLAG-PYC29 peptide

<400> SEQUENCE: 48

Arg Ser Asp Tyr Lys Asp Asp Asp Lys Ala Tyr Gln Ser Ile Ser
1               5                   10                  15

Phe Leu Ser Gln
            20

<210> SEQ ID NO 49
<211> LENGTH: 10
<212> TYPE: PRT
<213> ORGANISM: artificial
<220> FEATURE:
<223> OTHER INFORMATION: PYC29 peptide

<400> SEQUENCE: 49

Ala Tyr Gln Ser Ile Ser Phe Leu Ser Gln
1               5                   10

<210> SEQ ID NO 50
<211> LENGTH: 51
<212> TYPE: PRT
<213> ORGANISM: artificial
<220> FEATURE:
<223> OTHER INFORMATION: FLAG-PYC30 peptide

<400> SEQUENCE: 50

Arg Ser Asp Tyr Lys Asp Asp Asp Lys Lys Asp Ser Ile Arg Arg
1               5                   10                  15

Arg Gly Glu Asn Ile Ser Ser Gln Glu Val Glu Ala Val Leu Met Ser
            20                  25                  30
```

His Pro Glu Val Val Asn Ala Ala Val Tyr Pro Val Arg Gly Asp Leu
            35                  40                  45

Pro Gly Asp
    50

<210> SEQ ID NO 51
<211> LENGTH: 41
<212> TYPE: PRT
<213> ORGANISM: artificial
<220> FEATURE:
<223> OTHER INFORMATION: PYC30 peptide

<400> SEQUENCE: 51

Lys Asp Ser Ile Arg Arg Arg Gly Glu Asn Ile Ser Ser Gln Glu Val
1               5                   10                  15

Glu Ala Val Leu Met Ser His Pro Glu Val Val Asn Ala Ala Val Tyr
            20                  25                  30

Pro Val Arg Gly Asp Leu Pro Gly Asp
            35                  40

<210> SEQ ID NO 52
<211> LENGTH: 21
<212> TYPE: PRT
<213> ORGANISM: artificial
<220> FEATURE:
<223> OTHER INFORMATION: FLAG-PYC32 peptide

<400> SEQUENCE: 52

Arg Ser Asp Tyr Lys Asp Asp Asp Asp Asn Thr Pro His Ser Ser Asp
1               5                   10                  15

Gly His Asn Asn Pro
            20

<210> SEQ ID NO 53
<211> LENGTH: 12
<212> TYPE: PRT
<213> ORGANISM: artificial
<220> FEATURE:
<223> OTHER INFORMATION: PYC32 peptide

<400> SEQUENCE: 53

Asn Thr Pro His Ser Ser Asp Gly His Asn Asn Pro
1               5                   10

<210> SEQ ID NO 54
<211> LENGTH: 39
<212> TYPE: PRT
<213> ORGANISM: artificial
<220> FEATURE:
<223> OTHER INFORMATION: FLAG-PYC34 peptide

<400> SEQUENCE: 54

Arg Ser Asp Tyr Lys Asp Asp Asp Asp Lys Ala Tyr Gln Ser Ile Asn
1               5                   10                  15

Ser Ser Pro Val Leu Pro Glu Asn Ser Gln Glu Leu Ser Leu His Leu
            20                  25                  30

Lys Gln His Val Thr Lys Ser
            35

<210> SEQ ID NO 55
<211> LENGTH: 29
<212> TYPE: PRT
<213> ORGANISM: artificial

```
<220> FEATURE:
<223> OTHER INFORMATION: PYC34 peptide

<400> SEQUENCE: 55

Ala Tyr Gln Ser Ile Asn Ser Ser Pro Val Leu Pro Glu Asn Ser Gln
1               5                   10                  15

Glu Leu Ser Leu His Leu Lys Gln His Val Thr Lys Ser
            20                  25

<210> SEQ ID NO 56
<211> LENGTH: 28
<212> TYPE: PRT
<213> ORGANISM: artificial
<220> FEATURE:
<223> OTHER INFORMATION: FLAG-PYC35 peptide

<400> SEQUENCE: 56

Arg Ser Asp Tyr Lys Asp Asp Asp Lys Ala Tyr Gln Ser Ile Arg
1               5                   10                  15

Ser Gly Gly Ile Glu Ser Ser Ser Lys Arg Glu Arg
            20                  25

<210> SEQ ID NO 57
<211> LENGTH: 18
<212> TYPE: PRT
<213> ORGANISM: artificial
<220> FEATURE:
<223> OTHER INFORMATION: PYC35 peptide

<400> SEQUENCE: 57

Ala Tyr Gln Ser Ile Arg Ser Gly Gly Ile Glu Ser Ser Ser Lys Arg
1               5                   10                  15

Glu Arg

<210> SEQ ID NO 58
<211> LENGTH: 25
<212> TYPE: PRT
<213> ORGANISM: artificial
<220> FEATURE:
<223> OTHER INFORMATION: FLAG-PYC36 peptide

<400> SEQUENCE: 58

Arg Ser Asp Tyr Lys Asp Asp Asp Lys Gly Leu Gln Gly Arg Arg
1               5                   10                  15

Arg Gln Gly Tyr Gln Ser Ile Lys Pro
            20                  25

<210> SEQ ID NO 59
<211> LENGTH: 15
<212> TYPE: PRT
<213> ORGANISM: artificial
<220> FEATURE:
<223> OTHER INFORMATION: PYC36 peptide

<400> SEQUENCE: 59

Gly Leu Gln Gly Arg Arg Arg Gln Gly Tyr Gln Ser Ile Lys Pro
1               5                   10                  15

<210> SEQ ID NO 60
<211> LENGTH: 35
<212> TYPE: PRT
<213> ORGANISM: artificial
<220> FEATURE:
<223> OTHER INFORMATION: FLAG-PYC38 peptide
```

-continued

```
<400> SEQUENCE: 60

Arg Ser Asp Tyr Lys Asp Asp Asp Lys Gly Leu Gln Gly Arg Arg
1               5                   10                  15

Gln Pro Gly Gln Gln Pro Gln Gly Arg Trp Ser Gly Arg Ala Leu Pro
                20                  25                  30

Ala His Arg
        35

<210> SEQ ID NO 61
<211> LENGTH: 25
<212> TYPE: PRT
<213> ORGANISM: artificial
<220> FEATURE:
<223> OTHER INFORMATION: FLAG-PYC38 peptide

<400> SEQUENCE: 61

Gly Leu Gln Gly Arg Arg Gln Pro Gly Gln Gln Pro Gln Gly Arg Trp
1               5                   10                  15

Ser Gly Arg Ala Leu Pro Ala His Arg
                20                  25

<210> SEQ ID NO 62
<211> LENGTH: 35
<212> TYPE: PRT
<213> ORGANISM: artificial
<220> FEATURE:
<223> OTHER INFORMATION: FLAG-PYC39 peptide

<400> SEQUENCE: 62

Arg Ser Asp Tyr Lys Asp Asp Asp Lys Gly Leu Gln Gly Arg Arg
1               5                   10                  15

Gln Pro Gly Gln Gln Pro Gln Gly Arg Trp Ser Gly Arg Ala Leu Pro
                20                  25                  30

Ala His Arg
        35

<210> SEQ ID NO 63
<211> LENGTH: 25
<212> TYPE: PRT
<213> ORGANISM: artificial
<220> FEATURE:
<223> OTHER INFORMATION: PYC39 peptide

<400> SEQUENCE: 63

Gly Leu Gln Gly Arg Arg Gln Pro Gly Gln Gln Pro Gln Gly Arg Trp
1               5                   10                  15

Ser Gly Arg Ala Leu Pro Ala His Arg
                20                  25

<210> SEQ ID NO 64
<211> LENGTH: 71
<212> TYPE: PRT
<213> ORGANISM: artificial
<220> FEATURE:
<223> OTHER INFORMATION: FLAG-PYC54 peptide

<400> SEQUENCE: 64

Arg Ser Asp Tyr Lys Asp Asp Asp Lys Ala Tyr Gln Ser Ile Ser
1               5                   10                  15

Leu Ala Gly Tyr His Gly Asp Thr Ser Arg Thr Phe Leu Val Gly Ser
                20                  25                  30

Val Ser Ala Thr Ala Arg Lys Leu Val Glu Ala Thr Gln Glu Thr Met
```

```
                    35                  40                  45
Ile Asp Tyr Thr Cys Arg Arg Pro Cys Ser Leu Thr Trp Tyr Gln
 50                  55                  60

Leu Met His Arg Tyr Arg Tyr
 65                  70

<210> SEQ ID NO 65
<211> LENGTH: 61
<212> TYPE: PRT
<213> ORGANISM: artificial
<220> FEATURE:
<223> OTHER INFORMATION: PYC54 peptide

<400> SEQUENCE: 65

Ala Tyr Gln Ser Ile Ser Leu Ala Gly Tyr His Gly Asp Thr Ser Arg
 1               5                  10                  15

Thr Phe Leu Val Gly Ser Val Ser Ala Thr Ala Arg Lys Leu Val Glu
                20                  25                  30

Ala Thr Gln Glu Thr Met Ile Asp Tyr Thr Cys Arg Arg Pro Cys
             35                  40                  45

Ser Leu Thr Trp Tyr Gln Leu Met His Arg Tyr Arg Tyr
 50                  55                  60

<210> SEQ ID NO 66
<211> LENGTH: 73
<212> TYPE: PRT
<213> ORGANISM: artificial
<220> FEATURE:
<223> OTHER INFORMATION: FLAG-PYC58 peptide

<400> SEQUENCE: 66

Arg Ser Asp Tyr Lys Asp Asp Asp Lys Ala Tyr Gln Ser Ile Met
 1               5                  10                  15

Ala Val Ala Ala Gln Gln Pro Val Ala Phe Leu Val Gly Arg Gln Arg
                20                  25                  30

Arg Arg Gly Gln Val Gly Ile Asp Ser Gly Asp Gln His Leu Arg Thr
             35                  40                  45

Pro Leu Phe His Glu Leu Cys Arg Arg Pro Cys Ser Leu Ala Trp
 50                  55                  60

Tyr Gln Leu Met His Arg Tyr Arg Tyr
 65                  70

<210> SEQ ID NO 67
<211> LENGTH: 63
<212> TYPE: PRT
<213> ORGANISM: artificial
<220> FEATURE:
<223> OTHER INFORMATION: PYC58 peptide

<400> SEQUENCE: 67

Ala Tyr Gln Ser Ile Met Ala Val Ala Ala Gln Gln Pro Val Ala Phe
 1               5                  10                  15

Leu Val Gly Arg Gln Arg Arg Gly Gln Val Gly Ile Asp Ser Gly
                20                  25                  30

Asp Gln His Leu Arg Thr Pro Leu Phe His Glu Leu Cys Arg Arg Arg
             35                  40                  45

Pro Cys Ser Leu Ala Trp Tyr Gln Leu Met His Arg Tyr Arg Tyr
 50                  55                  60

<210> SEQ ID NO 68
```

-continued

```
<211> LENGTH: 23
<212> TYPE: PRT
<213> ORGANISM: artificial
<220> FEATURE:
<223> OTHER INFORMATION: FLAG-PYC59 peptide

<400> SEQUENCE: 68

Arg Ser Asp Tyr Lys Asp Asp Asp Lys Ala Tyr Gln Ser Ile Ser
1               5                   10                  15

Val Val Val Val Leu Val Val
            20

<210> SEQ ID NO 69
<211> LENGTH: 13
<212> TYPE: PRT
<213> ORGANISM: artificial
<220> FEATURE:
<223> OTHER INFORMATION: PYC59 peptide

<400> SEQUENCE: 69

Ala Tyr Gln Ser Ile Ser Val Val Val Leu Val Val
1               5                   10

<210> SEQ ID NO 70
<211> LENGTH: 27
<212> TYPE: PRT
<213> ORGANISM: artificial
<220> FEATURE:
<223> OTHER INFORMATION: FLAG-PYC60 peptide

<400> SEQUENCE: 70

Arg Ser Asp Tyr Lys Asp Asp Asp Lys Ala Asn Gln Leu Pro Lys
1               5                   10                  15

Ile Leu Ala Gly Arg Leu Ile Phe Ile Lys Cys
            20                  25

<210> SEQ ID NO 71
<211> LENGTH: 17
<212> TYPE: PRT
<213> ORGANISM: artificial
<220> FEATURE:
<223> OTHER INFORMATION: PYC60 peptide

<400> SEQUENCE: 71

Ala Asn Gln Leu Pro Lys Ile Leu Ala Gly Arg Leu Ile Phe Ile Lys
1               5                   10                  15

Cys

<210> SEQ ID NO 72
<211> LENGTH: 74
<212> TYPE: PRT
<213> ORGANISM: artificial
<220> FEATURE:
<223> OTHER INFORMATION: FLAG-PYC66 peptide

<400> SEQUENCE: 72

Arg Ser Asp Tyr Lys Asp Asp Asp Lys Ala Tyr Gln Ser Ile Ile
1               5                   10                  15

Gly Ala Gly Lys Ser Thr Leu Ile Lys Ala Leu Thr Gly Val Tyr His
            20                  25                  30

Ala Asp Arg Gly Thr Ile Trp Leu Glu Gly Gln Ala Ile Ser Pro Lys
        35                  40                  45

Asn Thr Ala His Ala Gln Gln Cys Arg Arg Arg Pro Cys Ser Leu Thr
    50                  55                  60
```

```
Trp Tyr Gln Leu Met His Arg Tyr Arg Tyr
 65                  70
```

<210> SEQ ID NO 73
<211> LENGTH: 5
<212> TYPE: PRT
<213> ORGANISM: artificial
<220> FEATURE:
<223> OTHER INFORMATION: PYC4D peptide (the retroinverted form of PYC4
      peptide all amino acids other than glycine are D-amino acids)

<400> SEQUENCE: 73

```
Met Ser Gln Tyr Ala
1               5
```

<210> SEQ ID NO 74
<211> LENGTH: 16
<212> TYPE: PRT
<213> ORGANISM: artificial
<220> FEATURE:
<223> OTHER INFORMATION: PYC4D-TAT peptide (the retroinverted form of
      PYC4 peptide comprising an N-terminal tat basic region protein
      transduction domain wherein all amino acids other than glycine are
      D-amino acids)

<400> SEQUENCE: 74

```
Met Ser Gln Tyr Ala Gly Arg Arg Arg Gln Arg Arg Lys Lys Arg Gly
1               5                  10                  15
```

<210> SEQ ID NO 75
<211> LENGTH: 7
<212> TYPE: PRT
<213> ORGANISM: artificial
<220> FEATURE:
<223> OTHER INFORMATION: PYC6D peptide (the retroinverted form of PYC4
      peptide all amino acids other than glycine are D-amino acids)

<400> SEQUENCE: 75

```
Leu Arg Lys Ser Gln Tyr Ala
1               5
```

<210> SEQ ID NO 76
<211> LENGTH: 18
<212> TYPE: PRT
<213> ORGANISM: artificial
<220> FEATURE:
<223> OTHER INFORMATION: PYC6D-TAT peptide (the retroinverted form of
      PYC6 peptide comprising an N-terminal tat basic region protein
      transduction domain wherein all amino acids other than glycine are
      D-amino acids)

<400> SEQUENCE: 76

```
Leu Arg Lys Ser Gln Tyr Ala Gly Arg Arg Arg Gln Arg Arg Lys Lys
1               5                  10                  15

Arg Gly
```

<210> SEQ ID NO 77
<211> LENGTH: 29
<212> TYPE: PRT
<213> ORGANISM: artificial
<220> FEATURE:
<223> OTHER INFORMATION: PYC8D peptide (the retroinverted form of PYC8
      peptide all amino acids other than glycine are D-amino acids)

<400> SEQUENCE: 77

```
Leu Leu Asp Thr Tyr Ser Gly Asp Lys Lys Ser Ser Ala Phe Asn Lys
1               5                  10                  15
```

```
Glu Arg Glu Glu Glu Asn Ala Ile Ile Ser Gln Tyr Ala
            20                  25
```

<210> SEQ ID NO 78
<211> LENGTH: 40
<212> TYPE: PRT
<213> ORGANISM: artificial
<220> FEATURE:
<223> OTHER INFORMATION: PYC8D-TAT peptide (the retroinverted form of
      PYC8 peptide comprising an N-terminal tat basic region protein
      transduction domain wherein all amino acids other than glycine are
      D-amino acids)

<400> SEQUENCE: 78

```
Leu Leu Asp Thr Tyr Ser Gly Asp Lys Lys Ser Ser Ala Phe Asn Lys
1               5                   10                  15

Glu Arg Glu Glu Glu Asn Ala Ile Ile Ser Gln Tyr Ala Gly Arg Arg
            20                  25                  30

Arg Gln Arg Arg Lys Lys Arg Gly
        35                  40
```

<210> SEQ ID NO 79
<211> LENGTH: 30
<212> TYPE: PRT
<213> ORGANISM: artificial
<220> FEATURE:
<223> OTHER INFORMATION: PYC12D peptide (the retroinverted form of PYC12
      peptide all amino acids other than glycine are D-amino acids)

<400> SEQUENCE: 79

```
Val Val Leu Val Val Val Val Leu Val Thr Glu Ile Leu Ile Leu Asp
1               5                   10                  15

Ala Gly Gly Glu Val Leu Ala Lys Thr Ser Glu Gln Tyr Ala
            20                  25                  30
```

<210> SEQ ID NO 80
<211> LENGTH: 41
<212> TYPE: PRT
<213> ORGANISM: artificial
<220> FEATURE:
<223> OTHER INFORMATION: PYC12D-TAT peptide (the retroinverted form of
      PYC12 peptide comprising an N-terminal tat basic region protein
      transduction domain wherein all amino acids other than glycine are
      D-amino acids)

<400> SEQUENCE: 80

```
Val Val Leu Val Val Val Val Leu Val Thr Glu Ile Leu Ile Leu Asp
1               5                   10                  15

Ala Gly Gly Glu Val Leu Ala Lys Thr Ser Glu Gln Tyr Ala Gly Arg
            20                  25                  30

Arg Arg Gln Arg Arg Lys Lys Arg Gly
        35                  40
```

<210> SEQ ID NO 81
<211> LENGTH: 131
<212> TYPE: PRT
<213> ORGANISM: artificial
<220> FEATURE:
<223> OTHER INFORMATION: PYC15D peptide (the retroinverted form of PYC15
      peptide all amino acids other than glycine are D-amino acids)

<400> SEQUENCE: 81

```
Tyr Arg Tyr Arg His Met Leu Gln Tyr Trp Thr Leu Ser Cys Pro Arg
1               5                   10                  15
```

```
Arg Arg Cys Pro Lys Asp Asp Ile Leu Leu Val Ile Arg Phe Lys Leu
                 20                  25                  30

Leu Arg His Phe Phe Ser Leu Ile His Trp Phe Pro Lys Ala Met Pro
             35                  40                  45

Phe Asn Phe Ile Leu Val Asp Lys Asn Glu Leu Gly Cys Leu Phe Thr
         50                  55                  60

Ser Leu Lys Val Ser Ser Ile Ile Arg Gln Val Val Gly Gly Trp Leu
 65                  70                  75                  80

Pro Ile Asn Val Val Ser Ile Asn Glu Tyr Asp Ser Ala Ile Asp Leu
                 85                  90                  95

Ala Asp Lys Arg Ala Lys Phe Gly Ala Asp Arg Arg Ser Phe Asn Leu
                100                 105                 110

Asp Asn Leu Phe Tyr Met Lys Val Lys Asn Glu Pro Gly Lys Ile Ser
            115                 120                 125

Gln Tyr Thr
    130
```

```
<210> SEQ ID NO 82
<211> LENGTH: 142
<212> TYPE: PRT
<213> ORGANISM: artificial
<220> FEATURE:
<223> OTHER INFORMATION: PYC15D-TAT peptide (the retroinverted form of
      PYC15 peptide comprising an N-terminal tat basic region protein
      transduction domain wherein all amino acids other than glycine are
      D-amino acids)

<400> SEQUENCE: 82
```

```
Tyr Arg Tyr Arg His Met Leu Gln Tyr Trp Thr Leu Ser Cys Pro Arg
 1               5                  10                  15

Arg Arg Cys Pro Lys Asp Asp Ile Leu Leu Val Ile Arg Phe Lys Leu
                 20                  25                  30

Leu Arg His Phe Phe Ser Leu Ile His Trp Phe Pro Lys Ala Met Pro
             35                  40                  45

Phe Asn Phe Ile Leu Val Asp Lys Asn Glu Leu Gly Cys Leu Phe Thr
         50                  55                  60

Ser Leu Lys Val Ser Ser Ile Ile Arg Gln Val Val Gly Gly Trp Leu
 65                  70                  75                  80

Pro Ile Asn Val Val Ser Ile Asn Glu Tyr Asp Ser Ala Ile Asp Leu
                 85                  90                  95

Ala Asp Lys Arg Ala Lys Phe Gly Ala Asp Arg Arg Ser Phe Asn Leu
                100                 105                 110

Asp Asn Leu Phe Tyr Met Lys Val Lys Asn Glu Pro Gly Lys Ile Ser
            115                 120                 125

Gln Tyr Thr Gly Arg Arg Gln Arg Arg Lys Lys Arg Gly
    130                 135                 140
```

```
<210> SEQ ID NO 83
<211> LENGTH: 7
<212> TYPE: PRT
<213> ORGANISM: artificial
<220> FEATURE:
<223> OTHER INFORMATION: PYC18D peptide (the retroinverted form of PYC18
      peptide all amino acids other than glycine are D-amino acids)

<400> SEQUENCE: 83
```

```
His Ile Ile Ser Gln Tyr Ala
 1               5
```

```
<210> SEQ ID NO 84
<211> LENGTH: 18
<212> TYPE: PRT
<213> ORGANISM: artificial
<220> FEATURE:
<223> OTHER INFORMATION: PYC18D-TAT peptide (the retroinverted form of
      PYC18 peptide comprising an N-terminal tat basic region protein
      transduction domain wherein all amino acids other than glycine are
      D-amino acids)

<400> SEQUENCE: 84

His Ile Ile Ser Gln Tyr Ala Gly Arg Arg Arg Gln Arg Arg Lys Lys
1               5                   10                  15

Arg Gly

<210> SEQ ID NO 85
<211> LENGTH: 12
<212> TYPE: PRT
<213> ORGANISM: artificial
<220> FEATURE:
<223> OTHER INFORMATION: PYC19D peptide (the retroinverted form of PYC19
      peptide all amino acids other than glycine are D-amino acids)

<400> SEQUENCE: 85

Tyr Ile Tyr Pro Tyr Ala Tyr Ser Gln Asn Ile Leu
1               5                   10

<210> SEQ ID NO 86
<211> LENGTH: 23
<212> TYPE: PRT
<213> ORGANISM: artificial
<220> FEATURE:
<223> OTHER INFORMATION: PYC19D-TAT peptide (the retroinverted form of
      PYC19 peptide comprising an N-terminal tat basic region protein
      transduction domain wherein all amino acids other than glycine are
      D-amino acids)

<400> SEQUENCE: 86

Tyr Ile Tyr Pro Tyr Ala Tyr Ser Gln Asn Ile Leu Gly Arg Arg Arg
1               5                   10                  15

Gln Arg Arg Lys Lys Arg Gly
            20

<210> SEQ ID NO 87
<211> LENGTH: 19
<212> TYPE: PRT
<213> ORGANISM: artificial
<220> FEATURE:
<223> OTHER INFORMATION: PYC20D peptide (the retroinverted form of PYC20
      peptide all amino acids other than glycine are D-amino acids)

<400> SEQUENCE: 87

Pro Thr Ile Val Leu Leu Val Cys Trp Lys Thr Gly Trp Leu Ile Ser
1               5                   10                  15

Ser Tyr Ile

<210> SEQ ID NO 88
<211> LENGTH: 30
<212> TYPE: PRT
<213> ORGANISM: artificial
<220> FEATURE:
<223> OTHER INFORMATION: PYC20D-TAT peptide (the retroinverted form of
      PYC20 peptide comprising an N-terminal tat basic region protein
      transduction domain wherein all amino acids other than glycine are
      D-amino acids)

<400> SEQUENCE: 88
```

```
Pro Thr Ile Val Leu Val Cys Trp Lys Thr Gly Trp Leu Ile Ser
1               5                   10                  15

Ser Tyr Ile Gly Arg Arg Arg Gln Arg Arg Lys Lys Arg Gly
                20                  25                  30

<210> SEQ ID NO 89
<211> LENGTH: 24
<212> TYPE: PRT
<213> ORGANISM: artificial
<220> FEATURE:
<223> OTHER INFORMATION: PYC21D peptide (the retroinverted form of PYC21
      peptide all amino acids other than glycine are D-amino acids)

<400> SEQUENCE: 89

Arg Ile Lys Gly Met Asn Asp Phe Ile Asn Lys Ile Ser Asn Ser Ile
1               5                   10                  15

Asn Leu Phe Ile Tyr Ile Ile Ile
                20

<210> SEQ ID NO 90
<211> LENGTH: 35
<212> TYPE: PRT
<213> ORGANISM: artificial
<220> FEATURE:
<223> OTHER INFORMATION: PYC21D-TAT peptide (the retroinverted form of
      PYC21 peptide comprising an N-terminal tat basic region protein
      transduction domain wherein all amino acids other than glycine are
      D-amino acids)

<400> SEQUENCE: 90

Arg Ile Lys Gly Met Asn Asp Phe Ile Asn Lys Ile Ser Asn Ser Ile
1               5                   10                  15

Asn Leu Phe Ile Tyr Ile Ile Ile Gly Arg Arg Arg Gln Arg Arg Lys
                20                  25                  30

Lys Arg Gly
        35

<210> SEQ ID NO 91
<211> LENGTH: 41
<212> TYPE: PRT
<213> ORGANISM: artificial
<220> FEATURE:
<223> OTHER INFORMATION: PYC22D peptide (the retroinverted form of PYC22
      peptide all amino acids other than glycine are D-amino acids)

<400> SEQUENCE: 91

Asp Gly Pro Leu Asp Gly Arg Val Pro Tyr Val Ala Ala Asn Val Val
1               5                   10                  15

Glu Pro His Ser Met Leu Val Ala Glu Val Glu Gln Ser Ser Ile Asn
                20                  25                  30

Glu Gly Arg Arg Arg Ile Ser Asp Lys
        35                  40

<210> SEQ ID NO 92
<211> LENGTH: 52
<212> TYPE: PRT
<213> ORGANISM: artificial
<220> FEATURE:
<223> OTHER INFORMATION: PYC22D-TAT peptide (the retroinverted form of
      PYC22 peptide comprising an N-terminal tat basic region protein
      transduction domain wherein all amino acids other than glycine are
      D-amino acids)

<400> SEQUENCE: 92

Asp Gly Pro Leu Asp Gly Arg Val Pro Tyr Val Ala Ala Asn Val Val
```

```
                1               5                  10                  15

Glu Pro His Ser Met Leu Val Ala Glu Val Glu Gln Ser Ser Ile Asn
                20                  25                  30

Glu Gly Arg Arg Arg Ile Ser Asp Lys Gly Arg Arg Gln Arg
        35                  40                  45

Lys Lys Arg Gly
    50

<210> SEQ ID NO 93
<211> LENGTH: 26
<212> TYPE: PRT
<213> ORGANISM: artificial
<220> FEATURE:
<223> OTHER INFORMATION: PYC24D peptide (the retroinverted form of PYC24
      peptide all amino acids other than glycine are D-amino acids)

<400> SEQUENCE: 93

Asp Cys Ser Thr Phe Ala Lys Ala Val Pro Ala Val Phe Leu Leu Glu
1               5                  10                  15

Lys Thr Ala Thr Leu Leu Ser Gln Tyr Leu
            20                  25

<210> SEQ ID NO 94
<211> LENGTH: 37
<212> TYPE: PRT
<213> ORGANISM: artificial
<220> FEATURE:
<223> OTHER INFORMATION: PYC24D-TAT peptide (the retroinverted form of
      PYC24 peptide comprising an N-terminal tat basic region protein
      transduction domain wherein all amino acids other than glycine are
      D-amino acids)

<400> SEQUENCE: 94

Asp Cys Ser Thr Phe Ala Lys Ala Val Pro Ala Val Phe Leu Leu Glu
1               5                  10                  15

Lys Thr Ala Thr Leu Leu Ser Gln Tyr Leu Gly Arg Arg Arg Gln Arg
            20                  25                  30

Arg Lys Lys Arg Gly
        35

<210> SEQ ID NO 95
<211> LENGTH: 10
<212> TYPE: PRT
<213> ORGANISM: artificial
<220> FEATURE:
<223> OTHER INFORMATION: PYC29D peptide (the retroinverted form of PYC29
      peptide all amino acids other than glycine are D-amino acids)

<400> SEQUENCE: 95

Gln Ser Leu Phe Ser Ile Ser Gln Tyr Ala
1               5                  10

<210> SEQ ID NO 96
<211> LENGTH: 21
<212> TYPE: PRT
<213> ORGANISM: artificial
<220> FEATURE:
<223> OTHER INFORMATION: PYC29D-TAT peptide (the retroinverted form of
      PYC29 peptide comprising an N-terminal tat basic region protein
      transduction domain wherein all amino acids other than glycine are
      D-amino acids)

<400> SEQUENCE: 96

Gln Ser Leu Phe Ser Ile Ser Gln Tyr Ala Gly Arg Arg Arg Gln Arg
1               5                  10                  15
```

```
Arg Lys Lys Arg Gly
        20

<210> SEQ ID NO 97
<211> LENGTH: 41
<212> TYPE: PRT
<213> ORGANISM: artificial
<220> FEATURE:
<223> OTHER INFORMATION: PYC30D peptide (the retroinverted form of PYC30
      peptide all amino acids other than glycine are D-amino acids)

<400> SEQUENCE: 97

Asp Gly Pro Leu Asp Gly Arg Val Pro Tyr Val Ala Ala Asn Val Val
1               5                   10                  15

Glu Pro His Ser Met Leu Val Ala Glu Val Glu Gln Ser Ser Ile Asn
            20                  25                  30

Glu Gly Arg Arg Arg Ile Ser Asp Lys
        35                  40

<210> SEQ ID NO 98
<211> LENGTH: 52
<212> TYPE: PRT
<213> ORGANISM: artificial
<220> FEATURE:
<223> OTHER INFORMATION: PYC30D-TAT peptide (the retroinverted form of
      PYC30 peptide comprising an N-terminal tat basic region protein
      transduction domain wherein all amino acids other than glycine are
      D-amino acids)

<400> SEQUENCE: 98

Asp Gly Pro Leu Asp Gly Arg Val Pro Tyr Val Ala Ala Asn Val Val
1               5                   10                  15

Glu Pro His Ser Met Leu Val Ala Glu Val Glu Gln Ser Ser Ile Asn
            20                  25                  30

Glu Gly Arg Arg Arg Ile Ser Asp Lys Gly Arg Arg Arg Gln Arg Arg
        35                  40                  45

Lys Lys Arg Gly
    50

<210> SEQ ID NO 99
<211> LENGTH: 12
<212> TYPE: PRT
<213> ORGANISM: artificial
<220> FEATURE:
<223> OTHER INFORMATION: PYC32D peptide (the retroinverted form of PYC32
      peptide all amino acids other than glycine are D-amino acids)

<400> SEQUENCE: 99

Pro Asn Asn His Gly Asp Ser Ser His Pro Thr Asn
1               5                   10

<210> SEQ ID NO 100
<211> LENGTH: 23
<212> TYPE: PRT
<213> ORGANISM: artificial
<220> FEATURE:
<223> OTHER INFORMATION: PYC32D-TAT peptide (the retroinverted form of
      PYC32 peptide comprising an N-terminal tat basic region protein
      transduction domain wherein all amino acids other than glycine are
      D-amino acids)

<400> SEQUENCE: 100

Pro Asn Asn His Gly Asp Ser Ser His Pro Thr Asn Gly Arg Arg Arg
1               5                   10                  15
```

Gln Arg Arg Lys Lys Arg Gly
        20

<210> SEQ ID NO 101
<211> LENGTH: 29
<212> TYPE: PRT
<213> ORGANISM: artificial
<220> FEATURE:
<223> OTHER INFORMATION: PYC34D peptide (the retroinverted form of PYC34
      peptide all amino acids other than glycine are D-amino acids)

<400> SEQUENCE: 101

Ser Lys Thr Val His Gln Lys Leu His Leu Ser Leu Glu Gln Ser Asn
1               5                   10                  15

Glu Pro Leu Val Pro Ser Ser Asn Ile Ser Gln Tyr Ala
            20                  25

<210> SEQ ID NO 102
<211> LENGTH: 40
<212> TYPE: PRT
<213> ORGANISM: artificial
<220> FEATURE:
<223> OTHER INFORMATION: PYC34D-TAT peptide (the retroinverted form of
      PYC34 peptide comprising an N-terminal tat basic region protein
      transduction domain wherein all amino acids other than glycine are
      D-amino acids)

<400> SEQUENCE: 102

Ser Lys Thr Val His Gln Lys Leu His Leu Ser Leu Glu Gln Ser Asn
1               5                   10                  15

Glu Pro Leu Val Pro Ser Ser Asn Ile Ser Gln Tyr Ala Gly Arg Arg
            20                  25                  30

Arg Gln Arg Arg Lys Lys Arg Gly
        35                  40

<210> SEQ ID NO 103
<211> LENGTH: 18
<212> TYPE: PRT
<213> ORGANISM: artificial
<220> FEATURE:
<223> OTHER INFORMATION: PYC35D peptide (the retroinverted form of PYC35
      peptide all amino acids other than glycine are D-amino acids)

<400> SEQUENCE: 103

Arg Glu Arg Lys Ser Ser Ser Glu Ile Gly Gly Ser Arg Ile Ser Gln
1               5                   10                  15

Tyr Ala

<210> SEQ ID NO 104
<211> LENGTH: 29
<212> TYPE: PRT
<213> ORGANISM: artificial
<220> FEATURE:
<223> OTHER INFORMATION: PYC35D-TAT peptide (the retroinverted form of
      PYC35 peptide comprising an N-terminal tat basic region protein
      transduction domain wherein all amino acids other than glycine are
      D-amino acids)

<400> SEQUENCE: 104

Arg Glu Arg Lys Ser Ser Ser Glu Ile Gly Gly Ser Arg Ile Ser Gln
1               5                   10                  15

Tyr Ala Gly Arg Arg Arg Gln Arg Arg Lys Lys Arg Gly
            20                  25

<210> SEQ ID NO 105

```
<211> LENGTH: 15
<212> TYPE: PRT
<213> ORGANISM: artificial
<220> FEATURE:
<223> OTHER INFORMATION: PYC36D peptide (the retroinverted form of PYC36
      peptide all amino acids other than glycine are D-amino acids)

<400> SEQUENCE: 105

Pro Lys Ile Ser Gln Tyr Gly Gln Arg Arg Gly Gln Leu Gly
1               5                   10                  15

<210> SEQ ID NO 106
<211> LENGTH: 26
<212> TYPE: PRT
<213> ORGANISM: artificial
<220> FEATURE:
<223> OTHER INFORMATION: PYC36D-TAT peptide (the retroinverted form of
      PYC36 peptide comprising an N-terminal tat basic region protein
      transduction domain wherein all amino acids other than glycine are
      D-amino acids)

<400> SEQUENCE: 106

Pro Lys Ile Ser Gln Tyr Gly Gln Arg Arg Gly Gln Leu Gly Gly
1               5                   10                  15

Arg Arg Arg Gln Arg Arg Lys Lys Arg Gly
            20                  25

<210> SEQ ID NO 107
<211> LENGTH: 25
<212> TYPE: PRT
<213> ORGANISM: artificial
<220> FEATURE:
<223> OTHER INFORMATION: PYC38D peptide (the retroinverted form of PYC38
      peptide all amino acids other than glycine are D-amino acids)

<400> SEQUENCE: 107

Arg His Ala Pro Leu Ala Arg Gly Ser Trp Arg Gly Gln Pro Gln Gln
1               5                   10                  15

Gly Pro Gln Arg Arg Gly Gln Leu Gly
            20                  25

<210> SEQ ID NO 108
<211> LENGTH: 36
<212> TYPE: PRT
<213> ORGANISM: artificial
<220> FEATURE:
<223> OTHER INFORMATION: PYC38D-TAT peptide (the retroinverted form of
      PYC38 peptide comprising an N-terminal tat basic region protein
      transduction domain wherein all amino acids other than glycine are
      D-amino acids)

<400> SEQUENCE: 108

Arg His Ala Pro Leu Ala Arg Gly Ser Trp Arg Gly Gln Pro Gln Gln
1               5                   10                  15

Gly Pro Gln Arg Arg Gly Gln Leu Gly Gly Arg Arg Arg Gln Arg Arg
            20                  25                  30

Lys Lys Arg Gly
        35

<210> SEQ ID NO 109
<211> LENGTH: 25
<212> TYPE: PRT
<213> ORGANISM: artificial
<220> FEATURE:
<223> OTHER INFORMATION: PYC39D peptide (the retroinverted form of PYC39
      peptide all amino acids other than glycine are D-amino acids)
```

```
<400> SEQUENCE: 109

Arg His Ala Pro Leu Ala Arg Gly Ser Trp Arg Gly Gln Pro Gln Gln
1               5                   10                  15

Gly Pro Gln Arg Arg Gly Gln Leu Gly
            20                  25

<210> SEQ ID NO 110
<211> LENGTH: 36
<212> TYPE: PRT
<213> ORGANISM: artificial
<220> FEATURE:
<223> OTHER INFORMATION: PYC39D-TAT peptide (the retroinverted form of
      PYC39 peptide comprising an N-terminal tat basic region protein
      transduction domain wherein all amino acids other than glycine are
      D-amino acids)

<400> SEQUENCE: 110

Arg His Ala Pro Leu Ala Arg Gly Ser Trp Arg Gly Gln Pro Gln Gln
1               5                   10                  15

Gly Pro Gln Arg Arg Gly Gln Leu Gly Gly Arg Arg Gln Arg Arg
            20                  25                  30

Lys Lys Arg Gly
        35

<210> SEQ ID NO 111
<211> LENGTH: 61
<212> TYPE: PRT
<213> ORGANISM: artificial
<220> FEATURE:
<223> OTHER INFORMATION: PYC54D peptide (the retroinverted form of PYC54
      peptide all amino acids other than glycine are D-amino acids)

<400> SEQUENCE: 111

Tyr Arg Tyr Arg His Met Leu Gln Tyr Trp Thr Leu Ser Cys Pro Arg
1               5                   10                  15

Arg Arg Cys Thr Tyr Asp Ile Met Thr Glu Gln Thr Ala Glu Val Leu
            20                  25                  30

Lys Arg Ala Thr Ala Ser Val Ser Gly Val Leu Phe Thr Arg Ser Thr
        35                  40                  45

Asp Gly His Tyr Gly Ala Leu Ser Ile Ser Gln Tyr Ala
    50                  55                  60

<210> SEQ ID NO 112
<211> LENGTH: 72
<212> TYPE: PRT
<213> ORGANISM: artificial
<220> FEATURE:
<223> OTHER INFORMATION: PYC54D-TAT peptide (the retroinverted form of
      PYC54 peptide comprising an N-terminal tat basic region protein
      transduction domain wherein all amino acids other than glycine are
      D-amino acids)

<400> SEQUENCE: 112

Tyr Arg Tyr Arg His Met Leu Gln Tyr Trp Thr Leu Ser Cys Pro Arg
1               5                   10                  15

Arg Arg Cys Thr Tyr Asp Ile Met Thr Glu Gln Thr Ala Glu Val Leu
            20                  25                  30

Lys Arg Ala Thr Ala Ser Val Ser Gly Val Leu Phe Thr Arg Ser Thr
        35                  40                  45

Asp Gly His Tyr Gly Ala Leu Ser Ile Ser Gln Tyr Ala Gly Arg Arg
    50                  55                  60

Arg Gln Arg Arg Lys Lys Arg Gly
```

65                  70

<210> SEQ ID NO 113
<211> LENGTH: 63
<212> TYPE: PRT
<213> ORGANISM: artificial
<220> FEATURE:
<223> OTHER INFORMATION: PYC58D peptide (the retroinverted form of PYC58
      peptide all amino acids other than glycine are D-amino acids)

<400> SEQUENCE: 113

Tyr Arg Tyr Arg His Met Leu Gln Tyr Trp Ala Leu Ser Cys Pro Arg
1               5                   10                  15

Arg Arg Cys Leu Glu His Phe Leu Pro Thr Arg Leu His Gln Asp Gly
            20                  25                  30

Ser Asp Ile Gly Val Gln Gly Arg Arg Gln Arg Gly Val Leu Phe
        35                  40                  45

Ala Val Pro Gln Gln Ala Ala Val Ala Met Ile Ser Gln Tyr Ala
    50                  55                  60

<210> SEQ ID NO 114
<211> LENGTH: 74
<212> TYPE: PRT
<213> ORGANISM: artificial
<220> FEATURE:
<223> OTHER INFORMATION: PYC58D-TAT peptide (the retroinverted form of
      PYC58 peptide comprising an N-terminal tat basic region protein
      transduction domain wherein all amino acids other than glycine are
      D-amino acids)

<400> SEQUENCE: 114

Tyr Arg Tyr Arg His Met Leu Gln Tyr Trp Ala Leu Ser Cys Pro Arg
1               5                   10                  15

Arg Arg Cys Leu Glu His Phe Leu Pro Thr Arg Leu His Gln Asp Gly
            20                  25                  30

Ser Asp Ile Gly Val Gln Gly Arg Arg Gln Arg Gly Val Leu Phe
        35                  40                  45

Ala Val Pro Gln Gln Ala Ala Val Ala Met Ile Ser Gln Tyr Ala Gly
    50                  55                  60

Arg Arg Arg Gln Arg Arg Lys Lys Arg Gly
65                  70

<210> SEQ ID NO 115
<211> LENGTH: 13
<212> TYPE: PRT
<213> ORGANISM: artificial
<220> FEATURE:
<223> OTHER INFORMATION: PYC59D peptide (the retroinverted form of PYC59
      peptide all amino acids other than glycine are D-amino acids)

<400> SEQUENCE: 115

Val Val Leu Val Val Val Val Ser Ile Ser Gln Tyr Ala
1               5                   10

<210> SEQ ID NO 116
<211> LENGTH: 24
<212> TYPE: PRT
<213> ORGANISM: artificial
<220> FEATURE:
<223> OTHER INFORMATION: PYC59D-TAT peptide (the retroinverted form of
      PYC59 peptide comprising an N-terminal tat basic region protein
      transduction domain wherein all amino acids other than glycine are
      D-amino acids)

<400> SEQUENCE: 116

```
Val Val Leu Val Val Val Val Ser Ile Ser Gln Tyr Ala Gly Arg Arg
1               5                   10                  15

Arg Gln Arg Arg Lys Lys Arg Gly
            20

<210> SEQ ID NO 117
<211> LENGTH: 17
<212> TYPE: PRT
<213> ORGANISM: artificial
<220> FEATURE:
<223> OTHER INFORMATION: PYC60D peptide (the retroinverted form of PYC60
      peptide all amino acids other than glycine are D-amino acids)

<400> SEQUENCE: 117

Cys Lys Ile Phe Ile Leu Arg Gly Ala Leu Ile Lys Pro Leu Gln Asn
1               5                   10                  15

Ala

<210> SEQ ID NO 118
<211> LENGTH: 28
<212> TYPE: PRT
<213> ORGANISM: artificial
<220> FEATURE:
<223> OTHER INFORMATION: PYC60D-TAT peptide (the retroinverted form of
      PYC60 peptide comprising an N-terminal tat basic region protein
      transduction domain wherein all amino acids other than glycine are
      D-amino acids)

<400> SEQUENCE: 118

Cys Lys Ile Phe Ile Leu Arg Gly Ala Leu Ile Lys Pro Leu Gln Asn
1               5                   10                  15

Ala Gly Arg Arg Arg Gln Arg Arg Lys Lys Arg Gly
            20                  25

<210> SEQ ID NO 119
<211> LENGTH: 64
<212> TYPE: PRT
<213> ORGANISM: artificial
<220> FEATURE:
<223> OTHER INFORMATION: PYC66D peptide (the retroinverted form of PYC66
      peptide all amino acids other than glycine are D-amino acids)

<400> SEQUENCE: 119

Tyr Arg Tyr Arg His Met Leu Gln Tyr Trp Thr Leu Ser Cys Pro Arg
1               5                   10                  15

Arg Arg Cys Gln Gln Ala His Ala Thr Asn Lys Pro Ser Ile Ala Gln
            20                  25                  30

Gly Glu Leu Trp Ile Thr Gly Arg Asp Ala His Tyr Val Gly Thr Leu
        35                  40                  45

Ala Lys Ile Leu Thr Ser Lys Gly Ala Gly Ile Ile Ser Gln Tyr Ala
    50                  55                  60

<210> SEQ ID NO 120
<211> LENGTH: 75
<212> TYPE: PRT
<213> ORGANISM: artificial
<220> FEATURE:
<223> OTHER INFORMATION: PYC66D-TAT peptide (the retroinverted form of
      PYC66 peptide comprising an N-terminal tat basic region protein
      transduction domain wherein all amino acids other than glycine are
      D-amino acids)

<400> SEQUENCE: 120

Tyr Arg Tyr Arg His Met Leu Gln Tyr Trp Thr Leu Ser Cys Pro Arg
```

```
                1               5                  10                 15
Arg Arg Cys Gln Gln Ala His Ala Thr Asn Lys Pro Ser Ile Ala Gln
                20                  25                  30

Gly Glu Leu Trp Ile Thr Gly Arg Asp Ala His Tyr Val Gly Thr Leu
            35                  40                  45

Ala Lys Ile Leu Thr Ser Lys Gly Ala Gly Ile Ile Ser Gln Tyr Ala
    50                  55                  60

Gly Arg Arg Arg Gln Arg Arg Lys Lys Arg Gly
65                  70                  75

<210> SEQ ID NO 121
<211> LENGTH: 20
<212> TYPE: PRT
<213> ORGANISM: artificial
<220> FEATURE:
<223> OTHER INFORMATION: JNK inhibitory peptide IB-1

<400> SEQUENCE: 121

Asp Thr Tyr Arg Pro Lys Arg Pro Thr Thr Leu Asn Leu Phe Pro Gln
1               5                   10                  15

Val Pro Arg Ser
            20

<210> SEQ ID NO 122
<211> LENGTH: 21
<212> TYPE: PRT
<213> ORGANISM: artificial
<220> FEATURE:
<223> OTHER INFORMATION: JNK inhibitory peptide IB-2

<400> SEQUENCE: 122

Glu Glu Pro His Lys His Arg Pro Thr Thr Leu Arg Leu Thr Thr Leu
1               5                   10                  15

Gly Ala Gln Asp Ser
            20

<210> SEQ ID NO 123
<211> LENGTH: 19
<212> TYPE: PRT
<213> ORGANISM: artificial
<220> FEATURE:
<223> OTHER INFORMATION: Generic IB JNK inhibitory peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 123

Xaa Arg Pro Thr Thr Leu Xaa Leu Xaa Xaa Xaa Xaa Xaa Xaa Xaa Gln
1               5                   10                  15

Asp Ser Xaa

<210> SEQ ID NO 124
```

```
<211> LENGTH: 19
<212> TYPE: PRT
<213> ORGANISM: artificial
<220> FEATURE:
<223> OTHER INFORMATION: Generic IB JNK inhibitory peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 124

Xaa Arg Pro Thr Thr Leu Xaa Leu Xaa Xaa Xaa Xaa Xaa Xaa Xaa Gln
1               5                   10                  15

Asp Thr Xaa

<210> SEQ ID NO 125
<211> LENGTH: 20
<212> TYPE: PRT
<213> ORGANISM: artificial
<220> FEATURE:
<223> OTHER INFORMATION: Retro-inverted generic IB JNK inhibitory
      peptide (wherein each amino acid other than glycine is a D amino
      acid)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 125

Xaa Ser Asp Gln Xaa Xaa Xaa Xaa Xaa Xaa Xaa Leu Xaa Leu Thr Thr
1               5                   10                  15

Pro Arg Xaa Leu
            20

<210> SEQ ID NO 126
<211> LENGTH: 20
<212> TYPE: PRT
<213> ORGANISM: artificial
<220> FEATURE:
<223> OTHER INFORMATION: Retro-inverted generic IB JNK inhibitory
      peptide (wherein each amino acid other than glycine is a D amino
      acid)
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(11)
```

```
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 126

Xaa Thr Asp Gln Xaa Xaa Xaa Xaa Xaa Xaa Xaa Leu Xaa Leu Thr Thr
1               5                   10                  15

Pro Arg Xaa Leu
            20

<210> SEQ ID NO 127
<211> LENGTH: 23
<212> TYPE: PRT
<213> ORGANISM: artificial
<220> FEATURE:
<223> OTHER INFORMATION: Retro-inverted IB-1 JNK inhibitory peptide
      (wherein each amino acid other than glycine is a D amino acid)

<400> SEQUENCE: 127

Thr Asp Gln Ser Arg Pro Val Gln Pro Phe Leu Asn Leu Thr Thr Pro
1               5                   10                  15

Arg Lys Pro Arg Tyr Thr Asp
            20

<210> SEQ ID NO 128
<211> LENGTH: 22
<212> TYPE: PRT
<213> ORGANISM: artificial
<220> FEATURE:
<223> OTHER INFORMATION: Retro-inverted IB-2 JNK inhibitory peptide
      (wherein each amino acid other than glycine is a D amino acid)

<400> SEQUENCE: 128

Ser Asp Gln Ala Gly Leu Thr Thr Leu Arg Leu Thr Thr Pro Arg His
1               5                   10                  15

Lys His Pro Glu Glu Leu
            20

<210> SEQ ID NO 129
<211> LENGTH: 11
<212> TYPE: PRT
<213> ORGANISM: artificial
<220> FEATURE:
<223> OTHER INFORMATION: TI-JIP peptide

<400> SEQUENCE: 129

Arg Pro Lys Arg Pro Thr Thr Leu Asn Leu Phe
1               5                   10

<210> SEQ ID NO 130
<211> LENGTH: 11
<212> TYPE: PRT
<213> ORGANISM: artificial
<220> FEATURE:
<223> OTHER INFORMATION: Retro-inverted TI-JIP peptide (wherein each
      amino acid other than glycine is a D amino acid)

<400> SEQUENCE: 130

Phe Leu Asn Leu Thr Thr Pro Arg Lys Pro Arg
1               5                   10
```

<210> SEQ ID NO 131
<211> LENGTH: 19
<212> TYPE: PRT
<213> ORGANISM: artificial
<220> FEATURE:
<223> OTHER INFORMATION: JNK inhibitory peptide

<400> SEQUENCE: 131

Arg Pro Lys Arg Pro Thr Thr Leu Asn Leu Phe Pro Gln Val Pro Arg
1               5                   10                  15

Ser Gln Asp

<210> SEQ ID NO 132
<211> LENGTH: 19
<212> TYPE: DNA
<213> ORGANISM: artificial
<220> FEATURE:
<223> OTHER INFORMATION: AP-1 decoy oligonucleotide

<400> SEQUENCE: 132
gcttgatgag tcagccgga                                              19

<210> SEQ ID NO 133
<211> LENGTH: 33
<212> TYPE: DNA
<213> ORGANISM: artificial
<220> FEATURE:
<223> OTHER INFORMATION: Dz13 DNAzyme

<400> SEQUENCE: 133
cgggaggaag gctagctaca acgagaggcg ttg                              33

<210> SEQ ID NO 134
<211> LENGTH: 21
<212> TYPE: DNA
<213> ORGANISM: artificial
<220> FEATURE:
<223> OTHER INFORMATION: c-Jun specific siRNA

<400> SEQUENCE: 134
cagcttcctg cctttgtaat t                                           21

<210> SEQ ID NO 135
<211> LENGTH: 19
<212> TYPE: DNA
<213> ORGANISM: artificial
<220> FEATURE:
<223> OTHER INFORMATION: JNK specific siRNA

<400> SEQUENCE: 135
cgtggattta tggtctgtg                                              19

<210> SEQ ID NO 136
<211> LENGTH: 19
<212> TYPE: DNA
<213> ORGANISM: artificial
<220> FEATURE:
<223> OTHER INFORMATION: JNK specific siRNA

<400> SEQUENCE: 136
agaatgtcct accttctct                                              19

<210> SEQ ID NO 137
<211> LENGTH: 10
<212> TYPE: PRT

```
<213> ORGANISM: artificial
<220> FEATURE:
<223> OTHER INFORMATION: HIV tat basic region protein transduction
      domain

<400> SEQUENCE: 137

Gly Arg Lys Lys Arg Arg Gln Arg Arg Arg
1               5                   10

<210> SEQ ID NO 138
<211> LENGTH: 11
<212> TYPE: PRT
<213> ORGANISM: artificial
<220> FEATURE:
<223> OTHER INFORMATION: HIV tat basic region protein transduction
      domain

<400> SEQUENCE: 138

Gly Arg Lys Lys Arg Arg Gln Arg Arg Arg Pro
1               5                   10

<210> SEQ ID NO 139
<211> LENGTH: 12
<212> TYPE: PRT
<213> ORGANISM: artificial
<220> FEATURE:
<223> OTHER INFORMATION: HIV tat basic region protein transduction
      domain

<400> SEQUENCE: 139

Gly Arg Lys Lys Arg Arg Gln Arg Arg Arg Pro Pro
1               5                   10

<210> SEQ ID NO 140
<211> LENGTH: 13
<212> TYPE: PRT
<213> ORGANISM: artificial
<220> FEATURE:
<223> OTHER INFORMATION: HIV tat basic region protein transduction
      domain

<400> SEQUENCE: 140

Gly Arg Lys Lys Arg Arg Gln Arg Arg Arg Pro Pro Gln
1               5                   10

<210> SEQ ID NO 141
<211> LENGTH: 11
<212> TYPE: PRT
<213> ORGANISM: artificial
<220> FEATURE:
<223> OTHER INFORMATION: HIV tat basic region protein transduction
      domain

<400> SEQUENCE: 141

Gly Arg Lys Lys Arg Arg Gln Arg Arg Arg Gly
1               5                   10

<210> SEQ ID NO 142
<211> LENGTH: 12
<212> TYPE: PRT
<213> ORGANISM: artificial
<220> FEATURE:
<223> OTHER INFORMATION: HIV tat basic region protein transduction
      domain

<400> SEQUENCE: 142

Gly Arg Lys Lys Arg Arg Gln Arg Arg Arg Pro Gly
1               5                   10
```

<210> SEQ ID NO 143
<211> LENGTH: 13
<212> TYPE: PRT
<213> ORGANISM: artificial
<220> FEATURE:
<223> OTHER INFORMATION: HIV tat basic region protein transduction
      domain

<400> SEQUENCE: 143

Gly Arg Lys Lys Arg Arg Gln Arg Arg Arg Pro Pro Gly
1               5                   10

<210> SEQ ID NO 144
<211> LENGTH: 14
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 144

Gly Arg Lys Lys Arg Arg Gln Arg Arg Arg Pro Pro Gln Gly
1               5                   10

<210> SEQ ID NO 145
<211> LENGTH: 10
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 145

Arg Arg Arg Gln Arg Arg Lys Lys Arg Gly
1               5                   10

<210> SEQ ID NO 146
<211> LENGTH: 11
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 146

Pro Arg Arg Arg Gln Arg Arg Lys Lys Arg Gly
1               5                   10

<210> SEQ ID NO 147
<211> LENGTH: 12
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 147

Pro Pro Arg Arg Arg Gln Arg Arg Lys Lys Arg Gly
1               5                   10

<210> SEQ ID NO 148
<211> LENGTH: 13
<212> TYPE: PRT

<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 148

Gln Pro Pro Arg Arg Arg Gln Arg Arg Lys Lys Arg Gly
1               5                   10

<210> SEQ ID NO 149
<211> LENGTH: 11
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 149

Gly Arg Arg Arg Gln Arg Arg Lys Lys Arg Gly
1               5                   10

<210> SEQ ID NO 150
<211> LENGTH: 12
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 150

Gly Pro Arg Arg Arg Gln Arg Arg Lys Lys Arg Gly
1               5                   10

<210> SEQ ID NO 151
<211> LENGTH: 13
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 151

Gly Pro Pro Arg Arg Arg Gln Arg Arg Lys Lys Arg Gly
1               5                   10

<210> SEQ ID NO 152
<211> LENGTH: 14
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 152

Gly Gln Pro Pro Arg Arg Arg Gln Arg Arg Lys Lys Arg Gly
1               5                   10

<210> SEQ ID NO 153
<211> LENGTH: 27
<212> TYPE: PRT
<213> ORGANISM: artificial
<220> FEATURE:
<223> OTHER INFORMATION: signal sequence peptide 1 protein transduction
      domain

```
<400> SEQUENCE: 153

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 154
<211> LENGTH: 16
<212> TYPE: PRT
<213> ORGANISM: artificial
<220> FEATURE:
<223> OTHER INFORMATION: signal sequence peptide 2 protein transduction
      domain

<400> SEQUENCE: 154

Ala Ala Val Ala Leu Leu Pro Ala Val Leu Leu Ala Leu Leu Ala Pro
1               5                   10                  15

<210> SEQ ID NO 155
<211> LENGTH: 26
<212> TYPE: PRT
<213> ORGANISM: artificial
<220> FEATURE:
<223> OTHER INFORMATION: transportan protein transduction domain

<400> SEQUENCE: 155

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 156
<211> LENGTH: 18
<212> TYPE: PRT
<213> ORGANISM: artificial
<220> FEATURE:
<223> OTHER INFORMATION: amphiphilic model peptide protein transduction
      domain

<400> SEQUENCE: 156

Lys Leu Ala Leu Lys Leu Ala Leu Lys Ala Leu Lys Ala Ala Leu Lys
1               5                   10                  15

Leu Ala

<210> SEQ ID NO 157
<211> LENGTH: 9
<212> TYPE: PRT
<213> ORGANISM: artificial
<220> FEATURE:
<223> OTHER INFORMATION: polyarginine protein transduction domain

<400> SEQUENCE: 157

Arg Arg Arg Arg Arg Arg Arg Arg Arg
1               5

<210> SEQ ID NO 158
<211> LENGTH: 11
<212> TYPE: PRT
<213> ORGANISM: artificial
<220> FEATURE:
<223> OTHER INFORMATION: transdermal delivery peptide

<400> SEQUENCE: 158

Ala Cys Ser Ser Ser Pro Ser Lys His Cys Gly
```

<210> SEQ ID NO 159
<211> LENGTH: 12
<212> TYPE: PRT
<213> ORGANISM: artificial
<220> FEATURE:
<223> OTHER INFORMATION: Kaposi fibroblast growth factor (FGF)
    hydrophobic peptide protein transduction domain

<400> SEQUENCE: 159

Ala Ala Val Leu Leu Pro Val Leu Leu Ala Ala Pro
1               5                   10

<210> SEQ ID NO 160
<211> LENGTH: 13
<212> TYPE: PRT
<213> ORGANISM: artificial
<220> FEATURE:
<223> OTHER INFORMATION: Kaposi fibroblast growth factor (FGF)
    hydrophobic peptide protein transduction domain

<400> SEQUENCE: 160

Gly Ala Ala Val Leu Leu Pro Val Leu Leu Ala Ala Pro
1               5                   10

<210> SEQ ID NO 161
<211> LENGTH: 12
<212> TYPE: PRT
<213> ORGANISM: artificial
<220> FEATURE:
<223> OTHER INFORMATION: retroinverted Kaposi fibroblast growth factor
    (FGF) hydrophobic peptide protein transduction domain (wherein
    each amino acid other than glycine is a D amino acid)

<400> SEQUENCE: 161

Pro Ala Ala Leu Leu Val Pro Leu Leu Val Ala Ala
1               5                   10

<210> SEQ ID NO 162
<211> LENGTH: 13
<212> TYPE: PRT
<213> ORGANISM: artificial
<220> FEATURE:
<223> OTHER INFORMATION: retroinverted Kaposi fibroblast growth factor
    (FGF) hydrophobic peptide protein transduction domain (wherein
    each amino acid other than glycine is a D amino acid)

<400> SEQUENCE: 162

Pro Ala Ala Leu Leu Val Pro Leu Leu Val Ala Ala Gly
1               5                   10

<210> SEQ ID NO 163
<211> LENGTH: 13
<212> TYPE: PRT
<213> ORGANISM: artificial
<220> FEATURE:
<223> OTHER INFORMATION: PYC 41 peptide

<400> SEQUENCE: 163

Val Ser Ile Asn Gln Glu His His Arg Leu Leu Pro Leu
1               5                   10

<210> SEQ ID NO 164
<211> LENGTH: 13
<212> TYPE: PRT
<213> ORGANISM: artificial
<220> FEATURE:

```
<223> OTHER INFORMATION: PYC41D peptide (wherein each amino acid other
      than glycine is a D amino acid)

<400> SEQUENCE: 164

Leu Pro Leu Leu Arg His His Glu Gln Asn Ile Ser Val
1               5                   10

<210> SEQ ID NO 165
<211> LENGTH: 24
<212> TYPE: PRT
<213> ORGANISM: artificial
<220> FEATURE:
<223> OTHER INFORMATION: PYC41D-tat peptide comprising a HIV tat basic
      region protien transduction domain (wherein each amino acid other
      than glycine is a D amino acid)

<400> SEQUENCE: 165

Leu Pro Leu Leu Arg His His Glu Gln Asn Ile Ser Val Gly Arg Arg
1               5                   10                  15

Arg Gln Arg Arg Lys Lys Arg Gly
            20

<210> SEQ ID NO 166
<211> LENGTH: 46
<212> TYPE: DNA
<213> ORGANISM: artificial sequence
<220> FEATURE:
<223> OTHER INFORMATION: Tagged random oligonucleotides for primer
      extension amplification
<220> FEATURE:
<221> NAME/KEY: misc_feature
<222> LOCATION: (41)..(46)
<223> OTHER INFORMATION: n is a, c, g, or t

<400> SEQUENCE: 166
gactacaagg acgacgacga caaggcttat caatcaatca nnnnnn                    46

<210> SEQ ID NO 167
<211> LENGTH: 49
<212> TYPE: DNA
<213> ORGANISM: artificial sequence
<220> FEATURE:
<223> OTHER INFORMATION: Tagged random oligonucleotides for primer
      extension amplification
<220> FEATURE:
<221> NAME/KEY: misc_feature
<222> LOCATION: (41)..(49)
<223> OTHER INFORMATION: n is a, c, g, or t

<400> SEQUENCE: 167
gactacaagg acgacgacga caaggcttat caatcaatca nnnnnnnnn                 49

<210> SEQ ID NO 168
<211> LENGTH: 40
<212> TYPE: DNA
<213> ORGANISM: artificial sequence
<220> FEATURE:
<223> OTHER INFORMATION: Oligonucleotide for use in PCR reaction to
      incorporate an EcoRI endonuclease site

<400> SEQUENCE: 168
gagagaattc aggtcagact acaaggacga cgacgacaag                           40
```

COMPOSITIONS AND USES THEREOF FOR THE TREATMENT OF ACUTE RESPIRATORY DISTRESS SYNDROME (ARDS) AND CLINICAL DISORDERS ASSOCIATED WITH THEREWITH

RELATED APPLICATION DATA

This application is the National Stage of International Application No. PCT/AU2008/000903, filed Jun. 20, 2008, and claims the benefit of U.S. Provisional Application No. 60/945,215, filed Jun. 20, 2007, both of which are incorporated by reference in their entirety.

FIELD OF THE INVENTION

The present invention relates to therapeutic and prophylactic methods for the treatment of acute respiratory distress syndrome (ARDS) and clinical disorders associated with the development of ARDS, and compositions and formulations therefore, especially intranasal formulations.

BACKGROUND OF THE INVENTION

Description of the Related Art

1. Acute Respiratory Distress Syndrome (ARDS)

Acute respiratory distress syndrome ("ARDS") is a manifestation of a systemic inflammatory response that develops, for example, as a consequence of direct or indirect lung injury e.g., in both medical and surgical patients. The hallmark of ARDS is deterioration in blood oxygenation and respiratory system compliance as a consequence of permeability edema.

A consensus definition of ARDS, as recommended in 1994 by the American-European Consensus Conference Committee, distinguishes ARDS from other conditions such as acute lung injury (ALI) based on differing severity of clinical lung injury: patients with less severe hypoxemia are considered to have ALI, and those with more severe hypoxemia are considered to have the ARDS. As a consequence, ARDS is defined by the following criteria (Bernard et al., *Am. J. Respir. Crit. Care Med* 149, 818-824, 1994):

1. Acute onset;
2. Bilateral infiltrates on chest radiography;
3. Pulmonary-artery wedge pressure is less than or equal to 18 mm Hg or the absence of clinical evidence of left atrial hypertension; and
4. hypoxemia, as determined by the ratio of partial pressure of arterial oxygen to fraction of inspired oxygen, i.e., $PaO_2$:$FiO_2$, is less than or equal to 200.

In contrast, in ALI, hypoxemia as determined by the ratio $PaO_2$:$FiO_2$, is less than or equal to 300.

ARDS is often progressive, characterized by distinct stages exhibiting different clinical, histopathological and radiographic parameters.

An acute phase of ARDS involves acute neutrophil influx to the lungs e.g., arising from e.g., sepsis, pneumonia, aspiration, ischemia (circulatory arrest, hemorrhagic shock), trauma, severe asthma, poisoning, severe acute respiratory syndrome (SARS), influenza, or infection.

The acute phase of ARDS is characterized by rapid onset of respiratory failure in a patient having a predisposition for the condition, especially arterial hypoxemia that is refractory to oxygen supplementation. Bronch-alveolar-lavage (BAL) studies reveal substantial inflammation in areas that appear normal by radiography or tomography as well as in areas that exhibit alveolar filling, consolidation and atelectasis. Pathologically, the lung in this acute phase exhibits diffuse alveolar damage, with neutrophils, macrophages, erythrocytes, hyaline membranes, capillary injury and disruption of the alveolar epithelium.

More particularly, the acute phase of the condition is characterized by sloughing of the bronchiolar and alveolar epithelial cells, with the formation of protein-rich hyaline membranes on the basement membrane. Neutrophils have been detected adhering to the injured capillary endothelium and marginating through the interstitium into the air space, which is filled with edema fluid. In the air space, alveolar macrophages secrete cytokines such as the interleukins IL-1, IL-6, IL-8 and IL-10, and tumor necrosis factor-$\alpha$ (TNF-$\alpha$), which act locally to stimulate chemotaxis and activate neutrophils to release oxidants, proteases, leukotrienes and other pro-inflammatory molecules such as platelet activating factor (PAF). The production of proinflammatory cytokines, and the balance between proinflammatory cytokines and anti-inflammatory mediators e.g., IL-1 receptor antagonist, soluble TNF, autoantibodies against IL-8, and anti-inflammatory cytokines IL-10 and IL-11 determine the extent of inflammatory response. The inflammatory response may result in vascular leakage of plasma proteins into the alveolar spaces of the lungs causing lung edema.

The acute phase may progress to fibrosing alveolitis with persistent hypoxemia, increased alveolar dead space and further decrease in alveolar compliance. In patients with ARDS the microvascular, interstitial and alveolar spaces of the lungs are the primary targets for fibrin deposition, and micro thrombus formation can occur in multiple organs, with lungs and kidneys as the most exposed, leading to multiple organ failure (MOF). Pulmonary hypertension may arise from obliteration of the pulmonary capillary bed and, in severe cases this may cause right ventricular failure. Pneumothorax may occur in about 10-13% of subjects.

In subjects who recover, there is gradual resolution of hypoxemia and improved lung compliance and pulmonary function may be restored to normal in some subjects. In most subjects who survive ARDS, pulmonary function can take 6-12 months to be restored to nearly normal levels. Residual impairment of pulmonary mechanics may include mild restriction, obstruction, impairment of the diffusing capacity for carbon monoxide, or gas-exchange abnormalities with exercise, but these abnormalities are usually asymptomatic. Severe disease and prolonged mechanical ventilation identify patients at highest risk for persistent abnormalities of pulmonary function. Those who survive the illness have a reduced health-related quality of life as well as pulmonary-disease-specific health-related quality of life.

2. Risk Factors for ARDS

ARDS develops as a complication to acute diseases or injuries such as sepsis, pneumonia, aspiration, ischemia (circulatory arrest, hemorrhagic shock), trauma, severe asthma, poisoning, severe acute respiratory syndrome (SARS), influenza, infection e.g., by viral agents such as a coronavirus, influenza virus or Rous Sarcoma Virus (RSV), and others. Common risk factors for the development of ARDS include, but are not limited to, direct lung injury, commonly arising from pneumonia or aspiration of gastric contents and less commonly from pulmonary contusion, fat emboli, near-drowning, inhalational injury, reperfusion pulmonary edema following lung transplantation or pulmonary embolectomy. Sepsis, severe trauma with shock and multiple transfusions, cardiopulmonary bypass, drug overdose, acute pancreatitis or transfusion of blood products, can also cause indirect lung injury associated with the development of ARDS.

Overall, sepsis and multi-organ dysfunction are associated with the highest risk of progression of ARDS, with sepsis causing approximately 40-60% of morbidity. The loss of epithelial integrity in ARDS appears to contribute to alveolar flooding and leading to septic shock in patients suffering from bacterial pneumonia. The specific injury to cuboidal type II epithelial cells also disrupts normal epithelial fluid transport thereby impairing removal of edema fluid from the alveolar space, reducing the production and turnover of surfactant. Furthermore, disorganized on insufficient epithelial repair contributes to alveolar fibrosis. These factors suggest that the degree of epithelial damage and/or epithelial repair is/are important predictor(s) of outcome in ARDS patients.

3. Treatment Regimes for ARDS

Supportive care of mostly mechanical ventilation constitutes the current state of the art treatment for both ALI and ARDS patients in a critical care environment (Tobin, *New Engl. J Med* 342, 21360-21361, 2000).

Surfactant therapy, which has been successful in treatment of neonatal respiratory distress syndrome, has had no effect on oxygenation, the duration of mechanical ventilation or survival in patients suffering from ARDS in one study (Anzueto et al., *New Engl. J Med* 334, 1417-1421, 1996).

Results of randomized, double-blind studies of the effects of inhaled nitric oxide to cause pulmonary vasodilation have been discouraging, having no positive effect on outcome (e.g., Rossiant et al., *New Engl J Med* 328, 399-405, 1993; Dellinger et al., *Crit. Care Med.* 26, 15-23, 1998; Payen et al., *Intensive Care Med.,* 25 Suppl. S166, abstract).

Glucocorticoids, such as methylprednisolone, alprostadil and ketoconazole, appear to be largely unsuccessful for treatment of early stage or acute ARDS, however may assist in treatment of fibrosing alveolitis (Bernard et al., *New Engl J Med* 317, 1565-1570, 1987; Luce et al., *Am. Rev. Respir. Dis.* 136, 62-68, 1998; Sprung et al., *New Engl J Med* 311, 1137-1143, 1984; Meduri et al., *Chest* 100, 943-952, 1991; Meduri et al., *Chest* 105, 1516-1527, 1994; Meduri et al., *JAMA* 280, 159-165, 1998). Methylprednisolone also has the significant adverse effect of increasing the incidence of infection when used at high dosage.

Immunologic approaches to the treatment of sepsis, ARDS and MOF have been described which are directed at the inflammatory cascade, either to the inciting event or insult e.g., endotoxin, the mediators e.g., IL-1 or TNF-α, or to the effector cells e.g., neutrophils. However, no efficacious therapy has been identified based upon these approaches.

Thus, it is widely accepted that no pharmacological intervention has been demonstrated to reduce morbidity and mortality of patients with ARDS or its associated disorders such as ALI e.g., caused by sepsis. There is often a delay between a precipitating factor e.g., trauma, poisoning, viral infection, etc and the onset of ARDS.

Peptide Therapeutics for Non-ARDS-Related Conditions

It is known that proteins bind to other proteins, antigens, antibodies, nucleic acids, and carbohydrates. Such binding enables the protein to effect changes in a wide variety of biological processes in all living organisms. As a consequence, proteins represent an important source of natural modulators of phenotype. Accordingly, peptides that modulate the binding activity of a protein may represent attractive lead compounds (drug candidates) in primary or secondary drug screening. For example, the formation of a target biological interaction that has a deleterious effect (e.g. replication of a pathogen or of a cancer cell), can be assayed to identify lead compounds that antagonize the biological interaction.

Peptide therapeutics may provide advantages over nucleic acid-based therapeutics e.g., DNAzymes and DNA decoys, in terms of stability and consistent delivery.

Antibodies represent the fastest growing class of approved drugs in this area, however they require complex and expensive synthesis and are difficult to deliver via non-injectable routes. Furthermore, intracellular delivery of peptides is also now possible in vivo using protein transduction domains. These advances make peptide-based therapeutics an attractive alternative to antibody-based therapeutics.

Existing drawbacks associated with peptide-based therapeutics include their low affinity, high turnover in vivo and difficulties in their isolation compared to small molecules. For example, peptides that target protein interaction interfaces which may be large and relatively featureless are generally more difficult to produce and isolate when compared to small molecule inhibitors of enzyme-active sites that generally form small complex pockets. Accordingly, it is not facile to identify peptides that address these problems.

For example, random peptide libraries, e.g., synthetic or genetically-produced mimetic or mimotope libraries, can be produced using short random oligonucleotides produced by synthetic combinatorial chemistry, cloned into an appropriate vehicle for expression, and the encoded peptide screened using one of a variety of approaches. Alternatively, random peptide libraries can be produced by synthetic peptide chemistry in parallel format. However, the ability to isolate active peptides from random fragment libraries can be highly variable with low affinity interactions occurring between the peptide-binding partners. Moreover, the expressed peptides often show little or none of the secondary or tertiary structure required for efficient binding activity, and/or are unstable. This is not surprising, considering that biological molecules appear to recognize shape and charge rather than primary sequence (Yang and Honig *J. Mol. Biol.* 301(3), 691-711 2000) and that such random peptide aptamers are generally too small to comprise a protein domain or to form the secondary structure of a protein domain. Protein folds are understood in the art to mean independently folding peptide structures (i.e. a "subdomain"), e.g., a 19-residue fragment from the C-loop of the fourth epidermal growth factor-like domain of thrombomodulin as been described by Alder et al, *J. Biol. Chem.,* 270: 23366-23372, 1995. Looser secondary structures have also been described which are predisposed to form folds on the surface of a partner protein. The relatively unstructured 'linear' nature of these peptide aptamers also leads to their more rapid degradation and clearance following administration to a subject in vivo, thereby reducing their appeal as therapeutic agents.

To enhance the probability of obtaining useful bioactive peptides or proteins from random peptide libraries, peptides have previously been constrained within scaffold structures, e.g., thioredoxin (Trx) loop (Blum et al. *Proc. Natl. Acad. Sci. USA,* 97, 2241-2246, 2000) or catalytically inactive staphylococcal nuclease (Norman et al, *Science,* 285, 591-595, 1999), to enhance their stability. Constraint of peptides within such structures has been shown, in some cases, to enhance the affinity of the interaction between the expressed peptides and its target, presumably by limiting the degrees of conformational freedom of the peptide, and thereby minimizing the entropic cost of binding.

Recently, peptide mimotopes of less than about 50 amino acids in length from biodiverse genomic sources have been described that are capable of forming protein sub-domains by virtue of assuming conformations sufficient for binding to a target protein or target nucleic acid ("Phylomer™ peptides", Phylogica, Perth, western Australia, Australia) e.g., International Patent Application No. PCT/AU00/00414 and US Patent Publication No. 2003-0215846 A1. Such Phylomer™ peptides show promise in overcoming the existing drawings associated with peptide therapeutics. The conformation(s) of such Phylomer™ peptides is a product of secondary and/or tertiary structural features and, by virtue of the peptide binding to its target protein or protein interaction interface is compatible with, albeit not necessarily iterative of, the target protein(s) or target protein interaction interface. Such secondary and super-secondary structural features may suggest that Phylomer™ peptides could, on average, have higher substrate affinities and longer half-lives than more conventional random peptides. On the other hand, Phylomer™ peptides may also provide production and delivery advantages compared to antibody-based and other protein-based therapies by virtue of their small size. Additionally, because Phylomer™ peptides are derived from libraries comprising mixtures of small genome fragments from evolutionarily-diverse bacteria and/or eukaryotes having small albeit well-characterized genomes, they can be screened in silico to select against those peptides that are likely, because of their known function e.g., known toxins or allergens, to produce adverse reactions in recipient mammals, including humans. Similarly, if the Phylomer™ peptides specific for a particular target are identified through an intracellular screening method e.g., yeast two hybrid screening, those peptides which are generally toxic to cells may be eliminated from the screen because they kill the assay cells. Notwithstanding the need for empirical testing of therapeutic products, this "safety" feature of Phylomer™ peptides provides a significant potential advantage over peptides derived from mammals, including antibodies. In addition, since these Phylomer sequences did not evolve in order to bind to a human target with an intermediate affinity compatible with most biological function(s), the potential exists for identifying extremely high affinity interactors with the target which can outcompete natural partners of that target.

Conventional techniques of molecular biology, microbiology, virology, recombinant DNA technology, peptide synthesis in solution, solid phase peptide synthesis, and immunology are described, for example, in the following texts that are incorporated by reference:

Sambrook, Fritsch & Maniatis, Molecular Cloning: A Laboratory Manual, Cold Spring Harbor Laboratories, New York, Second Edition (1989), whole of Vols I, II, and III;

DNA Cloning: A Practical Approach, Vols. I and II (D. N. Glover, ed., 1985), IRL Press, Oxford, whole of text;

Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;

Animal Cell Culture: Practical Approach, Third Edition (John R. W. Masters, ed., 2000), ISBN 0199637970, whole of text;

Perbal, B., A Practical Guide to Molecular Cloning (1984);

Methods In Enzymology (S. Colowick and N. Kaplan, eds., Academic Press, Inc.), whole of series;

J. F. Ramalho Ortigão, "The Chemistry of Peptide Synthesis" In: Knowledge database of Access to Virtual Laboratory website (Interactiva, Germany);

Barany, G. and Merrifield, R. B. (1979) in *The Peptides* (Gross, E. and Meienhofer, J. eds.), vol. 2, pp. 1-284, Academic Press, New York.

Bodanszky, M. (1984) *Principles of Peptide Synthesis*, Springer-Verlag, Heidelberg.

Bodanszky, M. & Bodanszky, A. (1984) *The Practice of Peptide Synthesis*, Springer-Verlag, Heidelberg.

Bodanszky, M. (1985) *Int. J. Peptide Protein Res.* 25, 449-474.

Golemis (2002) Protein-Protein Interactions: A Molecular Cloning Manual(Illustrated), Cold Spring Harbor Laboratory, New York, ISBN 0879696281.

Smith et al., (2002) Short Protocols in Molecular Biology: A Compendium of Methods from Current Protocols in Molecular Biology, 5th Edition (Illustrated), John Wiley & Sons Inc., ISBN 0471250929.

Sambrook and Russell (2001) Molecular Cloning, Cold Spring Harbor Laboratory, New York, ISBN 0879695773.

SUMMARY OF INVENTION

1. Introduction

The present invention is based upon the identification by the inventors of compositions e.g., peptidyl compositions and non-peptidyl compositions that reduce neutrophilic-inflammation in a mouse model of ARDS or sepsis. As used herein, the term "neutrophilic inflammation" shall be taken to include neutrophil activation and/or infiltration into the lung and any direct or indirect consequence thereof in the development of ARDS or a side effect of ARDS e.g., vascular leakage of plasma proteins into the alveolar spaces of the lungs alveolar filling, lung edema, loss of epithelial integrity in alveoli, alveolar flooding, septic shock, impaired removal of edema fluid from the alveolar space, reduced surfactant production, reduced turnover of surfactant, disorganized on insufficient epithelial repair, alveolar fibrosis, hypoxemia, increased alveolar dead space, decrease in alveolar compliance, micro thrombus formation in multiple organs e.g., lungs and kidneys, pulmonary hypertension, ventricular failure or pneumothorax.

For example, such peptidyl compositions reduce neutrophilic inflammation e.g., selected individually or collectively from the AP-1 signalling inhibitory peptides and AP-1 signalling inhibitory peptide analogs set forth in the Sequence Listing e.g., a peptide selected from the group consisting of:
(a) a peptide encoded by a nucleic acid comprising a sequence set forth in any one of SEQ ID NOs: 1-25;
(b) a peptide comprising a sequence set forth in any one of SEQ ID NOs: 26-72, 121-124, 129 or 131; and
(c) an analog of (a) or (b) selected from the group consisting of (d) the sequence of (a) or (b) comprising one or more naturally-occurring amino acid substitutions; (e) the sequence of (a) or (b) comprising one or more non-naturally-occurring amino acid analogs; (f) an isostere of (a) or (b); (g) a retro-peptide or retro-inverted peptide analog of (a) or (b);

or more particularly, e.g., the retroinverted peptide analogs designated as PYC35, PYC36 and PYC38/39 or said peptide analog conjugated to a transport peptide such as TAT or retro-TAT. In this example, neutrophilic inflammation is determined by the percentage of neutrophils in bronchoalveolar lavage (BAL) when administered to animals in which ARDS is induced by inhalation of lipopolysaccharide (LPS).

The data herein are consistent with therapeutic function for the peptides in the prophylactic and therapeutic treatment of ARDS and complications thereof, and for the prophylactic treatment of clinical disorders associated with the development of ARDS.

The data herein are also consistent with the use of the peptides to produce peptide formulations, especially injectable or intranasal formulations, for prophylactic and/or therapeutic intervention in ARDS and complications thereof, and for the prophylactic treatment of clinical disorders associated with the development of ARDS. In one example, the present invention provide for a use of a peptidyl inhibitor of AP-1 signalling in the preparation of a medicament for the treatment of ARDS or for treatment of a complication associated with ARDS or for the prevention of ARDS or for the treatment of a clinical disorder associated with the development of ARDS.

In the present context, the term "clinical disorders associated with the development of ARDS" shall be taken to mean any risk factor associated with ARDS or a condition causing lung damage capable of leading to ARDS or its complications such as, for example, infection, asthma, poisoning, sepsis, pneumonia, aspiration, ischemia (circulatory arrest, hemorrhagic shock), trauma, pulmonary contusion, fat emboli, near-drowning, inhalational injury, reperfusion pulmonary edema following lung transplantation or pulmonary embolectomy, cardiopulmonary bypass, drug overdose, acute pancreatitis or transfusion of blood products. A number of key proteins are implicated in the pathway of inflammation in ARDS e.g., Toll-like receptor-4 (TLR4), the adaptor proteins for TLR4 designated Mal and MYD88, Pak1 and NF-κB.

Without being bound by any theory or mode of action, the present invention also provides for utility of AP-1 signaling inhibitors generally in reducing or preventing neutrophilic inflammation in the treatment or prophylaxis of ARDS, or in the development of ARDS. This is because the peptides supra were described as AP-1 signaling inhibitors by the assignee of the inventors, based on reverse hybrid screening technology using c-Jun as a bait.

The peptides supra inhibit AP-1 signaling by indirect means e.g., involving factors upstream of c-Jun that are conserved between yeasts and mammals, or by direct means involving inhibition of c-Jun dimerization with c-Jun or other proteins. For example, yeast cells possess a stress-responsive MAPK (SAPK) cascade; a multistep phosphorelay system; and AP-1-like transcription factor (Yap1) that govern the response of yeasts to oxidative stress (Ikner et al., *Mutation Res.* 569, 13-27, 2005), and which may be involved in regulating the apoptotic response to cytotoxic compounds used in the reverse hybrid screens. The yeast MAPK (SAPK) cascade involves signaling from a complex comprising yeast homologs of human Cdc42 and Pak1 (i.e., Cdc42 and Step 20, respectively) to the MAPKKK Ste11, which regulates the MAPKK Pbs2 and, in turn, the MAPK Hog1 to regulate gene expression, membrane transport, cell cycle progression, etc. The yeast phosphorelay system appears to converge on Pbs2 MAPKK of the Hog1 SAPK cascade and is initiated by the transmembrane protein Sho1 which activates Pbs2 through the MAPKKK Ste11 of the Hog1 SAPK cascade. The AP-1-like transcription factor (Yap1) appears to serve as an oxidative stress sensor that directly regulates transcription albeit independently of the SAPK pathway. Without being bound by any theory or mode of action, the present inventors reason that a Phylomer™ peptide identified in reverse hybrid screening of yeast cells may rescue yeast cells from an event upstream of Hog1 in yeast that would otherwise lead to activation of these stress responses leading to cell death. If the same Phylomer™ peptide also recognizes a homologous mammalian AP-1 pathway component upstream of c-Jun and/or JNK, inhibition of that component would also explain the observed reduction in AP-1 mediated activation of luciferase reporter gene expression observed in mammalian cells.

Accordingly, the peptides supra are designated herein as "AP-1 signaling inhibitors" or "AP-1 complex formation inhibitors" or "AP-1 signaling inhibitors" or similar term. It is to be understood that such terminology includes the direct c-Jun dimerization and/or upstream indirect effects e.g., acting on phosphorylation of MAPKK, JNK, Cdc42, Pak1 or Rac1, or dimerization of Cdc42, Pak1 or Rac1 in mammalian cells. Preferred AP-1 signaling inhibitory peptides will inhibit later steps in the AP-1 signaling pathway e.g., c-Jun dimerization, to thereby provide greater specificity than, for example, a JNK inhibitory peptide.

It is also to be understood that the term "c-Jun dimerization" includes c-Jun self-dimerization or homodimerization, and heterodimerization between c-Jun and another protein e.g., ATF-2, c-Fos or JNK and preferably between c-Jun and ATF-2 or between c-Jun and c-Fos (i.e., a c-Jun heterodimer) or an analog of said isolated peptide or protein domain.

Thus, the data herein are suggestive of the utility of AP-1 signaling inhibitors generally for the prophylactic and therapeutic treatment of ARDS and complications thereof, and for the prophylactic treatment of clinical disorders associated with the development of ARDS.

2. Specific Embodiments

The scope of the invention will be apparent from the claims as filed with the application that follow the examples. The claims as filed with the application are hereby incorporated into the description. The scope of the invention will also be apparent from the following description of specific embodiments.

In one example, the present invention provides a peptide formulation comprising:
(i) an amount of a peptide or analog thereof sufficient to reduce neutrophilic inflammation wherein a peptide or analog is selected individually or collectively from the group consisting of:
(a) a peptide encoded by a nucleic acid comprising a sequence set forth in any one of SEQ ID NOs: 1-25;
(b) a peptide comprising a sequence set forth in any one of SEQ ID NOs: 26-72, 121-124, 129, 131 or 163; and
(c) an analog of (a) or (b) selected from the group consisting of (d) the sequence of (a) or (b) comprising one or more naturally-occurring amino acid substitutions; (e) the sequence of (a) or (b) comprising one or more non-naturally-occurring amino acid analogs; (f) an isostere of (a) or (b); (g) a retro-peptide or retro-inverted peptide analog of (a) or (b); and
(ii) a suitable carrier or excipient e.g., a carrier or excipient is a carrier or excipient.

In one example, the formulation is for inhalation and the subject peptide is present in an amount suitable for administration by inhalation and the carrier or excipient is one suitable for inhalation. Inhalable formulations are preferred for prophylactic applications e.g., for administration to an asymptomatic subject at risk of developing ARDS or a complication associated therewith e.g., an asymptomatic subject having one or more risk factors for ARDS supra, and/or an asymptomatic subject exposed to an infectious agent, poison, allergen or irritant of the airways that is a risk factor for development of ARDS.

By "asymptomatic subject" is meant a subject that does not exhibit one or more symptoms associated with an acute phase of ARDS or breathing difficulty associated with ARDS.

In another example, the formulation is for injection and the subject peptide is present in an amount suitable for administration by injection e.g., subcutaneously, intravenously, intraperitoneally or intramuscularly, and the carrier or excipient is one suitable for injection e.g., subcutaneously, intravenously, intraperitoneally or intramuscularly. Injectable formulations are preferred for acute phase ARDS or complications associated therewith or in a non-acute phase where the subject has difficulty inhaling.

By "individually" is meant that the invention encompasses the recited peptides or groups of peptides separately, and that, notwithstanding that individual peptides or groups of peptides may not be separately listed herein the accompanying claims may define such peptides or groups of peptides separately and divisibly from each other.

By "collectively" is meant that the invention encompasses any number or combination of the recited peptides or groups of peptides, and that, notwithstanding that such numbers or combinations of peptides or groups of peptides may not be specifically listed herein the accompanying claims may define such combinations or sub-combinations separately and divisibly from any other combination of peptides or groups of peptides.

Preferred formulations will comprise a peptide analog of a peptide selected individually or collectively from the group consisting of peptides designated as PYC35, PYC36 and PYC38/39, and more preferably one or more retroinverted peptide analogs s comprising a sequence selected from the group consisting of SEQ ID NOs: 103, 104, 105, 106, 107, and 108 and mixtures thereof.

It is to be understood that it is a preferred embodiment for the peptidyl formulations of the present invention to have AP-1 signaling inhibitory activity conferred by the peptide component or peptide analog component of such formulations.

In an alternative embodiment, the present invention provides a formulation comprising (i) an amount of an AP-1 signaling inhibitor sufficient to reduce neutrophilic inflammation; and (ii) a suitable carrier or excipient e.g., a carrier or excipient for inhalation or injection. The formulation may be packaged for multiple administrations e.g., it may be packaged as multiple injectable ampoules, capsules, etc. for repeated administration or repeated dosing.

Preferably, an inhibitor of AP-1 signaling interacts with JNK or a nucleic acid encoding same to reduce expression and/or activity thereof. For example, an inhibitor interacts with JNK and prevents JNK from phosphorylating a protein, such as, for example, c-Jun and/or ATF2 and/or c-Fos and/or Bcl-$X_L$ and/or Bim and/or Bmf.

Alternatively, or in addition, an inhibitor of JNK-mediated signaling interacts with and reduces or prevents activity of another molecule involved in JNK-mediated signal transduction. Suitable molecules will be apparent to the skilled artisan and/or described herein. For example, an inhibitor inhibits and/or reduces activity and/or expression of a molecule that interacts with JNK, e.g., a protein phosphorylated and/or activated by JNK or nucleic acid encoding same and prevents activity or expression of that molecule. For example, an inhibitor reduces or prevents the expression and/or activity of c-Jun, ATF2, c-Fos and/or NFAT4. For instance, an inhibitor reduces or prevents formation of a heterodimer and/or homodimer comprising c-Jun.

The AP-1 signaling inhibitor may be a peptidyl or non-peptidyl composition. Suitable peptidyl compounds will be any one or more of the peptides described herein above, or alternatively a different peptide or antibody composition that inhibits AP-1 signaling e.g., as described in the ensuing Detailed Description. Suitable non-peptidyl compounds will be apparent to the skilled artisan based on the description herein, and include, for example, a nucleic acid, or a small molecule.

Preferably, the inhibitor is a retro-inverted peptide analog capable of inhibiting or reducing AP-1 signaling. For example, the retro-inverted peptide analog comprises an amino acid sequence set forth in any one of SEQ ID NOs: 73-120, 125-128, 130, 164 or 165. In one exemplified form of the invention, the retro-inverted peptide analog comprises an amino acid sequence set forth in SEQ ID NO: 103 or SEQ ID NO: 104 or SEQ ID NO: 105 or SEQ ID NO: 106 or SEQ ID NO: 107 or SEQ ID NO: 108.

Again, the present invention clearly encompasses formulations comprising mixtures of such peptide analogs.

In one example, a peptide or analog as described herein above or a peptidyl AP-1 signaling inhibitor, is conjugated to or fused to a protein transduction domain. A suitable protein transduction domain will be apparent to the skilled artisan based on the description herein and includes a HIV-tat basic region peptide (e.g., comprising a sequence set forth in any one of SEQ ID NOs: 137-143) or a retroinverted analog thereof (e.g., comprising a sequence set forth in any one of SEQ ID NOs: 144-152). Another suitable protein transduction domain is a Kaposi fibroblast growth factor (FGF) hydrophobic peptide protein transduction domain (e.g., comprising an amino acid sequence set forth in SEQ ID NO: 159 or 160) or a retro-inverted analog thereof (e.g., comprising an amino acid sequence set forth in SEQ ID NO: 161 or 162).

The skilled artisan will be aware that an amount of the active ingredient suitable for reducing neutrophilic inflammation will vary, e.g., as a result of variation in the bioactivity of an inhibitor, and/or the severity of the inflammatory response that would be elicited in the absence of treatment. Accordingly, this term is not to be construed to limit the invention to a specific quantity, e.g., weight of active ingredient.

In one example, a formulation as described herein according to any embodiment comprises an amount of a peptide or analog as described herein above or AP-1 signaling inhibitor sufficient to additionally enhance or induce alveolar re-epithelialization in a subject that has suffered alveolar epithelial injury e.g., sufficient epithelial repair to prevent or reduce fibrosis. As used herein, the term "re-epithelialization" shall be taken to mean the process by which one or more alveolar epithelial cell types or layer is produced over and/or within injured tissue. In another example, the formulations described herein according to any embodiment comprise an amount of a peptide or analog as described herein above or an inhibitor of JNK-mediated signal transduction sufficient to enhance or induce re-epithelialization of injured alveolar tissue with reduced scar formation, e.g., compared to tissue to which the inhibitor has not been applied. In another example, the formulations described herein prevent or reduce alveolar epithelial loss or damage in a subject that has not yet suffered significant damage to the alveolar epithelium because e.g., the subject has one or more risk factors for acute lung injury and/or ARDS but has not suffered the acute phase of ARDS at the time of administration of the formulation or has recovered from acute lung injury or ARDS and is at risk of subsequent attacks from the condition(s).

As used herein, the term "suitable carrier or excipient" shall be taken to mean a compound or mixture thereof that is suitable for use in a formulation albeit not necessarily limited in use to that context. In contrast, the term "a carrier or excipient" is compound or mixture thereof that is described in the art only with reference to a use in a formulation. The term "carrier or excipient for inhalation" shall be taken to mean a compound or mixture thereof that is suitable for use in a formulation to be administered to a subject by inhalation. The term "carrier or excipient for injection" shall be taken to mean a compound or mixture thereof that is suitable for use in a formulation to be administered to a subject by injection.

A carrier and excipient useful in the formulation of the present invention will generally not inhibit to any significant degree a relevant biological activity of the active compound e.g., the carrier or excipient will not significantly inhibit the activity of the active compound with respect to reducing neutrophilic inflammation. Alternatively, or in addition, the carrier or excipient comprises a compound that enhances uptake and/or delivery and/or efficacy of the active compound.

Alternatively, or in addition, the carrier or excipient comprises a compound that enhances the activity of a peptide or analog as described herein above or, more generally, an AP-1 signaling inhibitor and/or reduces inhibition of said peptide or analog or AP-1 signaling inhibitor by degradative enzymes in the site of administration such as the mucosa, and/or en route to the site of action such as the airways or lung tissue of a subject and or at the site of action such as the alveoli. For example, the carrier or excipient may comprise a protease inhibitor and/or a DNase inhibitor and/or an RNase inhibitor to thereby enhance the stability of a peptide or analog as described herein above or a peptidyl AP-1 signaling inhibitor.

In one example, the formulation as described herein according to any embodiment comprises an additional compound, such as, for example, a growth factor to further enhance or induce alveolar re-epithelialization or to further prevent or inhibit epithelial damage or loss and/or an antibiotic and/or an anaesthetic. Suitable additional compounds will be apparent to the skilled artisan based on the description herein.

The present invention also provides a formulation comprising (i) an amount of a retroinverted peptide comprising an amino acid sequence set forth in SEQ ID NO: 103 or SEQ ID NO: 104 or SEQ ID NO: 105 or SEQ ID NO: 106 or SEQ ID NO: 107 or SEQ ID NO: 108 sufficient to reduce or prevent neutrophilic inflammation and/or enhance or induce alveolar re-epithelialization preferably with reduced scar formation in a subject that has suffered alveolar epithelial injury, and/or prevent or reduce alveolar epithelial loss or damage in a subject that has not yet suffered significant damage to the alveolar epithelium; and (ii) a suitable carrier or excipient e.g., a carrier or excipient for inhalation or injection.

The present invention also provides a method for producing a formulation described herein according to any embodiment. For example, such a method comprises mixing or otherwise combining a peptide or analog as described herein above or AP-1 signaling inhibitor in an amount sufficient to reduce or prevent neutrophilic inflammation and/or enhance or induce alveolar re-epithelialization preferably with reduced scar formation in a subject that has suffered alveolar epithelial injury, and/or to prevent or reduce alveolar epithelial loss or damage in a subject that has not yet suffered significant damage to the alveolar epithelium, with a suitable carrier or excipient e.g., a carrier or excipient for inhalation or injection.

In one example, the method additionally comprises producing or obtaining said peptide or analog or AP-1 signaling inhibitor. For example, a peptide or analog or AP-1 signaling inhibitor is produced synthetically or recombinantly, using a method known in the art and/or described herein.

The present invention also provides a method of treatment of ARDS and/or one or more complications thereof or for the prophylactic treatment of one or more clinical disorders associated with the development of ARDS, the method comprising administering to a subject in need thereof a formulation comprising an AP-1 signaling inhibitor e.g., as described herein according to any embodiment, for a time and under conditions sufficient to reduce or prevent neutrophilic inflammation and/or enhance or induce alveolar re-epithelialization preferably with reduced scar formation in a subject that has suffered alveolar epithelial injury, and/or prevent or reduce alveolar epithelial loss or damage in a subject that has not yet suffered significant damage to the alveolar epithelium.

There is often a delay between a precipitating factor e.g., trauma, poisoning, viral infection, etc and the onset of ARDS, which the inventors reason provides a window of opportunity for administering a formulation of the invention or other formulation comprising an AP-1 signaling inhibitor. Accordingly, in one example, this invention provides a method for the prophylaxis or prevention of ARDS comprising administering to a subject at risk of developing ARDS or exposed to one or more risk factors of ARDS a formulation comprising an AP-1 signaling inhibitor e.g., a formulation according to any embodiment hereof for a time and under conditions sufficient to prevent neutrophilic inflammation and/or prevent alveolar epithelial loss or damage in the subject. In one example, the subject is capable of inhaling the formulation and the formulation is administered to the subject by inhalation. In another example, the formulation is administered by injection.

In another example, the present invention provides a method of treatment of ARDS and/or one or more complications thereof comprising administering to a subject in need thereof a formulation comprising an AP-1 signaling inhibitor e.g., a formulation according to any embodiment hereof for a time and under conditions sufficient to reduce neutrophilic inflammation and/or enhance or induce alveolar re-epithelialization, preferably with reduced scar formation, in a subject that has suffered alveolar epithelial injury. In one example, the subject is suffering from breathing difficulty and/or has reduced breathing capability and the formulation is administered to the subject by injection e.g., by an intravenous, intraperitoneal, intramuscular or subcutaneous route.

As used herein the term "treatment" includes therapeutic treatment of a subject who has already suffered ARDS or a complication thereof including neutrophilic inflammation and its downstream consequences such as, for example, alveolar filling, alveolar epithelial damage or loss, amongst others, and prophylactic treatment of a subject having one or more risk factors for ARDS but that has not yet suffered an acute phase of ARDS or a complication thereof. In this respect, it will be evident that the reduction of neutrophilic inflammation and enhancement/induction of alveolar re-epithelialization are more pertinent to therapeutic regimens, and that the prevention of neutrophilic inflammation and/or the prevention or reduction of alveolar epithelial injury or loss are more pertinent to prophylactic regimens. Consistent with this construction, the term "prevent" or "prevention" as used throughout this specification shall not be taken to require an absolute i.e., 100% abrogation of neutrophilic inflammation or epithelial damage/loss in a subject, and it is sufficient that there is a significant reduction in these adverse consequences of ARDS using the method and formulations of the present invention compared to the absence of treatment in accordance with the present invention. Similarly, the term "reduction" or "reduce" as used throughout this specification shall not be taken to require an abrogation of neutrophilic inflammation or epithelial damage/loss in a subject more than a significant effect compared to the absence of treatment in accordance with the present invention. Similarly, the terms "enhance", "enhancement", "induce" and "induction" as used throughout this specification shall not be taken to require any particular quantitative change, merely an improvement that is significant compared to the absence of treatment in accordance with the present invention. The term "enhance" and "enhancement" will be understood or taken to mean an increase in the level or amount of a stated integer that is already present whereas the terms "induce" and "induction" refer to the increase in level or amount of an integer that is not detectable prior to the induction, however may be present in undetectable amounts.

As used herein, the term "administer" shall be taken to mean that a formulation is applied to the respiratory system of a subject including the nasal passage, buccal cavity, throat or eosophagus or lung, by inhalation and/or applied to the circulatory system of a subject by injection intramuscularly, subcutaneously, intravenously, intraperitoneally etc, including single or repeated or multiple dosages by any administration route. As used herein the term "inhalation" shall be taken to include "aspiration".

As used herein, the term "subject in need thereof" shall be taken to mean a subject that has developed or suffers from ARDS or one or more complications thereof or is predisposed by virtue of having one or more risk factors to suffering from ARDS or one or more complications thereof. In one example, the subject has already suffered from ARDS or neutrophilic inflammation or one or more downstream effects thereof and/or has suffered alveolar epithelial loss or injury. In another example, the subject has not yet suffered significant impairment of breathing or significant damage to the alveolar epithelium and has one or more risk factors for ARDS or acute lung injury or a complication thereof.

The present invention clearly contemplates repeated administration of a formulation as described herein according to any embodiment in the therapy or prophylaxis of ARDS and complications thereof. For example, repeated injection and/or inhalation of a formulation of the present invention may be required to reduce or prevent inflammatory responses in the lung for a long period of time, e.g., during sepsis or persistent or long term infection by a bacterial agent or virus or when a subject is immune suppressed e.g., by virtue of post-transplant drug therapy to prevent tissue rejection or immunodeficiency virus infection e.g., by HIV-1.

Repeated administration of a peptide formulation as described herein may be timed so as to ensure a sufficiently high concentration of the bioactive peptide component of the formulation in plasma of the subject and/or at the site of action in the treatment regimen. For example, second and/or subsequent doses of a peptide formulation of the invention as described according to any embodiment hereof may be administered at a time when serum concentration of a peptide provided by one or more previous doses fall(s) below a desired level at which it is active or provides sufficient benefit to the patient. Such booster doses of a peptide formulation of the present invention are clearly contemplated in the prophylaxis and/or therapy of ARDS and/or one or more complications thereof according to the present invention.

In one example, a method of treatment or prophylaxis as described herein according to any embodiment additionally comprises providing or obtaining a formulation described herein or a composition of matter forming the active ingredient of such a formulation, or information concerning said formulation or active ingredient.

For example, the present invention provides a method of treatment or prophylaxis of a subject in need thereof, said method comprising:
(i) identifying a subject suffering from ARDS and/or one or more complications thereof or one or more clinical disorders associated with the development of ARDS or is at risk of suffering from ARDS and/or one or more complications thereof or one or more clinical disorders associated with the development of ARDS;
(ii) obtaining a formulation as described herein according to any embodiment; and
(iii) administering said formulation to said subject.

In another example, the present invention also provides a method of treatment or prophylaxis of a subject in need thereof, said method comprising:
(i) identifying a subject suffering from ARDS and/or one or more complications thereof or one or more clinical disorders associated with the development of ARDS or is at risk of suffering from ARDS and/or one or more complications thereof or one or more clinical disorders associated with the development of ARDS; and
(ii) recommending administration of a formulation as described herein according to any embodiment.

In another example, the invention provides a method of treatment or prophylaxis comprising administering or recommending a formulation as described herein according to any embodiment to a subject previously identified as suffering from ARDS and/or one or more complications thereof or suffering from one or more clinical disorders associated with the development of ARDS or otherwise at risk of developing ARDS.

In another example, the invention provides a method of treatment or prophylaxis comprising administering or recommending a formulation as described herein according to any embodiment to a subject at risk of developing ARDS and/or one or more complications thereof or suffering from one or more clinical disorders associated with the development of ARDS or otherwise at risk of developing ARDS.

In another example, the invention provides a method of treatment or prophylaxis comprising:
(i) identifying a subject suffering from ARDS and/or one or more complications thereof or one or more clinical disorders associated with the development of ARDS or is at risk of suffering from ARDS and/or one or more complications thereof or suffering from one or more clinical disorders associated with the development of ARDS or otherwise at risk of developing ARDS;
(ii) obtaining a composition as described herein that reduces or prevents neutrophilic inflammation and/or enhances or induces alveolar re-epithelialization preferably with reduced scar formation and/or prevents or reduces alveolar epithelial loss or damage; (iii) formulating the composition at (ii) with a suitable carrier and/or excipient, e.g., for inhalation and/or injection, wherein said composition is in an amount sufficient to reduce or prevent neutrophilic inflammation and/or enhance or induce alveolar re-epithelialization preferably with reduced scar formation in a subject that has suffered alveolar epithelial injury, and/or prevent or reduce alveolar epithelial loss or damage in a subject that has not yet suffered significant damage to the alveolar epithelium; and
(iv) administering said formulation to said subject.

In yet another example, the present invention provides a method of treatment or prophylaxis comprising:
(i) identifying a subject suffering from ARDS and/or one or more complications thereof or one or more clinical disorders associated with the development of ARDS or is at risk of suffering from ARDS and/or one or more complications thereof or suffering from one or more clinical disorders associated with the development of ARDS or otherwise at risk of developing ARDS;
(ii) obtaining a composition as described herein that reduces or prevents neutrophilic inflammation and/or enhances or induces alveolar re-epithelialization preferably with reduced scar formation and/or prevents or reduces alveolar epithelial loss or damage;

(iii) formulating the composition at (ii) with a suitable carrier and/or excipient, e.g., for inhalation and/or injection, wherein said composition is in an amount sufficient to reduce or prevent neutrophilic inflammation and/or enhance or induce alveolar re-epithelialization preferably with reduced scar formation in a subject that has suffered alveolar epithelial injury, and/or prevent or reduce alveolar epithelial loss or damage in a subject that has not yet suffered significant damage to the alveolar epithelium; and (iv) recommending a formulation at (iii).

In a particularly preferred example of the present invention, the method of treatment or prophylaxis involves repeated injection of a peptide formulation of the invention wherein each injection is timed so as to ensure a sufficiently high concentration of the bioactive peptide component of the formulation in plasma of the subject in the treatment regimen and wherein the peptide is a retroinverted peptide e.g., comprising a sequence set forth in any one of SEQ ID Nos: 104, 106 or 108 or active fragment thereof, and more particularly comprising SEQ ID NO: 106 or active fragment thereof. By "active fragment" in this context is meant a fragment having AP-1 signaling inhibitory activity as defined herein. In another example, the peptide formulation is PEGylated.

The present invention also provides a method for identifying a compound for the treatment or prophylaxis of ARDS and/or one or more complications thereof or suffering from one or more clinical disorders associated with the development of ARDS, said method comprising:

(i) identifying a compound capable of inhibiting or reducing AP-1 signaling;

(ii) administering an amount of the compound identified at (i) sufficient to reduce or prevent neutrophilic inflammation and/or enhance or induce alveolar re-epithelialization preferably with reduced scar formation in a subject that has suffered alveolar epithelial injury, and/or prevent or reduce alveolar epithelial loss or damage in a subject that has not yet suffered significant damage to the alveolar epithelium;

(iii) comparing the level of neutrophilic inflammation and/or the amount of alveolar re-epithelialization and/or the amount of epithelial loss or damage in the subject at (ii) to the level of neutrophilic inflammation and/or the amount of alveolar re-epithelialization and/or the amount of epithelial loss or damage in a subject to which the compound has not been administered; and (iv) selecting a compound that reduces or prevents neutrophilic inflammation and/or enhances or induces alveolar re-epithelialization preferably with reduced scar formation in a subject that has suffered alveolar epithelial injury and/or prevents or reduces alveolar epithelial loss or damage in a subject that has not yet suffered significant damage to the alveolar epithelium thereby identifying a compound for the treatment or prophylaxis of ARDS and/or one or more complications thereof or one or more clinical disorders associated with the development of ARDS.

In one example, this method of the present invention additionally comprises:

(v) optionally, determining the structure of the compound;
(vi) optionally, providing the name or structure of the compound; and
(vii) providing the compound.

The present invention also provides a method for isolating a compound for the treatment or prophylaxis of ARDS and/or one or more complications thereof or one or more clinical disorders associated with the development of ARDS, said method comprising:

(i) identifying a mixture of compounds capable of inhibiting or reducing AP-1 signaling or a library comprising compounds capable of inhibiting or reducing AP-1 signaling;

(ii) administering said mixture or a plurality of compounds identified at (i) capable of inhibiting or reducing AP-1 signaling in an amount sufficient to reduce or prevent neutrophilic inflammation and/or enhance or induce alveolar re-epithelialization preferably with reduced scar formation in a subject that has suffered alveolar epithelial injury, and/or prevent or reduce alveolar epithelial loss or damage in a subject that has not yet suffered significant damage to the alveolar epithelium;

(iii) comparing the level of neutrophilic inflammation and/or the amount of alveolar re-epithelialization and/or the amount of epithelial loss or damage in the subject at (ii) to the level of neutrophilic inflammation and/or the amount of alveolar re-epithelialization and/or the amount of epithelial loss or damage in a subject to which the mixture or plurality of compounds has not been administered;

(iv) identifying a mixture or a plurality of compounds that reduces or prevents neutrophilic inflammation and/or enhances or induces alveolar re-epithelialization preferably with reduced scar formation in a subject that has suffered alveolar epithelial injury and/or prevents or reduces alveolar epithelial loss or damage in a subject that has not yet suffered significant damage to the alveolar epithelium; and (v) separating a compound from the mixture or plurality of compounds that reduces the level of neutrophilic inflammation and/or increases the amount of alveolar re-epithelialization and/or prevents or reduces alveolar epithelial loss or damage, thereby isolating a compound for the treatment or prophylaxis of ARDS and/or one or more complications thereof or one or more clinical disorders associated with the development of ARDS.

In one example, this method of the present invention additionally comprises:

(vi) optionally, determining the structure of the compound;
(vii) optionally, providing the name or structure of the compound; and
(viii) providing the compound.

Preferably, the term "separating" comprises the use of any chemical or biochemical purification process known in the art to fractionate the mixture of plurality of compounds coupled with assaying the fractions produced for activity with respect to neutrophilic inflammation and/or re-epithelialization and/or epithelial loss or damage, and selecting fractions having one or more of said activities.

More preferably, the term "separating" refers to a process comprises iterated use of any chemical or biochemical purification process known in the art to partially or completely purify a compound from a mixture of plurality of compounds and assaying the fractions produced in each iteration of the process for activity with respect to neutrophilic inflammation and/or re-epithelialization and/or epithelial loss or damage, and selecting at each iteration one or more fractions having one or more of said activities. Preferably, the process is repeated for n iterations wherein n is sufficient number of iterations to reach a desired purity of the compound e.g., 50% or 60% or 70% or 80% or 90% or 95% or 99%. More preferably, the process is repeated for zero to about ten iterations. As will be known to the skilled artisan, such iterations do not require iteration of precisely the same purification processes and more generally utilize different processes or purification conditions for each iteration.

In the case of a library of compounds displayed separately wherein each compound is substantially pure prior to performance of the method, such isolation results in the separation of the compound from other compounds in the library that do not have the requisite activity. In this case, the term "separating" extends to determining the activity of one library component relative to another library component and selecting a compound having the desired activity.

The present invention clearly extends to the direct product of any method of identification or isolation of a therapeutic compound described herein.

It is to be understood that an identified or isolated compound in substantially pure form i.e., free from contaminants that might cause adverse side effects or contraindications or antagonize the activity of the active compound, can be formulated into a medicament suitable for treatment of ARDS and/or one or more complications thereof or one or more clinical disorders associated with the development of ARDS. Accordingly, in one example, the present invention further provides for the use of a peptide or analog as described herein above or AP-1 signaling inhibitor in the manufacture of a medicament for the treatment of ARDS and/or one or more complications thereof or one or more clinical disorders associated with the development of ARDS. In another example, the present invention further provides for the use of a peptide or analog as described herein above or AP-1 signaling inhibitor in the manufacture of a medicament for the prevention of ARDS and/or one or more complications thereof or one or more clinical disorders associated with the development of ARDS. Preferably, the peptide or analog as described herein above or AP-1 signaling inhibitor is used in an amount sufficient to reduce or prevent neutrophilic inflammation and/or enhance or induce alveolar re-epithelialization preferably with reduced scar formation in a subject that has suffered alveolar epithelial injury and/or prevent or reduce alveolar epithelial loss or damage in a subject that has not yet suffered significant damage to the alveolar epithelium. Preferably, the medicament is an inhalable and/or injectable formulation.

3. General

This specification contains nucleotide and amino acid sequence information prepared using Patent In Version 3.3. Each nucleotide sequence is identified in the sequence listing by the numeric indicator <210> followed by the sequence identifier (e.g., <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:", followed by the sequence identifier (e.g., SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Each embodiment describing a composition comprising a peptide or peptidyl analog as described herein above or peptidyl AP-1 signaling inhibitor shall be taken to apply mutatis mutandis to a formulation comprising a retro-inverted form of that peptide or peptidyl analog or peptidyl AP-1 signaling inhibitor, e.g., comprising two or more retro-inverted amino acids. Preferably, the retro-inverted form of the peptide comprises a reversed amino acid sequence and all amino other than glycine (which is not chiral) are D-amino acids.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

Figure 1:
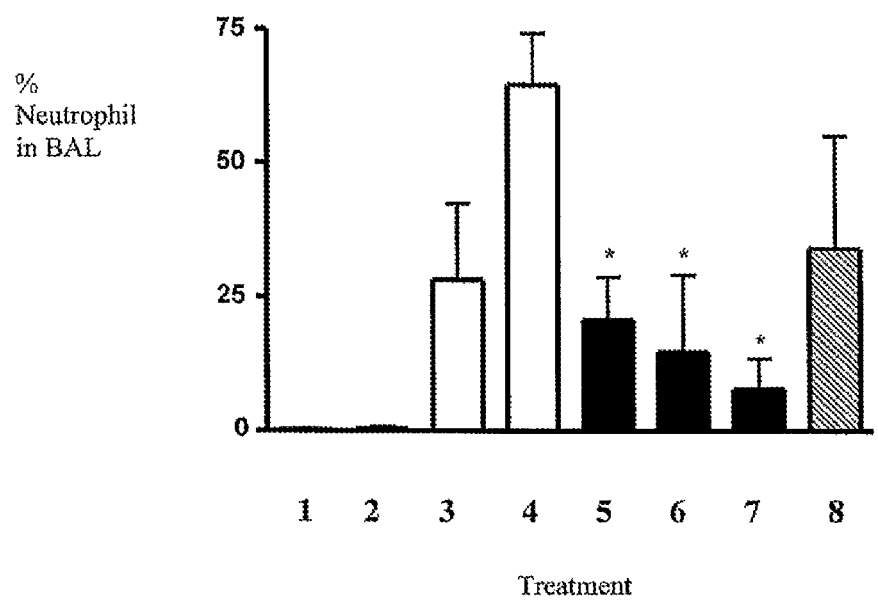
FIG. 1 is a graphical representation showing the percentage of neutrophils (y-axis) in bronchoalveolar lavage (BAL) in 8-week to 12-week old C57/BL6 mice receiving various treatments indicated by numbers on the x-axis as follows.

Columns 1-4 (open bars): Animals (n=5 per group) received either no LPS (column 1) or a dose of LPS intranasally (10 µg/mouse) and BAL was performed 1 hour (column 2), 4 hours (column 3) or 6 hours (column 4) later. No peptide was administered to these animals.

Columns 5-7 (filled bars): Animals (n=5 per group) received an intranasal dose of 10 mg/kg body weight of retroinverted peptide analog D-PYC36-TAT (SEQ ID NO: 106; column 5) or D-PYC35-TAT (SEQ ID NO: 104; column 6), or 5 mg/kg body weight of retroinverted peptide analog D-PYC38-TAT (SEQ ID NO: 108; column 7), by a repeated dose of the same peptide analog for each group co-administered intranasally with LPS (10 µg/mouse) and BAL was performed 6 hours later.

Column 8 (hatched bars): Animals (n=5) received an intranasal dose of 10 mg/kg body weight of a scrambled version of SEQ ID NO: 106 designated D-PYC36scrambled-TAT followed 1 hour later by a repeated dose of the same peptide analog co-administered intranasally with LPS (10 µg/mouse) and BAL was performed 6 hours later.

BAL was performed on the animals using 1 ml GKN/0.2% BSA. Cell counts were obtained to determine total cell numbers and differential counts were obtained on cytocentrifuge slide preparations to elucidate the percentage neutrophils in BAL. Data show mean±s.e.m. There is significantly reduced neutrophil infiltration in BAL in the presence of SEQ ID NO: 104 (p=0.0297) or SEQ ID NO: 106 (p=0.0096) or SEQ ID NO: 108 (p=0.0011), but no significant reduction in percentage neutrophils in the presence of the scrambled control peptide.

Figure 2:
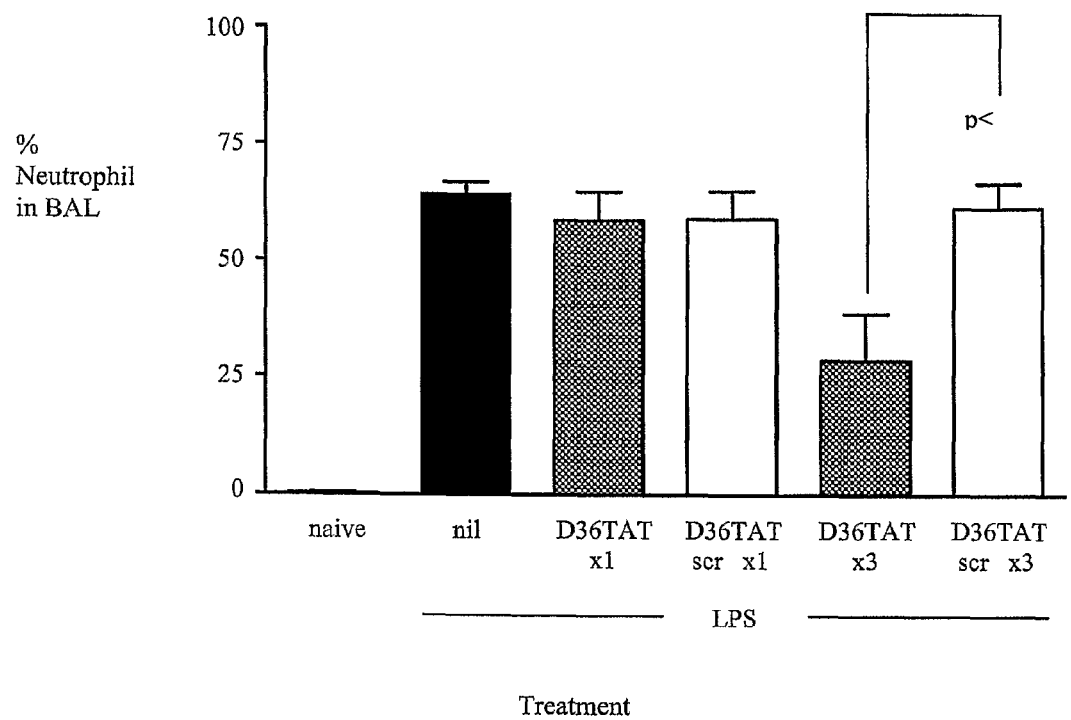

FIG. 2 is a graphical representation showing the percentage of neutrophils (y-axis) in bronchoalveolar lavage (BAL) in 8-week to 10-week old female C57/BL6 mice receiving various treatments indicated by numbers on the x-axis as follows:

Column 1 (naïve): Animals received no LPS and BAL was performed 6 hours later. No peptide was administered to these animals.

Column 2 (nil): Animals received an intranasal dose of *E. coli* LP (40 µg/mouse) and BAL was performed 6 hours later.

Column 3 (D36-TAT x1): Animals received a single intravenous injection of 10 mg/kg body weight of retroinverted peptide analog D-PYC36-TAT (SEQ ID NO: 106) followed 20 min later by an intranasal dose of LPS (40 µg/mouse). BAL was performed 6 hours after LPS administration.

Column 4 (D36-TATscr x1): Animals received a single intravenous injection of 10 mg/kg body weight of a peptide having a scrambled sequence relative to the retroinverted peptide analog D-PYC36-TAT (SEQ ID NO: 106) followed 20 min later by an intranasal dose of LPS (40 µg/mouse). BAL was performed 6 hours after LPS administration.

Column 5 (D36-TAT x3): Animals received a single intravenous injection of 10 mg/kg body weight of retroinverted peptide analog D-PYC36-TAT (SEQ ID NO: 106) followed 20 min later by an intranasal dose of LPS (40 µg/mouse), and two further intravenous injections of the same peptide at 2 hours post-LP treatment and 4 hours post-LPS treatment. BAL was performed 6 hours after LPS administration.

Column 6 (D36-TATscr x3): Animals received a single intravenous injection of 10 mg/kg body weight of a peptide having a scrambled sequence relative to the retroinverted peptide analog D-PYC36-TAT (SEQ ID NO: 106) followed 20 min later by an intranasal dose of LPS (40 µg/mouse), and two further intravenous injections of the same peptide at 2 hours post-LP treatment and 4 hours post-LPS treatment. BAL was performed 6 hours after LPS administration.

Cell counts were obtained to determine total cell numbers and differential counts were obtained on cytocentrifuge slide preparations to elucidate the percentage neutrophils in BAL. Data show mean±s.e.m. There is significantly reduced neutrophil infiltration in BAL in the presence of SEQ ID NO: 106 when administered before and after induction of ARDS in the animal model, but no significant reduction in percentage neutrophils in the presence of the scrambled control peptide.

DETAILED DESCRIPTION OF THE PREFERRED EMBODIMENTS

Peptides and Analogs

The peptides and analogs used in the formulations described herein are readily derived from the scope of peptidyl inhibitors of AP-1 signaling and analogs described below.

AP-1 Signaling Inhibitors

The compositions as described herein according to any embodiment may comprise any one or more AP-1 signaling inhibitors.

1. Non-Peptidyl Inhibitors of AP-1 Signaling

In one example of the invention, a non-peptidyl inhibitor of AP-1 signaling comprises nucleic acid that reduces or prevents expression of a protein or nucleic acid required for AP-1 signaling.

In this respect, the term "expression" will be understood by the skilled artisan to include transcription and/or translation. Accordingly, an inhibitor that reduces expression inhibits transcription and/or inhibits translation.

For example, an AP-1 signaling inhibitor reduces or prevents expression of JNK. For example, the inhibitor comprises nucleic acid such as, for example, an antisense nucleic acid, peptide nucleic acid (PNA), ribozyme, or small interfering RNA (siRNA), short hairpin RNA (shRNA) which is complementary, in whole or in part, to a target molecule comprising a sense strand, and can hybridize with a target molecule, e.g., JNK-encoding mRNA. When introduced into a cell using suitable methods, such a nucleic acid inhibits the expression of the JNK gene encoded by the sense strand. Antisense nucleic acid, ribozymes (e.g., Cech et al., U.S. Pat. No. 4,987,071; Cech et al., U.S. Pat. No. 5,116,742; Bartel and Szostak, *Science* 261, 1411-1418, 1993), nucleic acid capable of forming a triple helix (e.g., Helene, *Anticancer Drug Res.* 6, 569-584, 1991), PNAs (Hyrup et al., *Bioorganic & Med. Chem.* 4, 5-23, 1996; O'Keefe et al., *Proc. Natl Acad. Sci. USA* 93, 14670-14675, 1996), small interfering RNAs or short hairpin RNAs may be produced by standard techniques known to the skilled artisan, based upon the sequences disclosed herein. Examples of suitable siRNA include a siRNA comprising a sequence set forth in SEQ ID NO: 135 or 136.

In another example of the invention, an AP-1 signaling inhibitor reduces or prevents expression of a nucleic acid, peptide, polypeptide or protein that is phosphorylated and/or activated by JNK. For example, the inhibitor reduces or prevents expression of a protein such as, for example, c-Jun, ATF2 or c-Fos. An example of a suitable nucleic acid inhibitor is a DNAzyme designated Dz13 comprises a nucleotide sequence set forth in SEQ ID NO:133. This DNAzyme has been previously shown to be capable of reducing expression of c-Jun in Khachigian et al., *J. Biol. Chem.*, 277: 22985-22991, 2002. Optionally, the DNAzyme includes a 3'-3' inverted thymidine linkage to thereby improve resistance against nuclease degradation (Santiago et al., *Nat. Med.*, 5: 1264-1269, 1999).

Another AP-1 signaling inhibitor that reduces or prevents expression of c-Jun is a siRNA comprising a nucleotide sequence set forth in SEQ ID NO: 134.

Alternatively, or in addition an inhibitor of AP-1 signaling reduces or inhibits transcriptional activity induced by AP-1 activity. For example, an AP-1 decoy oligonucleotide comprising a sequence set forth in SEQ ID NO: 132 binds to active members of the AP-1 protein complex. As discussed in Desmet et al., *Am. J. Grit. Care Med.*, 172: 671-678, 2005 an oligonucleotide comprising a sequence set forth in SEQ ID NO: 132 is capable of reducing or inhibiting AP-1 signaling.

To facilitate cellular uptake, a nucleic acid inhibitor may be linked or conjugated to a protein transduction domain, e.g., as described herein. Suitable methods for linking or conjugating a nucleic acid to a protein transduction domain will be apparent to the skilled artisan and/or described in, for example, International Application No. PCT/US93/07833.

Alternatively, a nucleic acid inhibitor is identified from a library of nucleic acids using a method known in the art and/or described herein.

2. Peptidyl Inhibitors of AP-1 signaling

In another example of the invention, an AP-1 signaling inhibitor is a peptide or a peptide analog or a peptide derivative. For example, the inhibitor binds to or interacts with JNK and inhibits JNK activity. For example, the peptide prevents or reduces the ability of JNK to phosphorylate a protein, such as, for example c-Jun, c-fos or ATF2. For example, a peptide inhibitor capable of binding to JNK and reducing or preventing JNK activity is a TI-JIP peptide comprising an amino acid sequence set forth in SEQ ID NO: 129 (e.g., as described in Barr et al., *J. Biol. Chem.*, 277: 10987-10997, 2002). An example of an analog of TI-JIP is a retro-inverted analog of TI-JIP, e.g., comprising an amino acid sequence set forth in SEQ ID NO: 130. Examples of additional suitable peptides include a peptide described by Bonny et al., Diabetes, 50: 77-82, 2001, e.g., comprising an amino acid sequence selected from the group consisting of SEQ ID NO: 121, SEQ ID NO: 122, SEQ ID NO: 123 and SEQ ID NO: 124.

In another example, an AP-1 signaling inhibitor is a peptide capable of reducing or inhibiting the activity of a cellular component involved in activating or phosphorylating JNK, or, alternatively, capable of inhibiting a cellular component, e.g., a protein activated and/or phosphorylated by JNK. For example, a peptide inhibitor is capable of inhibiting activity of c-Jun and/or c-Fos and/or ATF2. For example, a peptide inhibitor is capable of inhibiting dimerization of c-Jun (e.g., homodimerization and/or heterodimerization of c-Jun) to thereby inhibit or reduce AP-1 signaling. Likewise a an allosteric peptide inhibitor of JNK or its substrate c-JUN which is capable of inhibiting or reducing AP-1 signalling.

In one example, a suitable peptide comprises an amino acid sequence set forth in any one of SEQ ID NOs: 26-72, 163 or a peptide encoded by a nucleic acid comprising a sequence set forth in any one of SEQ ID NOs: 1-25.

Additional peptide inhibitors of AP-1 signaling are described in Bogoyevitch et al., *Biochimica et Biophysica Acta*, 1697: 89-101, 2004.

Preferred AP-1 signaling inhibitory peptides for use in the treatment or prophylaxis of ARDS are mimetic peptides that do not merely comprise a sequence corresponding to a fragment of a native protein that they inhibit to prevent it binding to its cognate partner or substrate e.g., they are not dominant negative mutants.

Protein Transduction Domains

To facilitate peptide entry into a cell, the peptide may be conjugated to (e.g., expressed as a fusion with) a protein transduction domain. As used herein, the term "protein transduction domain" shall be taken to mean a peptide or protein that is capable of enhancing, increasing or assisting penetration or uptake of a compound conjugated to the protein transduction domain into a cell either in vitro or in vivo. Those skilled in the art will be aware that synthetic or recombinant peptides can be delivered into cells through association with a protein transduction domain such as the TAT sequence from HIV or the Penetratin sequence derived from the Antennapaedia homeodomain protein (see, for example, Temsamani and Vidal, *Drug Discovery Today* 9: 1012-1019, 2004, for review).

A suitable protein transduction domain will be apparent to the skilled artisan and includes, for example, HIV-1 TAT fragment (e.g., comprising an amino acid sequence set forth in any one of SEQ ID NOs: 137-143), signal sequence based peptide 1 (e.g., comprising an amino acid sequence set forth in SEQ ID NO: 153), signal sequence based peptide 2 (e.g., comprising an amino acid sequence set forth in SEQ ID NO: 154), transportan (e.g., comprising an amino acid sequence set forth in SEQ ID NO: 155), amphiphilic model peptide (e.g., comprising an amino acid sequence set forth in SEQ ID NO: 156), polyarginine (e.g., comprising an amino acid sequence set forth in SEQ ID NO: 157) or a Kaposi fibroblast growth factor (FGF) hydrophobic peptide protein transduction domain (e.g., comprising an amino acid sequence set forth in SEQ ID NO: 159 or 160).

Additional suitable protein transduction domains are described, for example, in Zhao and Weisledder *Medicinal Research Reviews*, 24: 1-12, 2004 and Wagstaff and Jans, *Current Medicinal Chemistry*, 13: 1371-1387, 2006.

Linkers

Each of the components of a peptide inhibitor described herein may optionally be separated by a linker that facilitates the independent folding of each of said components, or provides for an appropriate steric spacing between the peptide components. A suitable linker will be apparent to the skilled artisan. For example, it is often unfavorable to have a linker sequence with high propensity to adopt α-helix or β-strand structures, which could limit the flexibility of the protein and consequently its functional activity. Rather, a more desirable linker is a sequence with a preference to adopt extended conformation. In practice, most currently designed linker sequences have a high content of glycine residues that force the linker to adopt loop conformation. Glycine is generally used in designed linkers because the absence of a β-carbon permits the polypeptide backbone to access dihedral angles that are energetically forbidden for other amino acids.

Preferably, the linker is hydrophilic, i.e. the residues in the linker are hydrophilic.

In another example, a linker is a glycine residue. Linkers comprising glycine and/or serine have a high freedom degree for linking of two proteins, i.e., they enable the fused proteins to fold and produce functional proteins. Robinson and Sauer *Proc. Natl. Acad. Sci.* 95: 5929-5934, 1998 found that it is the composition of a linker peptide that is important for stability and folding of a fusion protein rather than a specific sequence.

In one example, linkers join identical peptide target binding moieties to form homodimers. In another example, linkers join different peptide target binding moieties to form heterodimers.

In some forms of the invention, the linker is included in, for example a protein transduction domain.

Peptide Derivatives

The present invention also encompasses a derivative of a peptide inhibitor of AP-1 signaling. As used herein the term "derivative" shall be taken to mean a peptide that is derived from an inhibitory peptide as described herein e.g., a fragment or processed form of the peptide. The term "derivative" also encompasses fusion proteins comprising a peptide of the invention. For example, the fusion protein comprises a label, such as, for example, an epitope, e.g., a FLAG epitope or a V5 epitope or an HA epitope. For example, the epitope is a FLAG epitope. Such a tag is useful for, for example, purifying the fusion protein.

The term "derivative" also encompasses a derivatized peptide, such as, for example, a peptide modified to contain one or more-chemical moieties other than an amino acid. The chemical moiety may be linked covalently to the peptide e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide compound.

Peptide Analogs

In another example of the invention, an AP-1 signaling inhibitor is a peptide analog. As used herein, the term "analog" shall be taken to mean a peptide that is modified to comprise one or more naturally-occurring and/or non-naturally-occurring amino acids, provided that the peptide analog is capable of inhibiting or reducing AP-1 signaling. For example, the term "analog" encompasses an inhibitory peptide comprising one or more conservative amino acid changes. The term "analog" also encompasses a peptide comprising, for example, one or more D-amino acids. Such an analog has the characteristic of, for example, protease resistance.

Suitable peptide analogs include, for example, a peptide comprising one or more conservative amino acid substitutions. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), n-branched side chains (e.g., threonine, valine, isoleucine) and aromatic side chains (e.g., tyrosine, phenylalanine, tryptophan, histidine).

It also is contemplated that other sterically similar compounds may be formulated to mimic the key portions of the peptide structure. Such compounds, which may be termed peptidomimetics, may be used in the same manner as an AP-1 signaling peptide inhibitor. The generation of such an analog may be achieved by the techniques of modeling and chemical design known to those of skill in the art. It will be understood that all such sterically similar peptide analogs fall within the scope of the present invention.

An example of an analog of a peptide of the invention comprises one or more non-naturally occurring amino acids or amino acid analogs. For example, a peptide inhibitor as described herein comprises one or more naturally occurring non-genetically encoded L-amino acids, synthetic L-amino acids or D-enantiomers of an amino acid. For example, the peptide comprises only D-amino acids. For example, the analog comprises one or more residues selected from the group consisting of: hydroxyproline, β-alanine, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylananine 3-benzothienyl alanine 4-chlorophenylalanine, 2-fluorophenylalanine, 3-fluorophenylalanine, 4-fluorophenylalanine, penicillamine, 1,2,3,4-tetrahydro-tic isoquinoline-3-carboxylic acid β-2-thienylalanine, methionine sulfoxide, homoarginine, N-acetyl lysine, 2,4-diamino butyric acid, ρ-aminophenylalanine, N-methylvaline, homocysteine, homoserine, ε-amino hexanoic acid, δ-amino valeric acid, 2,3-diaminobutyric acid and mixtures thereof.

Other amino acid residues that are useful for making the peptides and peptide analogs described herein can be found, e.g., in Fasman, 1989, CRC Practical Handbook of Biochemistry and Molecular Biology, CRC Press, Inc., and the references cited therein.

The present invention additionally encompasses an isostere of a peptide described herein. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[CSNH$_2$], ψ[NHCO], ψ[COCH$_2$], and ψ[(E) or (Z) CH=CH]. In the nomenclature used above, ψ indicates the absence of an amide bond. The structure that replaces the amide group is specified within the brackets.

Other modifications include, for example, an N-alkyl (or aryl) substitution (ψ[CONR]), or backbone crosslinking to construct lactams and other cyclic structures.

Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides.

In another example, a peptide analog is a retro-peptide analog (see, for example, Goodman et al., *Accounts of Chemical Research,* 12:1-7, 1979). A retro-peptide analog comprises a reversed amino acid sequence of a peptide inhibitor described herein. For example, a retro-peptide analog of a peptide inhibitor comprises a reversed amino acid sequence of a sequence set forth in any one of SEQ ID NOs: 26-72, 121-124, 129, 131 or 163. For example, a retro-peptide analog of a peptide inhibitor comprises a reversed amino acid sequence of a sequence set forth in any one of SEQ ID NOs: 26-72 or 163. Optionally, the peptide analog comprises an additional feature, such as, for example, a protein transduction domain, which may also be a retro-peptide.

In a further example, an analog of a peptide described herein is a retro-inverso peptide (as described, for example, in Sela and Zisman, *FASEB J.* 11:449, 1997). Evolution has ensured the almost exclusive occurrence of L-amino acids in naturally occurring proteins. As a consequence, virtually all proteases cleave peptide bonds between adjacent L-amino acids. Accordingly, artificial proteins or peptides composed of D-amino acids are preferably resistant to proteolytic breakdown. Retro-inverso peptide analogs are isomers of linear peptides in which the direction of the amino acid sequence is reversed (retro) and the chirality, D- or L-, of one or more amino acids therein is inverted (inverso) e.g., using D-amino acids rather than L-amino acids, e.g., Jameson et al., *Nature,* 368, 744-746 (1994); Brady et al., *Nature,* 368, 692-693 (1994). The net result of combining D-enantiomers and reverse synthesis is that the positions of carbonyl and amino groups in each amide bond are exchanged, while the position of the side-chain groups at each alpha carbon is preserved. An advantage of retro-inverso peptides is their enhanced activity in vivo due to improved resistance to proteolytic degradation, i.e., the peptide has enhanced stability. (e.g., Chorev et al., *Trends Biotech.* 13, 438-445, 1995).

Retro-inverso peptide analogs may be complete or partial. Complete retro-inverso peptides are those in which a complete sequence of a peptide descried herein is reversed and the chirality of each amino acid in a sequence is inverted, other than glycine, because glycine does not have a chiral analog. Partial retro-inverso peptide analogs are those in which only some of the peptide bonds are reversed and the chirality of only those amino acid residues in the reversed portion is inverted. For example, one or two or three or four or five or six or seven or eight or nine or ten or eleven or twelve or thirteen or fourteen or fifteen or sixteen or seventeen or eighteen or nineteen or twenty or twenty one or twenty two or twenty three or twenty four or twenty five or twenty six or twenty seven or twenty eight or twenty nine or thirty or thirty one or thirty two or thirty three or thirty four or thirty five or thirty six or thirty seven or thirty eight amino acid residues are D-amino acids. The present invention clearly encompasses both partial and complete retro-inverso peptide analogs. For example, the present invention provides a retro-inverso peptide analog comprising an amino acid sequence set forth in any one of SEQ ID NOs: 73-120, 125-128, 130, 164 or 165. For example, a retro-inverso peptide analog comprises an amino acid sequence set forth in any one of SEQ ID NOs: 73-120, 164 or 165. In this respect, such a retroinverso peptide analog may optionally include an additional component, such as, for example, a protein transduction domain, which may also be retroinverted. For example, a retro-inverso peptide analog comprises an amino acid sequence set forth in any one of SEQ ID NOs: 74, 76, 78, 81, 83, 84, 86, 88, 90, 92, 94, 96, 98, 100, 101, 104, 106, 108, 110, 112, 114, 116, 118, 120 or 165.

As will be apparent to the skilled artisan based on the foregoing description, the present invention provides peptide AP-1 signaling inhibitors e.g., selected individually or collectively from the group consisting of:
(i) a peptide comprising an amino acid sequence set forth in any on of SEQ ID NOs: 26-72, 121-124, 129, 131 or 163;
(ii) a peptide encoded by a nucleic acid comprising a sequence set forth in any one of SEQ ID NOs: 1-25;
(iii) the peptide of (i) or (ii) additionally comprising a protein transduction domain, e.g., a HIV tat basic region (e.g., comprising a sequence set forth in any one of SEQ ID NOs: 137-143) or a retroinverted analog thereof (e.g., comprising a sequence set forth in any one of SEQ ID NOs: 144-152);
(iii) an analog of any one of (i) to (iii) selected from the group consisting of (a) the sequence of any one of (i) to (iii) comprising one or more non-naturally-occurring amino acids; (b) the sequence of any one of (i) to (iii) comprising one or more non-naturally-occurring amino acid analogs; (c) an isostere of any one of (i) to (iii); (d) a retro-peptide analog of any one of (i) to (iii); and (e) a retro-inverted peptide analog of any one of (i) to (iii).
(iv) a retroinverted peptide analog comprising an amino acid sequence set forth in any one of SEQ ID NOs: 73-120, 125-128, 130, 164 or 165.

In one example, an analog peptide inhibitor of AP-1 signaling comprises an amino acid sequence set forth in SEQ ID NO: 103 or SEQ ID NO: 104 or SEQ ID NO: 105 or SEQ ID NO: 106 or SEQ ID NO: 107 or SEQ ID NO: 108.

The present invention also provides a composition comprising an AP-1 signaling peptide inhibitor or an analog thereof e.g., a peptidyl AP-1 signaling inhibitor or an analog thereof selected individually or collectively from the group consisting of:
(i) a functional fragment of a peptide comprising an amino acid sequence set forth in any on of SEQ ID NOs: 26-72, 121-124, 129, 131 or 163;
(ii) a functional fragment of a peptide encoded by a nucleic acid comprising a sequence set forth in any one of SEQ ID NOs: 1-25;
(iii) the peptide of (i) or (ii) additionally comprising a protein transduction domain, e.g., a HIV tat basic region (e.g., comprising a sequence set forth in any one of SEQ ID NOs: 137-143) or a retroinverted analog thereof (e.g., comprising a sequence set forth in any one of SEQ ID NOs: 144-152);
(iii) an analog of any one of (i) to (iii) selected from the group consisting of (a) the sequence of any one of (i) to (iii) comprising one or more non-naturally-occurring amino acids; (b) the sequence of any one of (i) to (iii) comprising one or more non-naturally-occurring amino acid analogs; (c) an isostere of any one of (i) to (iii); (d) a retro-peptide analog of any one of (i) to (iii); and (e) a retro-inverted peptide analog of any one of (i) to (iii).
(iv) a functional fragment of a retroinverted peptide analog comprising an amino acid sequence set forth in any one of SEQ ID NOs: 73-120, 125-128, 130, 164 or 165.

As used herein the term "functional fragment" shall be taken to mean a fragment of a peptide or analog thereof that is capable of reducing or preventing neutrophilic inflammation and/or to induce and/or enhance proliferation of a cell. In this respect, the activity of a functional fragment need not be the same as that of the peptide or analog from which the fragment is derived. For example, the fragment may have enhanced or reduced activity compared to the peptide or analog from which it is derived.

Peptide Synthesis

A peptide or an analog or derivative thereof is preferably synthesized using a chemical method known to the skilled artisan. For example, synthetic peptides are prepared using known techniques of solid phase, liquid phase, or peptide condensation, or any combination thereof, and can include natural and/or unnatural amino acids. Amino acids used for peptide synthesis may be standard Boc (Na-amino protected Na-t-butyloxycarbonyl) amino acid resin with the deprotecting, neutralization, coupling and wash protocols of the original solid phase procedure of Merrifield, J. Am. Chem. Soc., 85:2149-2154, 1963, or the base-labile Na-amino protected 9-fluorenylmethoxycarbonyl (Fmoc) amino acids described by Carpino and Han, J. Org. Chem., 37:3403-3409, 1972. Both Fmoc and Boc Na-amino protected amino acids can be obtained from various commercial sources, such as, for example, Fluka, Bachem, Advanced Chemtech, Sigma, Cambridge Research Biochemical, Bachem, or Peninsula Labs.

Generally, chemical synthesis methods comprise the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis. Synthesis. Biology, Von, for classical solution synthesis. These methods are suitable for synthesis of a peptide of the present invention or an analog or derivative thereof.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

A peptide, analog or derivative as described herein can also be chemically prepared by other methods such as by the method of simultaneous multiple peptide synthesis. See, e.g., Houghten *Proc. Natl. Acad. Sci. USA* 82: 5131-5135, 1985 or U.S. Pat. No. 4,631,211.

As will be apparent to the skilled artisan based on the description herein, an analog or derivative of a peptide of the invention may comprise D-amino acids, a combination of D- and L-amino acids, and various unnatural amino acids (e.g., α-methyl amino acids, Cα-methyl amino acids, and Nα-methyl amino acids, etc) to convey special properties. Synthetic amino acids include ornithine for lysine, fluorophenylalanine for phenylalanine, and norleucine for leucine or isoleucine. Methods for the synthesis of such peptides will be apparent to the skilled artisan based on the foregoing description.

Recombinant Peptide Production

Alternatively, or in addition, a peptide or analog or derivative thereof or fusion protein comprising same is produced as a recombinant protein. To facilitate the production of a recombinant peptide or fusion protein nucleic acid encoding same is preferably isolated or synthesized. Typically the nucleic acid encoding the recombinant protein is/are isolated using a known method, such as, for example, amplification (e.g., using PCR or splice overlap extension) or isolated from nucleic acid from an organism using one or more restriction enzymes or isolated from a library of nucleic acids. Methods for such isolation will be apparent to the ordinary skilled artisan and/or described in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001).

For expressing protein by recombinant means, a protein-encoding nucleic acid is placed in operable connection with a promoter or other regulatory sequence capable of regulating expression in a cell-free system or cellular system. For example, nucleic acid comprising a sequence that encodes a peptide is placed in operable connection with a suitable promoter and maintained in a suitable cell for a time and under conditions sufficient for expression to occur. Nucleic acid encoding a peptide inhibitor of AP-1 signaling is described herein or is derived from the publicly available amino acid sequence.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid (e.g., a transgene), e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid (e.g., a transgene and/or a selectable marker gene and/or a detectable marker gene) to which it is operably linked. Preferred promoters can contain additional copies of one or more specific regulatory elements to further enhance expression and/or alter the spatial expression and/or temporal expression of said nucleic acid.

As used herein, the term "in operable connection with", "in connection with" or "operably linked to" means positioning a promoter relative to a nucleic acid (e.g., a transgene) such that expression of the nucleic acid is controlled by the promoter. For example, a promoter is generally positioned 5' (upstream) to the nucleic acid, the expression of which it controls. To construct heterologous promoter/nucleic acid combinations (e.g., promoter/nucleic acid encoding a peptide), it is generally preferred to position the promoter at a distance from the gene transcription start site that is approximately the same as the distance between that promoter and the nucleic acid it controls in its natural setting, i.e., the gene from which the promoter is derived. As is known in the art, some variation in this distance can be accommodated without loss of promoter function.

Should it be preferred that a peptide or fusion protein of the invention is expressed in vitro a suitable promoter includes, but is not limited to a T3 or a T7 bacteriophage promoter (Hanes and Plückthun *Proc. Natl. Acad. Sci. USA*, 94 4937-4942 1997).

Typical expression vectors for in vitro expression or cell-free expression have been described and include, but are not limited to the TNT T7 and TNT T3 systems (Promega), the pEXP1-DEST and pEXP2-DEST vectors (Invitrogen).

Typical promoters suitable for expression in bacterial cells include, but are not limited to, the lacz promoter, the Ipp promoter, temperature-sensitive λL or λR promoters, T7 promoter, T3 promoter, SP6 promoter or semi-artificial promoters such as the IPTG-inducible tac promoter or lacUV5 promoter. A number of other gene construct systems for expressing the nucleic acid fragment of the invention in bacterial cells are well-known in the art and are described for example, in Ausubel et al (In: Current Protocols in Molecular Biology. Wiley Interscience, ISBN 047 150338, 1987), U.S. Pat. No. 5,763,239 (Diversa Corporation) and Sambrook et al (In: Molecular Cloning: Molecular Cloning: A Laboratory Manual, Cold Spring Harbor Laboratories, New York, Third Edition 2001).

Numerous expression vectors for expression of recombinant polypeptides in bacterial cells and efficient ribosome binding sites have been described, and include, for example, PKC30 (Shimatake and Rosenberg, *Nature* 292, 128, 1981); pKK173-3 (Amann and Brosius, *Gene* 40, 183, 1985), pET-3 (Studier and Moffat, *J. Mol. Biol.* 189, 113, 1986); the pCR vector suite (Invitrogen), pGEM-T Easy vectors (Promega), the pL expression vector suite (Invitrogen) the pBAD/TOPO or pBAD/thio—TOPO series of vectors containing an arabinose-inducible promoter (Invitrogen, Carlsbad, Calif.), the latter of which is designed to also produce fusion proteins with a Trx loop for conformational constraint of the expressed protein; the pFLEX series of expression vectors (Pfizer Inc., CT, USA); the pQE series of expression vectors (QIAGEN, CA, USA), or the pL series of expression vectors (Invitrogen), amongst others.

Typical promoters suitable for expression in viruses of eukaryotic cells and eukaryotic cells include the SV40 late promoter, SV40 early promoter and cytomegalovirus (CMV) promoter, CMV IE (cytomegalovirus immediate early) promoter amongst others. Preferred vectors for expression in mammalian cells (e.g., 293, COS, CHO, 10T cells, 293T cells) include, but are not limited to, the pcDNA vector suite supplied by Invitrogen, in particular pcDNA 3.1 myc-His-tag comprising the CMV promoter and encoding a C-terminal 6×His and MYC tag; and the retrovirus vector pSRαtkneo (Muller et al., *Mol. Cell. Biol.*, 11, 1785, 1991).

A wide range of additional host/vector systems suitable for expressing a peptide or fusion protein of the present invention are available publicly, and described, for example, in Sambrook et al (In: Molecular cloning, A laboratory manual, second edition, Cold Spring Harbor Laboratory, Cold Spring Harbor, N.Y., 1989).

Means for introducing the isolated nucleic acid molecule or a gene construct comprising same into a cell for expression are well-known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

3. Antibody Inhibitors

The present invention also includes an antibody-based AP-1 signaling inhibitor and/or uses thereof for the treatment and/or prophylaxis of ARDS and complications thereof. For example, an antibody or antibody-based inhibitor of AP-signaling is used in the preparation of a medicament for the treatment or prophylaxis of ARDS and/or complications thereof. Estus et al., *J. Cell. Biol.*, 127: 1717-1727, 1994, for example, describe antibodies against c-Jun or Fos that are capable of inhibiting AP-1 signaling.

Methods for producing additional antibodies will be apparent to the skilled artisan. For example, a monoclonal antibody against a protein involved in or necessary for AP-1 signaling (e.g., MAPKKK, MAPKK, JNK or c-Jun, or c-Fos or Cdc42 or Pak1 or Rac1) is produced by immunizing an animal, e.g., a mouse, with said protein or an immunogenic fragment thereof. Optionally, the protein or fragment is injected in the presence of an adjuvant, such as, for example Freund's complete or incomplete adjuvant, lysolecithin and/or dinitrophenol to enhance the immune response to the immunogen. Spleen cells are then obtained from the immunized animal. The spleen cells are then immortalized by, for example, fusion with a myeloma cell fusion partner, preferably one that is syngenic with the immunized animal. A variety of fusion techniques may be employed, for example, the spleen cells and myeloma cells may be combined with a nonionic detergent or electrofused and then grown in a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and growth media in which the cells have been grown is tested for the presence of binding activity against the polypeptide (immunogen). Hybridomas having high reactivity and specificity are preferred.

Monoclonal antibodies are isolated from the supernatants of growing hybridoma colonies using methods such as, for example, affinity purification using the immunogen to isolate an antibody capable of binding thereto. In addition, various techniques may be employed to enhance the yield, such as injection of the hybridoma cell line into the peritoneal cavity of a suitable vertebrate host, such as a mouse. Monoclonal antibodies are then harvested from the ascites fluid or the blood of such an animal subject. Contaminants are removed from the antibodies by conventional techniques, such as chromatography, gel filtration, precipitation, and/or extraction.

To ensure that the antibody is capable of entering a cell and inhibiting or reducing AP-1 signaling an antibody fragment or recombinant antibody may be produced and conjugated to a protein transduction domain, for example, a protein transduction domain described herein.

4. Small Molecule Inhibitors

In a still further example of the invention, an AP-1 signaling inhibitor is a small molecule. For example, CEP-1347 (or 3,9 bis[(ethylthio)methyl]-K252a) is capable of inhibiting AP-1 signaling (Kaneko et al., *J. Med. Chem.*, 40: 1863-1869, 1997). The present invention thus includes a small molecule AP-1 signaling inhibitor and/or uses thereof for the treatment and/or prophylaxis of ARDS and complications thereof. For example, a small molecule inhibitor of AP-signaling is used in the preparation of a medicament for the treatment or prophylaxis of ARDS and/or complications thereof.

Alternatively, the compound SP600125 is an anthrapyrazolone ATP-competitive inhibitor (anthra[1,9-cd]pyrazole-6-(2H)-one) capable directly interacting with JNK and inhibiting AP-1 signaling (Bennet et al., *Proc. Natl. Acad. Sci. USA*, 98: 13681-13686, 2001.

Alternatively, a natural product such as, for example, curcumin, dihydroguaiaretic acid or an anthraquinone derivative are capable of inhibiting AP-1 signaling by inhibiting the binding of AP-1 to an AP-1 binding site (Hahm et al., *Cancer Lett.*, 184: 89-96, 2002; Park et al., *Cancer Lett*, 127: 23-28, 2998; and Goto et al., *J. Antibiot.*, 51: 539-544, 1998).

Tsuchida et al., *J. Medicinal Chem.*, 49:80-91, 2006, describes a number of small molecule inhibitors of AP-1 signaling based on the structure of a peptide inhibitor. These compounds include (R)-4-(4-methylpentanoyl)-8-(4-methylpentylidene)-1-thia-4-azaspiro[4.5]decane-3-carboxylic acid; (R)-8-(3-methylbutylidene)-4-(5-methylhexanoyl)-1-thia-4-azaspiro[4.5]decane-3-carboxylic acid; and 3-[2-isobutoxy-5-(4-isobutoxybenzoyl)phenyl)propionic acid. Tsuchida et al., additionally describes methods for identifying additional AP-1 signaling inhibitors.

Alternatively, a suitable small molecule inhibitor is identified from a library of small molecules. Techniques for synthesizing small organic compounds will vary considerably depending upon the compound, however such methods will be well known to those skilled in the art. In one embodiment, informatics is used to select suitable chemical building blocks from known compounds, for producing a combinatorial library. For example, QSAR (Quantitative Structure Activity Relationship) modeling approach uses linear regressions or regression trees of compound structures to determine suitability. The software of the Chemical Computing Group, Inc. (Montreal, Canada) uses high-throughput screening experimental data on active as well as inactive compounds, to create a probabilistic QSAR model, which is subsequently used to select lead compounds. The Binary QSAR method is based upon three characteristic properties of compounds that form a "descriptor" of the likelihood that a particular compound will or will not perform a required function: partial charge, molar refractivity (bonding interactions), and logP (lipophilicity of molecule). Each atom has a surface area in the molecule and it has these three properties associated with it. All atoms of a compound having a partial charge in a certain range are determined and the surface areas (Van der Walls Surface Area descriptor) are summed. The binary QSAR models are then used to make activity models or ADMET models, which are used to build a combinatorial library. Accordingly, lead compounds identified in initial screens, can be used to expand the list of compounds being screened to thereby identify highly active compounds.

Assays to Identify and Isolate Therapeutic and Prophylactic Compounds

In an additional or alternative embodiment of the invention, a compound library or mixture is screened by one or more of the following assays to isolate there from a compound that reduces neutrophilic inflammation and/or enhances re-epithelialization and, as a consequence, is suitable for the treatment of ARDS and complications thereof, and for the prophylactic treatment of clinical disorders associated with the development of ARDS. This may require repeated screening to eventually purify the compound free or substantially free of contaminants.

Alternatively, a previously-isolated compound not known to have the ability to reduces neutrophilic inflammation and/or to enhance re-epithelialization is screened by one or more of the foregoing assays to determine whether or not it has this property and is therefore suitable for the treatment of ARDS and complications thereof, and for the prophylactic treatment of clinical disorders associated with the development of ARDS.

It is to be understood that the following assays can be utilized in separately or collectively and in any order determined empirically to identify or isolate the desired product at a level of purity and having an activity ascribed to it suitable for the treatment of ARDS and its complications. The activity and purity of the compounds determined by these assays make the compound suitable of formulations e.g., injectable and/or inhalable medicaments for treatment and/or prophylaxis.

The present invention encompasses the use of any in silico or in vitro analytical method and/or industrial process for carrying the screening methods described herein into a pilot scale production or industrial scale production of a compound identified in such screens. This invention also provides information for such production method(s). Accordingly, the present invention also provides a process for identifying or determining a compound supra, said method comprising:
(i) performing a method as described herein according to any embodiment to thereby identify a compound;
(ii) optionally, determining the amount of the compound;
(iii) optionally, determining the structure of the compound; and
(iv) providing the compound or the name or structure of the compound such as, for example, in a paper form, machine-readable form, or computer-readable form.

As used herein, the term "providing the compound" shall be taken to include any chemical or recombinant synthetic means for producing said compound (with or without derivitization) or alternatively, the provision of a compound that has been previously synthesized by any person or means.

In one example, the compound or the name or structure of the compound is provided with an indication as to its use e.g., as determined by a screen described herein.

The present invention additionally provides a process for producing a compound supra, said method comprising:
a process for identifying or determining a compound or modulator supra, said method comprising:
(i) performing a method as described herein according to any embodiment to thereby identify or determine a compound;
(ii) optionally, determining the amount of the compound;
(iii) optionally, determining the structure of the compound;
(iv) optionally, providing the name or structure of the compound such as, for example, in a paper form, machine-readable form, or computer-readable form; and
(v) providing the compound.

In the case of a peptide, the method optionally further comprises providing a chemical derivative of the peptide by protection of the amino- or carboxy-terminus, cyclization of the peptide or construction of the peptide as a retroinverso peptide. The method also optionally involves identifying and/or validating one or more peptidyl compounds such as by displaying a peptide in vitro or on a bacteriophage particle, e.g., using lytic T7-based or non-lytic M13-based phage display, identifying the sequence of the peptide, making the compound by recombinant means or peptide chemistry, and testing the ability of the peptide to produce a desired effect such as reduced or prevented neutrophilic inflammation or inhibition of a specific protein interaction involved in a neutrophilic inflammatory response. Preferably, the peptide is displayed within a protein-based scaffold e.g., a scaffold structure derived from lipocalin, ankyrin repeats, fibronectin, kunitz domains, A-domains, affibodies etc. Alternatively the inhibitory peptide can be grafted into such a protein based scaffold in order to enhance stability or improve stability.

In one example, the compound or the name or structure of the compound is provided with an indication as to its use e.g., as determined by a screen described herein.

The present invention also provides a method of manufacturing a compound identified by a screening method described herein according to any embodiment for use in medicine comprising:
(i) performing a method as described herein according to any embodiment to thereby identify or determine a compound; and
(ii) using the compound in the manufacture of a therapeutic for use in medicine.

In one example, the method comprises the additional step of isolating the compound. Alternatively, a compound is identified and is produced for use in the manufacture of a compound for use in medicine.

1. Assays Based Upon AP-1 Signaling Inhibitory Activity

In addition to providing a variety of AP-1 signaling inhibitors, the present invention contemplates identification of new inhibitory compounds. Suitable compounds for testing will be apparent to the skilled artisan based on the foregoing description.

The ability of a compound to inhibit AP-1 signaling is then determined by any of a variety of assays.

For example, Tsuchida et al., supra, describe an enzyme linked immunoassay (ELISA) that uses a double stranded oligonucleotide comprising an AP-1 binding site and an AP-1 bZIP peptide, The AP-1 bZIP peptide is coated onto a microtitre plate and blocked. Labeled oligonucleotide (e.g., digoxigenin labeled oligonucleotide) is added to the microtitre plate in the presence or absence of a test compound. Following washing to remove unbound oligonucleotide, the amount of label bound to the AP-1 peptide is determined. A compound that reduces the level of oligonucleotide bound to the peptide is considered to inhibit AP-1 signaling by virtue of inhibiting AP-1 transcriptional regulation.

An additional assay to determine an AP-1 signaling inhibitor comprises producing or obtaining a cell comprising a reporter gene operably connected to a promoter comprising an AP-1 binding site. The cell is then contacted with a test compound for a time and under conditions sufficient to inhibit or reduce AP-1 signaling and the level of reporter gene expression determined. A compound that reduces reporter gene expression is considered to inhibit or reduce AP-1 signaling.

Alternatively, a reverse hybrid assay is performed to identify an AP-1 signaling inhibitor. For example, a reverse two-hybrid assay is performed to identify a compound that inhibits interaction of two proteins, the interaction of which is required for AP-1 signaling. For example, a compound is identified that inhibits or reduces the interaction between JNK and c-Jun, a MAP kinase kinase kinase and JNK, JNK and JIP, or any of the proteins that interact to form AP-1. For example, an assay is performed to identify a compound that inhibits c-Jun dimerization. Reverse hybrid methods will be apparent to the skilled artisan and/or described in Watt et al. (USSN 09/227,652) or Erickson et al. (WO95/26400).

2. Assays Based Upon Ability to Inhibit Apoptosis and/or Necrosis

In one example of the invention, an AP-1 signaling inhibitor is also capable of inhibiting apoptosis and/or necrosis. In such assays, cell death can be artificially-induced by exposure to UV or gamma irradiation, exposure to TRAIL or exposure to apoptotic DNA damaging agents such as the drugs Etoposide or Cisplatin. Potential AP-1 signalling inhibitors are applied either before during or after the exposure to the cytotoxic condition or radiation, in order to see if they have a protective function in reducing the amount of cell death.

Methods for determining a compound that inhibits apoptosis will be apparent to the skilled artisan. For example, APOPTEST (available from Immunotech) stains cells early in apoptosis, and does not require fixation of the cell sample (Martin et al., 1994). This method utilizes an annexin V antibody to detect cell membrane re-configuration that is characteristic of cells undergoing apoptosis. Apoptotic cells stained in this manner can then sorted either by fluorescence activated cell sorting (FACS), ELISA or by adhesion and panning using immobilized armexin V antibodies.

Alternatively, a terminal deoxynucleotidyl transferase-mediated biotinylated UTP nick end-labeling (TUNEL) assay is used to determine the level of cell death. The TUNEL assay uses the enzyme terminal deoxynucleotidyl transferase to label 3'-OH DNA ends, generated during apoptosis, with biotinylated nucleotides. The biotinylated nucleotides are then detected by using streptavidin conjugated to a detectable marker. Kits for TUNEL staining are available from, for example, Intergen Company, Purchase, N.Y.

Alternatively, or in addition, an activated caspase, such as, for example, Caspase 3 is detected. Several caspases are effectors of apoptosis and, as a consequence, are only activated to significant levels in a cell undergoing programmed cell death. Kits for detection of an activated caspase are available from, for example, Promega Corporation, Madison Wis., USA. Such assays are useful for both immunocytochemical or flow cytometric analysis of cell death.

Methods for detecting necrosis or determining the level of necrosis, e.g., in a sample comprising cells are known in the art and/or described, for example, in Lemaire et al., *Cell Death and Differentiation*, 6: 813-820, 1999. The invention also encompasses the use of fluorescent activated cell sorting (FACS) to sort living or dying cells in a population of cells.

3. Assays Based Upon Cellular Proliferative Activity

In a further example of the invention, an AP-1 signaling inhibitor is also capable of inducing and/or enhancing proliferation of epithelial cells, especially alveolar epithelial cells. Methods for determining a compound that induces or enhances proliferation will be apparent to the skilled artisan. For example, incorporation of $^3$H-thymidine or $^{14}$C-thymidine into DNA as it is synthesized is an assay for DNA synthesis associated with cell division. In such an assay, a cell is incubated in the presence of labeled thymidine for a time and under condition sufficient for cell division to occur. Following washing to remove any unincorporated thymidine, the amount of label (e.g. the radioactive label) in the sample is detected, e.g., using a scintillation counter. The amount of label detected is indicative of the level of proliferation of one or more cells in the sample. Assays for the detection of thymidine incorporation into a live cell are available from, for example, Amersham Pharmacia Biotech.

In another embodiment, cellular proliferation is measured using a 3-(4,5-dimethylthiazolyl-2)-2,5-diphenyltetrazolium bromide (MTT) assay. In such an assay, MTT is contacted to live cells for a time and under conditions sufficient for cellular proliferation to occur. The yellow tetrazolium MTT is reduced by metabolically active cells, in part by the action of dehydrogenase enzymes, to generate reducing equivalents such as NADH and NADPH. The resulting intracellular purple formazan is then solubilized and quantified by spectrophotometric means. Assay kits for MTT assays are available from, for example, American Type Culture Collection.

Alternative assays for determining cellular proliferation, include, for example, measurement of DNA synthesis by BrdU incorporation (by ELISA or immunohistochemistry, kits available from Amersham Pharmacia Biotech), expression of proliferating cell nuclear antigen (PCNA) (by ELISA, FACS or immunohistochemistry, kits available from Oncogene Research Products) or a Hoechst cell proliferation assay that detects DNA synthesis (available from Trevigen Inc.).

Alternatively, the growth rate of the cell is determined, for example, manually, by, for example observing or measuring the size of a colony of cells over a period of time or, alternatively or in addition counting the number of cells over a period of time.

Formulations

A compound of the invention as described herein according to any embodiment is formulated for therapy or prophylaxis with a carrier or excipient e.g., suitable for inhalation or injection.

The term "carrier or excipient" as used herein, refers to a carrier or excipient that is conventionally used in the art to facilitate the storage, administration, and/or the biological activity of an active compound. A carrier may also reduce any undesirable side effects of the active compound. A suitable carrier is, for example, stable, e.g., incapable of reacting with other ingredients in the formulation. In one example, the carrier does not produce significant local or systemic adverse effect in recipients at the dosages and concentrations employed for treatment. Such carriers and excipients are generally known in the art. Suitable carriers for this invention include those conventionally used, e.g., water, saline, aqueous dextrose, dimethyl sulfoxide (DMSO), and glycols are preferred liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

The skilled artisan will be aware of a suitable carrier or excipient. For example, a carrier or excipient does not inhibit the anti-inflammatory activity and/or mitogenic activity of an AP-1 signaling inhibitor. In one example, the carrier or excipient permits the inhibitor to inhibit or reduce neutrophilic inflammation in the lung and/or to induce alveolar re-epithelialization.

The formulations can be subjected to conventional pharmaceutical expedients, such as sterilization, and can contain a conventional pharmaceutical additive, such as a preservative and/or a stabilizing agent and/or a wetting agent and/or an emulsifying agent and/or a salt for adjusting osmotic pressure and/or a buffer and/or other additives known in the art. Other acceptable components in the composition of the invention include, but are not limited to, isotonicity-modifying agents such as water and/or saline and/or a buffer including phosphate, citrate, succinate, acetic acid, or other organic acids or their salts.

In an example, a formulation includes one or more stabilizers, reducing agents, anti-oxidants and/or anti-oxidant chelating agents. The use of buffers, stabilizers, reducing agents, anti-oxidants and chelating agents in the preparation of compositions, is known in the art and described, for example, in Wang et al. *J. Parent. Drug Assn.* 34:452-462, 1980; Wang et al. *J. Parent. Sci. Tech.* 42:S4-S26 (Supplement), 1988. Suitable buffers include acetate, adipate, benzoate, citrate, lactate, maleate, phosphate, tartarate, borate, tri(hydroxymethyl aminomethane), succinate, glycine, histidine, the salts of various amino acids, or the like, or combinations thereof. Suitable salts and isotonicifiers include sodium chloride, dextrose, mannitol, sucrose, trehalose, or the like. Where the carrier is a liquid, it is preferred that the carrier is hypotonic or isotonic with oral, conjunctival, or dermal fluids and has a pH within the range of 4.5-8.5. Where the carrier is in powdered form, it is preferred that the carrier is also within an acceptable non-toxic pH range.

In another example, a formulation as described herein according to any embodiment additionally comprises a compound that enhances or facilitates uptake of a compound. Suitable dermal permeation enhancers are, for example, a lipid disrupting agent (LDA), a solubility enhancer, or a surfactant.

LDAs are typically fatty acid-like molecules proposed to fluidize lipids in the human skin membrane. Suitable LDAs are described, for example, in Francoeur et al., *Pharm. Res.*, 7: 621-627, 1990 and U.S. Pat. No. 5,503,843. For example, a suitable LDA is a long hydrocarbon chain with a cis-unsaturated carbon-carbon double bond. These molecules have been shown to increase the fluidity of the lipids, thereby increasing drug transport. For example, oleic acid, oleyl alcohol, decanoic acid, and butene diol are useful LDAs.

Solubility enhancers act by increasing the maximum concentration of drug in a composition, thus creating a larger concentration gradient for diffusion. For example, a lipophilic vehicle isopropyl myristate (IPM) or an organic solvent ethanol or N-methyl pyrrolidone (NMP) or dimethyl sulfoxide (DMSO) are suitable solubility enhancers (Liu et al., *Pharm. Res.* 8: 938-944, 1991; and Yoneto et al., *J. Pharm. Sci.* 84: 853-860, 1995).

Surfactants are amphiphilic molecules capable of interacting with the polar and lipid groups in the skin. These molecules have affinity to both hydrophilic and hydrophobic groups, which facilitate in traversing complex regions of the dermis. Suitable surfactants include, for example, an anionic surfactant lauryl sulfate (SDS) or a nonionic surfactant polysorbate 80 (Tween 80). Suitable surfactants are described, for example, in Sarpotdar et al., *J. Pharm. Sci.* 75: 176-181, 1986)

In another example, the formulation is a microemulsion. Microemulsion systems are useful for enhancing transdermal delivery of a compound. Characteristics of such microemulsion systems are sub-micron droplet size, thermodynamic stability, optical transparency, and solubility of both hydrophilic and hydrophobic components. Microemulsion systems have been shown to be useful for transdermal delivery of compounds and to exhibit improved solubility of hydrophobic drugs as well as sustained release profiles (Lawrence, et. al. *Int. Journal of Pharmaceutics* 111: 63-72, 1998).

In another example, a formulation comprises a peptidyl moiety conjugated to a hydrolysable polyethylene glycol (PEG) essentially as described by Tsubery et al., *J. Biol. Chem.* 279 (37) pp. 38118-38124. Without being bound by any theory or mode of action, such formulations provide for extended or longer half-life of the peptide moiety in circulation.

In another example, a formulation comprises a nanoparticle comprising the peptide moiety or other active ingredient bound to it or encapsulated within it. Without being bound by any theory or mode of action, delivery of a peptidyl composition from a ananoparticle may reduce renal clearance of the peptide(s).

In another example, a formulation comprises a liposome carrier or excipient to facilitate uptake of an inhibitor into a cell. Liposomes are considered to interact with a cell by stable absorption, endocytosis, lipid transfer, and/or fusion (Egerdie et al., *J. Urol.* 142:390, 1989). For example, liposomes comprise molecular films, which fuse with cells and provide optimal conditions for wound healing (K. Reimer et al., *Dermatology* 195(suppl. 2):93, 1999). Generally, liposomes have low antigenicity and can be used to encapsulate and deliver components that cause undesirable immune responses in patients (Natsume et al., *Jpn. J. Cancer Res.* 91:363-367, 2000)

For example, anionic or neutral liposomes often possess excellent colloidal stability, since substantially no aggregation occurs between the carrier and the environment. Consequently their biodistribution is excellent, and their potential for irritation and cytotoxicity is low.

Alternatively, cationic liposomal systems, e.g. as described in Mauer et al., *Molecular Membrane Biology*, 16: 129-140, 1999 or Maeidan et al., *BBA* 1464: 251-261, 2000 are useful for delivering compounds into a cell. Such cationic systems provide high loading efficiencies. Moreover, PEGylated cationic liposomes show enhanced circulation times in vivo (Semple *BBA* 1510, 152-166, 2001).

Amphoteric liposomes are a recently described class of liposomes having an anionic or neutral charge at pH 7.4 and a cationic charge at pH 4. Examples of these liposomes are described, for example, in WO 02/066490, WO 02/066012 and WO 03/070735. Amphoteric liposomes have been found to have a good biodistribution and to be well tolerated in animals and they can encapsulate nucleic acid molecules with high efficiency.

U.S. Ser. No. 09/738,046 and U.S. Ser. No. 10/218,797 describe liposomes suitable for the delivery of peptides or proteins into a cell.

Injectable Formulations

Injectable formulations comprising peptide(s) of the invention or other active ingredient and a suitable carrier or excipient preferably have improved stability and/or rapid onset of action, and are for intravenous, subcutaneous, intradermal or intramuscular injection.

For parenteral administration, the peptidyl component or other active ingredient, may be administered as injectable doses of a solution or suspension in a physiologically acceptable diluent with a pharmaceutical carrier which can be a sterile liquid such as water or oil e.g., petroleum, animal, vegetable or synthetic oil including any one or more of peanut oil, soybean oil, mineral oil, etc. Surfactant and other pharmaceutically acceptable adjuvants or excipients may be included. In general, water, saline, aqueous dextrose or other related sugar solution, ethanol or glycol e.g., polyethylene glycol or propylene glycol, is a preferred carrier.

The injectable formulations may also contain a chelator e.g., EDTA, and/or a dissolution agent e.g., citric acid. Such components may assist rapid absorption of the active ingredient into the blood stream when administered by injection.

One or more solubilizing agents may be included in the formulation to promote dissolution in aqueous media. Suitable solubilizing agents include e.g., wetting agents such as polysorbates, glycerin, a poloxamer, non-ionic surfactant, ionic surfactant, food acid, food base e.g., sodium bicarbonate, or an alcohol. Buffer salts may also be included for pH control.

Stabilizers are used to inhibit or retard drug decomposition reactions in storage or in vivo which include, by way of example, oxidative reactions, hydrolysis and proteolysis. A number of stabilizers may be used e.g., protease inhibitors, polysaccharides such as cellulose and cellulose derivatives, and simple alcohols, such as glycerol; bacteriostatic agents such as phenol, m-cresol and methylparaben; isotonic agents, such as sodium chloride, glycerol, and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or distearoyl-phosphatidylcholine; phosphatidic acids; phosphatidylethanolamines; phosphatidylserines such as distearoyl-phosphatidylserine, dipalmitoylphosphatidylserine and diarachidoylphospahtidylserine; phosphatidylglycerols; phosphatidylinositols; cardiolipins; sphingomyelins. In one example, the stabilizer may be a combination of glycerol, bacteriostatic agents and isotonic agents.

In one example, the peptidyl component or other active ingredient of an injectable formulation is provided as a dry powder in a sterile vial or ampoule. This is mixed with a pharmaceutically acceptable carrier, excipient, and other components of the formulation shortly before or at the time of administration. Such an injectable formulation is produced by mixing components such as a carrier and/or excipient e.g., saline and/or glycerol and/or dissolution agent and/or chelator etc to form a solution to produce a "diluent", and then and sterilizing the diluent e.g., by heat or filtration. The peptidyl component or other active agent is added separately to sterile water to form a solution, sterile-filtered, and a designated amount is placed into each of a number of separate sterile injection bottles. The peptide or other active agent solution is then lyophilized to form a powder and stored e.g., separately from the diluent to retain its stability. Prior to administration, the diluent is added to the injection bottle containing the dried peptidyl component or other active agent. After the predetermined amount of formulation is injected into the patient, the remaining solution may be stored, e.g., frozen or refrigerated.

In another example, the formulation is prepared as a frozen mixture ready for use upon thawing. For example, the peptidyl component or other active agent is combined with the diluent, sterile filtered into multi-use injection bottles or ampoules and frozen prior to use.

Intranasal Formulations

For intranasal administration, powdery preparations having improved absorbability have been proposed. They are prepared e.g., by adsorbing physiologically active linear peptides onto a polyvalent metal compound such as hydroxyapatite or calcium carbonate (e.g., EP 0 681 833 A2). Peptides can be cyclized to improve their stability and resistance to peptidases in the nasal muscoa.

Preferably, the peptide is dispersed homogeneously in and adsorbed homogeneously onto a physiologically acceptable particulate carrier, which can be a physiologically acceptable powdery or crystalline polyvalent metal carrier and/or organic carrier, whose mean particle size is in the range of 20 to 500 microns.

Suitable polyvalent metal component of the carrier include physiologically acceptable metal compounds having more than 2 valency, and may include, for example, aluminum compounds, calcium compounds, magnesium compounds, silicon compounds, iron compounds and zinc compounds. Such metal compounds are commonly used as excipients, stabilizers, filing agents, disintegrants, lubricants, adsorbents and coating agents for medical preparations.

Preferred aluminum compounds include, for example, dry aluminum hydroxy gel, aluminum hydroxychloride, synthetic aluminum silicate, light aluminum oxide, colloidal aluminum silicate hydrate, aluminum magnesium hydroxide, aluminum hydroxide, aluminum hydroxide gel, aluminum sulfate, dihydroxyaluminum aminoacetate, aluminum stearate, natural aluminum silicate, aluminum monostearate and potassium aluminum sulfate. Among them, the preferable aluminum compound is aluminum hydroxide.

Preferred calcium compounds include, for example, apatite, hydroxyapatite, calcium carbonate, calcium disodium EDTA, calcium chloride, calcium citrate, calcium glycerophosphate, calcium gluconate, calcium silicate, calcium oxide, calcium hydroxide, calcium stearate, calcium phosphate tribasic, calcium lactate, calcium pantothenate, calcium oleate, calcium palmitate, calcium D-pantothenate, calcium alginate, calcium phosphate anhydride, calcium hydrogenphosphate, calcium primary phosphate, calcium acetate, calcium saccharate, calcium sulfate, calcium secondary phosphate, calcium para-aminosalicylate and bio-calcilutite compounds. Bio-calcilutite compounds such as crystalline calcium pyrophosphate, calcium secondary phosphate, octacalcium phosphate, tricalcium phosphate and crystalline calcium oxalate are analogous to hydroxyapatite and may also be used as a physiologically acceptable powdery or crystalline carrier. Preferable calcium compounds are hydroxyapatite, calcium carbonate or calcium lactate.

Preferred magnesium compound components of the physiologically acceptable powdery or crystalline carrier include, for example, magnesium L-aspartate, magnesium chloride, magnesium gluconate, magnesium aluminate silicate, magnesium silicate, magnesium oxide, magnesium hydroxide, magnesium stearate, magnesium carbonate, magnesium aluminate metasilicate, magnesium sulfate, sodium magnesium silicate and synthetic sodium magnesium silicate. Among them, preferable magnesium compound is magnesium stearate.

Other metal compounds with more than 2 valency may be silicon compounds such as silicon oxide hydrate, light silicic anhydride, synthetic hydrotalcite, diatomaceous earth and silicon dioxide; iron compounds such as ferrous sulfate; and zinc compounds such as zinc chloride, zinc stearate and zinc sulfate.

Particulate organic carriers may be a fine powder from grain, preferably of rice, wheat, buck wheat, barley, soybean, corn, millet, foxtail millet and the like.

Such formulations may optionally comprise an absorption enhancer. Preferred absorption enhancers which may be one of the components of the nasally administrable composition is a pharmaceutically acceptable natural (e.g. cellulose, starch and their derivatives) or unnatural polymer material. A preferred embodiment of the cellulose and its derivatives is microcrystalline cellulose, methyl cellulose, ethyl cellulose, hydroxypropyl cellulose, hydroxypropylmethyl cellulose, hydroxypropylmethyl cellulose phthalate, cellulose acetate, cellulose acetate phthalate, carboxymethyl cellulose, low carboxymethyl cellulose sodium, carboxymethylethyl cellulose and the like. A preferable embodiment of the starch and its derivatives is corn starch, potato starch, rice starch, glutinous rice starch, wheat starch, pregelatinized starch, dextrin, sodium carboxymethyl starch, hydroxypropyl starch, pullulan and the like. Other natural polymers such as agar, sodium alginate, chitin, chitosan, egg yolk lecithin, gum arabic, tragacanth, gelatine, collagen, casein, albumin, fibrinogen, and fibrin may also be used as absorption enhancer. A preferable embodiment of the unnatural polymer is sodium polyacrylate, polyvinyl pyrrolidone, and the like. Preferred absorption enhancers are fine powder of rice, glutinous rice, starch, gelatine, dextrin, hydroxypropyl cellulose, hydroxypropylmethyl cellulose, polyvinyl pyrrolidone, egg yolk lecithin, gum arabic, tragacanth or a mixture thereof. More preferable absorption enhancers are fine powder of glutinous rice, starch, gelatine, hydroxypropyl cellulose, hydroxypropylmethyl cellulose, polyvinyl pyrrolidone, tragacanth or a mixture thereof. Even more preferable absorption enhancers are fine powder of glutinous rice or hydroxypropyl cellulose. Most preferable absorption enhancer is fine powder of glutinous rice. The mean particle size of the absorption enhancer is preferably not more than 250 microns, more preferably from 20 to 180 microns.

The above absorption enhancers may be used alone or in combination of two or more absorption enhancers in the physiologically acceptable powdery or crystalline carrier.

Water-soluble carriers are preferred to increase adsorption of the active substance in the nasal mucosa. Alternatively, this is achieved by homogeneous dispersion of the active substance in a water-insoluble carrier e.g., hydroxyapatite, calcium carbonate, calcium lactate, aluminum hydroxide or magnesium stearate, preferably in the presence of an absorption enhancer, and homogeneously adsorbing the active substance thereonto.

Calcium carbonate, calcium lactate, aluminum hydroxide or magnesium stearate is usually used as a stabilizer, lubricant, agent to add luster, excipient, dispersing agent or coating agent for a pharmaceutical preparation; however, it has been found that these compounds having a mean particle size of not more than 500 microns can be used as a carrier for the intranasal formulations, and promote absorption of a physiologically active substances into the body by nasal administration.

Additional Components

In another example of the invention, a formulation comprises an additional component or compound e.g., a compound associated with increased re-epithelialization. For example, the formulation can comprise a growth factor, such as, for example, transforming growth factor 13 and/or platelet derived growth factor and/or nerve growth factor and/or heparin binding epidermal growth factor and/or epidermal growth factor and/or keratinocyte growth factor and/or platelet derived activating factor and/or platelet derived epithelial growth factor and/or a fibroblast growth factor an/or a keratinocyte growth factor. For example, Puolakkainen et al., *J. Surg. Res.*, 58: 321-329, 1995 describe formulations comprising transforming growth factor 13; compositions comprising platelet derived growth factor have been described by Lepisto et al., *J. Surg. Res.*, 53: 596-601, 1992; formulations comprising fibroblast growth factor are described, for example, in Brown et al., *Surg.*, 121: 372-380, 1997; formulations comprising nerve growth factor are described in, for example, Matsuda et al., *J. Exp. Med.*, 187: 297-306, 1998.

Modes of Administration

The present invention contemplates any mode of administration of a medicament or formulation as described herein, however one or a plurality of intranasal and/or injected doses is preferred. Combinations of different administration routes are also encompassed e.g., intranasal and intravenous injection.

Compositions according to the present invention are administered in an aqueous solution as a nasal or pulmonary spray and may be dispensed in spray form by a variety of methods known to those skilled in the art. Preferred systems for dispensing liquids as a nasal spray are disclosed in U.S. Pat. No. 4,511,069. Such formulations may be conveniently prepared by dissolving compositions according to the present invention in water to produce an aqueous solution, and rendering the solution sterile. The formulations may be presented in multi-dose containers, for example in the sealed dispensing system disclosed in U.S. Pat. No. 4,511,069. Other suitable nasal spray delivery systems have been described in Transdermal Systemic Medication, Y. W. Chien Ed., Elsevier Publishers, New York, 1985; and in U.S. Pat. No. 4,778,810 (each incorporated herein by reference). Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Nasal and pulmonary spray solutions of the present invention typically comprise the drug or drug to be delivered, optionally formulated with a surface active agent, such as a nonionic surfactant (e.g., polysorbate-80), and one or more buffers. In some embodiments of the present invention, the nasal spray solution further comprises a propellant. The pH of the nasal spray solution is optionally between about pH 6.8 and 7.2, but when desired the pH is adjusted to optimize delivery of a charged macromolecular species (e.g., a therapeutic protein or peptide) in a substantially unionized state. The pharmaceutical solvents employed can also be a slightly acidic aqueous buffer (pH 4-6). Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, benzylalkonimum chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid, and the like. Suitable gases include, but are not limited to, nitrogen, helium, chlorofluorocarbons (CFCs), hydrofluorocarbons (HFC5), carbon dioxide, air, and the like.

Within alternate embodiments, mucosal formulations are administered as dry powder formulations comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5 micron mass median equivalent aerodynamic diameter (MMEAD), commonly about 1 micron MMEAD, and more typically about 2 micron MMEAD. Maximum particle size appropriate for deposition within the nasal passages is often about 10 micron MMEAD, commonly about 8 micron MMEAD, and more typically about 4 micron MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI) which rely on the patient's breath, upon pulmonary or nasal inhalation, to disperse the power into an aerosolized amount. Alternatively, the dry powder may be administered via air assisted devices that use an external power source to disperse the powder into an aerosolized amount, e.g., a piston pump.

Dry powder devices typically require a powder mass in the range from about 1 mg to 20 mg to produce a single aerosolized dose ("puff"). If the required or desired dose of the biologically active agent is lower than this amount, the powdered active agent will typically be combined with a pharmaceutical dry bulking powder to provide the required total powder mass. Preferred dry bulking powders include sucrose, lactose, dextrose, mannitol, glycine, trehalose, human serum albumin (HSA), and starch. Other suitable dry bulking powders include cellobiose, dextrans, maltotriose, pectin, sodium citrate, sodium ascorbate, and the like.

Standard methods are used to administer injectable formulations of the present invention.

The present invention is described further in the following non-limiting examples:

EXAMPLE 1

Isolation of an Inhibitor of AP-1 Signaling

Nucleic acid was isolated from the following bacterial species:

| | |
|---|---|
| 1 | *Archaeoglobus fulgidis* |
| 2 | *Aquifex aeliticus* |
| 3 | *Aeropyrum pernix* |
| 4 | *Bacillus subtilis* |
| 5 | *Bordetella pertussis* TOX6 |
| 6 | *Borrelia burgdorferi* |
| 7 | *Chlamydia trachomatis* |
| 8 | *Escherichia coli* Kl2 |
| 9 | *Haemophilus influenzae* (rd) |
| 10 | *Helicobacter pylori* |
| 11 | *Methanobacterium thermoautotrophicum* |
| 12 | *Methanococcus jannaschii* |
| 13 | *Mycoplasma pneumoniae* |
| 14 | *Neisseria meningitidis* |
| 15 | *Pseudomonas aeruginosa* |
| 16 | *Pyrococcus horikoshii* |
| 17 | *S nechosistis* PCC 6803 |
| 18 | *Thermoplasma volcanium* |
| 19 | *Thermotoga maritima* |

Nucleic acid fragments were generated from the genomic DNA of each genome using 2 consecutive rounds of primer extension amplification using tagged random oligonucleotides with the sequence: 5'-GACTACAAGGACGACGACGACAAGGCTTATCAATCAATCAN$_6$-3' (SEQ ID NO: 166). The PCR amplification was performed using the Klenow fragment of *E. coli* DNA polymerase I in the following primer extension reaction:

| Reagent | Volume |
|---|---|
| DNA (100-200 ng) | 4 μl |
| Oligonucleotide comprising SEQ ID NO: 33 (25 μM) | |
| $H_2O$ | to 17.4 μl. |

Samples were then boiled for 3-5 minutes to denature the nucleic acid isolated from the bacteria, before being snap cooled, to allow the tagged random oligonucleotides to anneal to said nucleic acid. These samples were then added to the following reagents:

| | |
|---|---|
| Klenow buffer | 3 μl |
| dNTP (2 mM) | 3 μl |
| Klenow | 0.6 μl |
| Polyethylene Glycol (8,500) | 6 μl |

Primer extension reactions were then incubated at 15° C. for 30 minutes, then at room temperature for 2 hours, before being heated to 37° C. for 15 minutes.

Samples were boiled for 5 minutes to again denature the nucleic acid, before being snap cooled to allow renaturation of said nucleic acid. Another 0.5 μl of the Klenow fragment of *E. coli* DNA polymerase I was added to each reaction and the samples incubated at 15° C. for 30 minutes, then at room temperature for 2 hours, before being heated to 37° C. for 15 minutes.

Following boiling the samples, following snap cooling another 2 rounds of primer extension were completed using the tagged random oligonucleotide:

```
                                           (SEQ ID NO: 167)
5'-GACTACAAGGACGACGACGACAAGGCTTATCAATCAATCAN9-3'.
```

To complete this the following reagents were added to the samples of the previous step:

| | |
|---|---|
| Oligonucleotide (25 μM) | 4 μl |
| Klenow Buffer | 1 μl |
| dNTP(2 mM) | 3 μl |
| Klenow | 0.5 μl |
| $H_2O$ | to 40 μl |

Samples were then incubated at 15° C. for 30 minutes, then at room temperature for 2 hours, before being heated to 37° C. for 15 minutes.

Samples were boiled for 5 minutes to again denature the nucleic acid, before being snap cooled to allow renaturation of said nucleic acid. Another 0.50 of the Klenow fragment of *E. coli* DNA polymerase I was added to each reaction and the samples incubated at 15° C. for 30 minutes, then at room temperature for 2 hours, before being heated to 37° C. for 15 minutes.

Following completion of the primer extension amplification all sample volumes were increased to 5000 with TE buffer and added to an Amicon spin column. These columns were then centrifuged for 15 minutes at 3,800 rpm in a microcentrifuge. Columns were then inverted and 30 μl of TE buffer was added before the columns were centrifuged for 2 minutes at 3,800 rpm, with this fraction collected for later use. The Klenow amplified DNA was then used in subsequent DNA manipulations.

The now purified primer extension products were then used in a PCR reaction with an oligonucleotide comprising the following sequence:

5'-GAGA**GAAT*TC***AGG*TCA*GA*CTA*CAAGGACGACGACGACAAG-3' (SEQ ID NO: 168)., wherein an EcoRI restriction endonuclease site is shown in bold text, and three stop codons are in italics with a dotted underline. Note that each of the stop codons is in a different reading frame.

Thus, the following PCR reaction was used:

| | |
|---|---|
| Oligonucleotide comprising SEQ ID NO: 35 (10 μM) | 12 μl |
| PCR buffer | 5 μl |
| dNTP (2 mM) | 5 μl |
| Taq polymerase (Boehringer) 5.5 U/μl) | 0.4 μl |
| H$_2$O | 26.6 μl |
| Klenow amplified DNA | 2 μl |

Reactions were then cycled in a thermocycler using the following program:

95° C. for 2 min; 60° C. for 30 sec; 72° C. for 1 min;

95° C. for 20 sec; 60° C. for 30 sec; 72° C. for 1 min (repeated 29 times); and

72° C. for 5 min.

PCR products were then purified using Amicon spins columns which fractionate on the basis of size.

The PCR products were then analyzed by electrophoresis on standard TAE-agarose gels to determine the approximate size of the nucleic acid fragments generated as shown in FIG. 2. The nucleic acid concentration of the samples was also determined.

PCR products from each of the 19 bacterial species were then pooled to generate a biodiverse nucleic acid library. To do so, DNA from each organism was added in an equimolar amount when compared to the amount of nucleic acid added to the pool from the organism with the smallest genome. Between 1 μg and 10 μg of DNA from each organism was used, depending on the genome size of the organism from which the DNA was obtained.

Amplified fragments were digested with EcoRI and Acc651. The resulting fragments were then purified using a QIAQuick PCR purification column (Qiagen) essentially according to manufacturer's instructions. The expression vector pMF4-5 (Phylogical Limited, Perth, Australia) was also digested with EcoRI and Acc651, treated with shrimp alkaline phosphatase and then purified using a QIAQuick PCR purification column (Qiagen) essentially according to manufacturer's instructions. Ligations were then performed at a molar ratio of 10:1 insert:vector, and transformed into TOP10 electrocompetent cells (Invitrogen).

These vectors were then isolated from bacteria using standard methods and transformed into the PRT51 yeast strain (with the genotype MATa, his3, trp1, ura3, 6 LexA-LEU2, lys2::3 cIop-LYS2, CYH2R, ade2::G418-pZero-ade2, met15::Zeo-pBLUE-met15, his5::hygroR). Transformants were then aliquoted and snap frozen in 15% glycerol.

The bait and prey used in the present screen were JUN1 and JUNZ fragments of c-Jun. Briefly, nucleic acid encoding the JUN1 protein was cloned into the prey vector pJFK in operable connection with a nuclear localisation signal, and a B42 activation domain. The nucleic acid encoding the JUNZ protein was cloned into the bait vector pDD in operable connection with the LexA DNA binding domain. The pDD vector also contains a nucleic acid encoding the HIS3 gene. These vectors were then transformed into the yeast strain PRT480 (with the genotype MATa, his3, trp1, ura3, 4 LexA-LEU2, lys2::3 cIop-LYS2, CANR, CYH2R, ade2::2 LexA-CYH2-ZEO, his5::1 LexA-URA3-G418).

The yeast that carry the bait and prey proteins and the potential blocking peptides were then mass mated, and from approximately 300,000 clones, 95 positives were identified (i.e., approximately 1/3000). Only a few of these primary hits were shown to have activity as AP-1 signaling inhibitors in an AP-1-dependent transcription assay (see below).

Two methods of analysis were used to identify interaction-blocking activity:

The first of these comprised plating approximately 500 cells per half plate onto HTU media containing plates and counting the number of colonies growing after 3 days. In these conditions, an interaction of JUN1 and JUNZ enables the cells to grow.

Accordingly, a reduction in the number of colonies indicates that the library being screened comprises peptide inhibitors of the JUN1/JUNZ interaction.

The second screening method involved isolation and streaking of 10 individual colonies to new HTU media containing plates and analysing for growth of new single colonies. After 3 days, those that express a peptide inhibitor generally have very little or no new growth, while those that do not express a peptide inhibitor have re-grown a streak of single colonies. As a positive control a known inhibitor of JUN1/JUNZ interaction, FosZ was used. As a negative control empty pYTB3 vector with no peptide insert was used. A score of 1-10 given depending on growth of 10 individual clones of each peptide compared to the two control samples.

The score from method 1 and method 2 was then combined to determine if a specific colony expressed a peptide inhibitor of JUN1/JUNZ interaction. In the present case a cell expressing a peptide inhibitor was one that showed >50% reduction of growth compared to negative control in both tests.

All scoring was performed by two independent individuals and scores of both individuals were combined.

Following screening peptides comprising a sequence set forth in any one of SEQ ID NOs: 26, 28, 30, 32, 34, 36, 38, 40, 42, 44, 46, 48, 50, 52, 54, 56, 58, 60, 62, 64, 66, 68, 70 or 72 were identified.

In one validation assay, the ability of the peptides to interact with JUN1 was then confirmed with a forward two-hybrid assay. Each of the identified peptides capable of inhibiting the interaction of JUN1 and JUNZ was cloned into the bait vector pDD. Additionally, nucleic acid encoding a peptide known not to inhibit the interaction between JUN1 and JUNZ was also cloned into pDD. The pDD vector and the JUN1 prey vector was transformed into the yeast strain PRT480 and the interaction of the encoded peptide and JUN1 assessed by determining the amount of growth in the absence of uracil.

In another validation assay, the ability of the peptides to block AP-1-dependent expression of a luciferase gene was determined. The K562 cell line was stably-transfected with the AP-1 luciferase reporter of the Mercury Profiling kit (Clontech, U.S.A.), and a clonal cell line established. In 24-well tissue culture plate format, K562-AP1 cells were transfected with either pcDNA3-peptide-negative control, pcDNA3-TAM67 (dominant negative cJun) positive control, or pcDNA3-peptide. Transfections were performed using Lipofectamine2000 (Life Technologies), according to manufacturer's instructions, and each transfection included a co-transfected *Renilla* plasmid as a transfection control. Transfections were incubated for 24 hours and AP-1 expression was induced with PMA. At 48 hours post-transfection, cells were collected and protein lysates extracted for luciferase assay according to Promega's Dual Reporter Luciferase kit and associated protocols. Luciferase expression levels were measured in a luminometer, and normalised to the expression levels of the *Renilla* co-transfection control. Luciferase assays were performed in quadruplicate (two independent duplicates). The results for each peptide subjected to statistical analysis of variance (ANOVA) to determine if they were different to TAM67 (Jun positive control for AP-1 inhibition) or pcDNA3-peptide-negative control (negative control for AP-1 activation inhibition/activation).

This selection process yielded the peptides set forth in SEQ ID Nos: 26-72.

Base peptide sequences were modified to produce the corresponding retroinverted peptide sequences e.g., to enhance serum stability and/or conjugated to the TAT transport sequence, as exemplified by SEQ ID Nos: 73-120.

EXAMPLE 2

Inhibition of Neutrophil Infiltration by Inhalation of Peptidyl Inhibitors of AP-1 Signaling in an Animal Model of ARDS and Sepsis 1.1 Materials and Methods
Animals 8-12 week old C57/B16 mice were purchased from the Animal Resource Center, Murdoch University, Western Australia and used for all experiments. All experiments were approved by the necessary institutional animal ethics committees and were performed in accordance with the National Health and Medical Research Council (NHMRC) Australian Code of Practice for the Care and Use of Animals for Scientific Purposes.

Peptides

Peptides used were synthesised by Mimotopes Pty Ltd (Melbourne, Australia) and supplied as a lyophilised powder (purity >90%).

Peptides comprising the sequences set forth in SEQ ID NOs: 104 and 106 and 108 are D-form retro-inverted mimetics of peptides originally identified in a screen for inhibitors of AP-1 signaling e.g., by virtue of inhibiting c-Jun dimerization (as described in Example 1, i.e., peptides comprising amino acid sequences set forth in SEQ ID NOs: 57, 59 and 61, respectively), each being fused to the TAT 10-mer for penetration across cell membranes, with a linking glycine between the peptide and TAT sequence to facilitate the independent folding of each of said components.

Procedure

Test animals were pre-treated 1 hour before LPS administration, by intra nasal delivery of 10 mg/kg body weight of retroinverted peptide D-PYC35-TAT (SEQ ID NO: 104) or D-PYC36-TAT (SEQ ID NO: 104), or 5 mg/kg body weight D-PYC38-TAT (SEQ 30 ID NO: 106). A negative control was also performed using 10 mg/kg body weight of a scrambled sequence of SEQ ID NO: 104 designated D-PYC36scrambled-TAT. A repeat treatment of peptide was also administered intranasally with LPS (10 µg/mouse) 1 hour later. Six hours after LPS treatment, bronchoalveolar lavage (BAL) was performed on the animals using 1 ml GKN/0.2% BSA. Cell counts were obtained to determine total cell numbers and differential counts were obtained on cytocentrifuge slide preparations to elucidate the percentage neutrophils in BAL. In control experiments to demonstrate the effect of LPS administration on neutrophilic inflammation, LPS was administered intranasally in the absence of any treatment and bronchoalveolar lavage performed 1 hour or 4 hours or 6 hours later. Data are presented in FIG. 1. The data shows significant induction of neutrophil infiltration into BAL by the LPS treatment, and significantly-reduced neutrophil infiltration in BAL in the presence of SEQ ID NO: 104 or 106 or 108, but not in the presence of the scrambled control peptide.

EXAMPLE 3

Inhibition of Neutrophil Infiltration by Injection of Peptidyl Inhibitors of AP-1 Signaling in an Animal Model of ARDS and Sepsis 1.1 Materials and Methods
20 Animals 8-10 week old female C57/B16 mice were purchased from the Animal Resource Centre, Murdoch University, Western Australia and used for all experiments. Mice were maintained free of pathogens at the Telethon Institute for Child Health Research (TICHR). All animal care handling techniques and experimental methods were approved by the TICHR Animal Experimentation Ethics Committee, which operates under the strict guidelines set out by the National Health and Medical Research Council (NHMRC).

Peptides

Peptides used were synthesised by Mimotopes Pty Ltd (Melbourne, Australia) and supplied as a lyophilised powder (purity >90%).

Peptides comprising the sequence set forth in SEQ ID NO: 106 is a D-form retro-inverted mimetic of a peptide originally identified in a screen for inhibitors of AP-1 signaling e.g., by virtue of inhibiting c-Jun dimerization (as described in Example 1, i.e., the peptide comprising the amino acid sequence set forth in SEQ ID NO: 59, fused to the TAT 10-mer for penetration across cell membranes, with a linking glycine between the peptide and TAT sequence to facilitate the independent folding of each of said components. The peptide designated D-PYC36scrambled-TAT comprises a sequence that is scrambled relative to SEQ ID NO: 106, and acts as a negative control.

Procedure

Test animals were pre-treated 20 minutes before LPS administration, with an intravenous injection of 10 mg/kg body weight of retroinverted peptide D-PYC36-TAT (SEQ ID NO: 106) or the D-PYC36scrambled-TAT negative control in 200 µl PBS. Repeat injections of peptide or negative control were also performed 2 hours and 4 hours after LPS administration.

Six hours after LPS treatment, bronchoalveolar lavage (BAL) was performed on the animals using 1 ml GKN/0.2% BSA. Briefly, animals were tracheotomized, and 1 ml PBS was gently instilled to inflate the lungs and then retrieved. This process was repeated three times. Cells were collected by centrifugation of BAL fluid for 7 mins at 1500 rpm. Total cell counts were obtained to determine total cell numbers and differential counts were obtained on cytocentrifuge slide preparations stained using DiffQuik (Lab Aids Pty Ltd, Narrabeen, Australia) to elucidate the percentage neutrophils in BAL.

Data are presented in FIG. 2. The data shows significant induction of neutrophil infiltration into BAL by the LPS treatment, and significantly-reduced neutrophil infiltration in BAL by repeated injection of SEQ ID NO: 106, but not following administration of the scrambled control peptide.

We claim:

1. A method of treatment of acute respiratory distress syndrome (ARDS) and/or one or more ARDS related complications thereof comprising administering to a subject in need thereof a formulation comprising an effective amount of a peptide consisting of the sequence SEQ ID NO: 108 for a time and under conditions sufficient to reduce neutrophilic inflammation and/or enhance or induce alveolar re-epithelialization in a subject that has suffered alveolar epithelial injury.

2. The method of claim 1, wherein the subject is suffering from breathing difficulty and/or has reduced breathing capability and the formulation is administered to the subject by injection.

3. The method of claim 1, wherein the formulation is administered to the subject by intravenous injection.

4. The method of claim 1, wherein the formulation is administered to the subject by intramuscular injection.

5. The method of claim 1, wherein the formulation is administered to the subject by subcutaneous injection.

6. A method of treatment comprising:
   (i) identifying a subject suffering from acute respiratory distress syndrome (ARDS) and/or one or more ARDS related complications thereof;
   (ii) obtaining a composition comprising a peptide consisting of the sequence SEQ ID NO: 108;
   (iii) formulating the composition of (ii) with a suitable carrier and/or excipient wherein said composition is in an amount sufficient to reduce neutrophilic inflammation and/or enhance or induce alveolar re-epithelialization in a subject that has suffered alveolar epithelial injury, and/or reduce alveolar epithelial loss or damage in a subject that has not yet suffered significant damage to the alveolar epithelium; and
   (iv) administering said formulation to said subject.

7. The method of claim 6, wherein the formulation is administered to the subject by intravenous injection.

8. The method of claim 6, wherein the formulation is administered to the subject by intramuscular injection.

9. The method of claim 6, wherein the formulation is administered to the subject by subcutaneous injection.

10. The method of claim 6, wherein the formulation comprises the peptide consisting of SEQ ID NO: 108 conjugated to a hydrolysable polyethylene glycol (PEG).

11. The method of claim 6, the formulation additionally comprising a growth factor.

12. The method of claim 1, wherein the comprises the peptide consisting of SEQ ID NO: 108 conjugated to a hydrolysable polyethylene glycol (PEG).

13. The method of claim 1, the formulation additionally comprising a growth factor.

* * * * *